(12) United States Patent
Macielag et al.

(10) Patent No.: US 9,732,061 B2
(45) Date of Patent: Aug. 15, 2017

(54) CINNOLINE DERIVATIVES USEFUL AS CB-1 RECEPTOR INVERSE AGONISTS

(71) Applicant: Janssen Pharmaceutica NV, Beerse (BE)

(72) Inventors: Mark Joseph Macielag, Spring House, PA (US); Yue-Mei Zhang, Spring House, PA (US); Bart L. DeCorte, Spring House, PA (US); Michael N. Greco, Lansdale, PA (US); Donald W. Ludovici, Quakertown, PA (US); Michael H. Parker, Chalfont, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/992,464

(22) Filed: Jan. 11, 2016

(65) Prior Publication Data

US 2016/0200719 A1 Jul. 14, 2016

Related U.S. Application Data

(60) Provisional application No. 62/102,126, filed on Jan. 12, 2015.

(51) Int. Cl.
| | | |
|---|---|---|
| *C07D 401/12* | (2006.01) | |
| *C07D 409/14* | (2006.01) | |
| *C07D 405/14* | (2006.01) | |
| *C07D 417/14* | (2006.01) | |
| *C07D 401/04* | (2006.01) | |
| *C07D 403/12* | (2006.01) | |
| *C07D 237/28* | (2006.01) | |

(52) U.S. Cl.
CPC ........ *C07D 401/12* (2013.01); *C07D 237/28* (2013.01); *C07D 401/04* (2013.01); *C07D 403/12* (2013.01); *C07D 405/14* (2013.01); *C07D 409/14* (2013.01); *C07D 417/14* (2013.01)

(58) Field of Classification Search
None
See application file for complete search history.

(56) References Cited

FOREIGN PATENT DOCUMENTS

| EP | 1820504 | 8/2007 | |
|---|---|---|---|
| WO | WO 2005/115972 | 12/2005 | |
| WO | WO 2009/053799 | 4/2009 | |
| WO | WO 2009/136191 A1 * | 11/2009 | ........... C07D 237/28 |
| WO | WO 2015/130445 | 9/2015 | |

OTHER PUBLICATIONS

International Search Report re: PCT/US2016/012807 dated Apr. 7, 2016.

* cited by examiner

*Primary Examiner* — Brian J Davis
(74) *Attorney, Agent, or Firm* — Thomas J. Dodd

(57) ABSTRACT

The present invention is directed to cinnoline derivatives pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

13 Claims, No Drawings

CINNOLINE DERIVATIVES USEFUL AS CB-1 RECEPTOR INVERSE AGONISTS

CROSS-REFERENCE TO RELATED APPLICATIONS

The present application claims the benefits of the filing of U.S. Provisional Application No. 62/102,126 filed Jan. 12, 2015. The complete disclosures of the aforementioned related patent applications are hereby incorporated herein by reference for all purposes.

FIELD OF THE INVENTION

The present invention is directed to cinnoline derivatives pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated with serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/or skeletal muscle, to avoid these adverse effects.

Thus, there is a need for peripherally restricted cannabanoid-1 receptor (CB1R) inverse agonists for the treatment of, for example metabolic disorders, such as obesity, Type II diabetes mellitus, metabolic syndrome, Syndrome X, and the like.

SUMMARY OF THE INVENTION

The present invention is directed to compounds of formula (I)

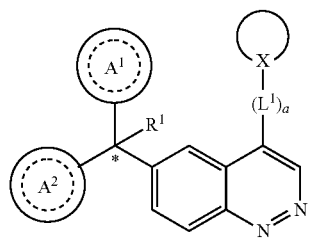

(I)

wherein
$R^1$ is selected from the group consisting of hydrogen and hydroxy;

is selected from the group consisting of phenyl, furyl, thienyl, thiazolyl, benzothiazolyl and benzo[d][1,3]dioxolyl; wherein the phenyl, furyl, thienyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^AR^B$; wherein $R^A$ and $R^B$ are each independently selected from the group consisting of hydrogen and $C_{1-4}$alkyl; provided that each substituent is bound to a carbon atom of the ring;

is selected from the group consisting of phenyl, furyl, thienyl, thiazolyl, benzothiazolyl and benzo[d][1,3]dioxolyl; wherein the phenyl, furyl, thienyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^CR^D$; wherein $R^C$ and $R^D$ are each independently selected from the group consisting of hydrogen and $C_{1-4}$alkyl; provided that each substituent is bound to a carbon atom of the ring;

a is an integer from 0 to 1;
$L^1$ is selected from the group consisting of —N($R^2$)—, —N($R^2$)—$CH_2$— and —N($R^2$)—$CH_2CH_2$—; wherein $R^2$ is selected from the group consisting of hydrogen and $C_{1-2}$alkyl; and wherein the $L^1$ is bound to the cinnoline core through a nitrogen atom;

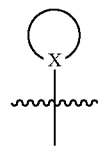

is selected from the group consisting of

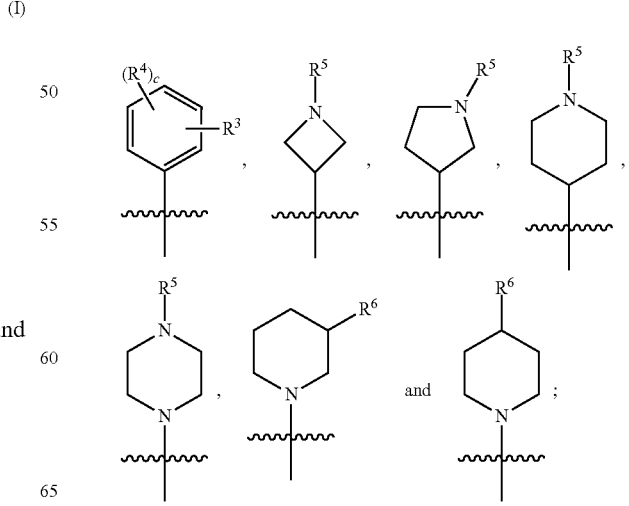

(wherein X is selected from the group consisting of C and N);

provided that when

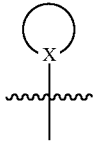

is selected from the group consisting of

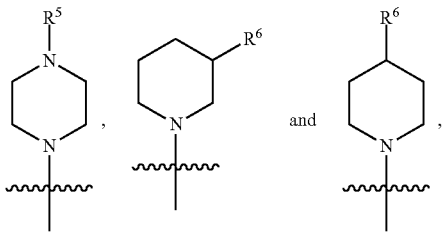

then a is 0 or a is 1 and $L^1$ is other than —N($R^2$) and —N($R^2$)—$CH_2$—;

wherein $R^3$ is selected from the group consisting of hydrogen, halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —$CO_2H$, —C(O)O—($C_{1-4}$alkyl), —($C_{1-4}$alkyl)-$CO_2H$, —($C_{1-4}$alkyl)-C(O)O—($C_{1-4}$alkyl), —$SO_2$—($C_{1-4}$alkyl) and —$SO_2$-(halogenated $C_{1-4}$alkyl);

c is an integer from 0 to 2;

each $R^4$ is independently selected from the group consisting of halogen, $C_{1-4}$alkyl, halogenated $C_{1-2}$alkyl, $C_{1-4}$alkoxy and halogenated $C_{1-2}$alkoxy;

wherein $R^5$ is selected from the group consisting of —C(O)—($C_{1-4}$alkyl), —C(O)O—($C_{1-4}$alkyl), —$SO_2$—($C_{1-4}$alkyl) and —$SO_2$-(halogenated $C_{1-4}$alkyl); and

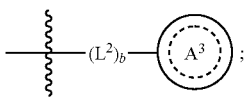

wherein $R^6$ is selected from the group consisting of $C_{1-4}$alkyl, halogenated $C_{1-4}$alkyl, —C(O)—$NR^{E1}R^F$, —$NR^E$—C(O)—($C_{1-4}$alkyl), —$NR^E$—$SO_2$—($C_{1-4}$alkyl), and

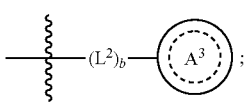

wherein $R^E$ and $R^F$ are each independently selected from the group consisting of hydrogen, methyl and ethyl;

b is an integer from 0 to 1;

$L^2$ is selected from the group consisting of —$CH_2$—, —$CH_2CH_2$—, —NH—, —N($CH_3$)—, —C(O)— and —$SO_2$—;

provided that when

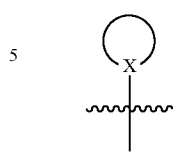

is selected from the group consisting of

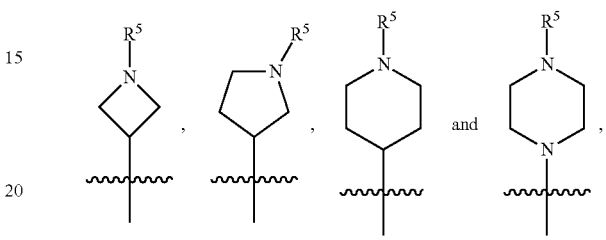

then b is 0 or b is 1 and $L^2$ is other than —NH— or —N($CH_3$)—;

is selected from the group consisting of phenyl, furan-2-yl, thien-2-yl;

wherein the phenyl is optionally substituted with a substituent selected from the group consisting of halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —$CO_2H$, —C(O)O—($C_{1-4}$alkyl), —($C_{1-4}$alkyl)-$CO_2H$, —($C_{1-4}$alkyl)-C(O)O—($C_{1-4}$alkyl), —$SO_2$—($C_{1-4}$alkyl) and —$SO_2$-(halogenated $C_{1-4}$alkyl); and wherein the phenyl is further optionally substituted with one to two additional substituents independently selected from the group consisting of halogen, $C_{1-4}$alkyl, halogenated $C_{1-2}$alkyl, $C_{1-4}$alkoxy and halogenated $C_{1-2}$alkoxy;

and wherein the furan-2-yl or thien-2-yl is optionally substituted with a substituent selected from the group consisting of halogen, $C_{1-4}$alkyl, halogenated $C_{1-4}$alkyl, $C_{1-4}$alkoxy, halogenated $C_{1-4}$alkoxy, —$CO_2H$, —C(O)O—($C_{1-4}$alkyl) and —C(O)—$NR^GR^H$; wherein $R^G$ and $R^H$ are each independently selected from the group consisting of hydrogen, methyl and ethyl;

and stereoisomers, tautomers and pharmaceutically acceptable salts thereof.

The present invention is further directed to processes for the preparation of the compounds of formula (I). The present invention is further directed to a product prepared according to any of the process(es) described herein.

The present invention is further directed to intermediate compounds useful in the synthesis of the compounds of formula (I), as described and defined in the synthesis schemes and examples which follow herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain). In another embodiment, the present invention is directed to a composition comprising a compound of formula (I) for the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain).

Another example of the invention is the use of any of the compounds described herein in the preparation of a medicament for treating: (a) obesity, (b) Type I diabetes, (c) Type II diabetes, (d) gestational diabetes, (e) latent autoimmune diabetes of adults (LADA), (f) pre-diabetes, (g) insulin resistance, (h) inadequate glucose tolerance, (i) dyslipidemia (including, but not limited to elevated triglycerides and LDL, and low HDL), (j) nonalcoholic steatohepatitis (NASH), (k) cirrhosis, (l) fatty liver disease, (m) atherosclerosis, (n) hypertension, (o) inflammatory bowel disease, (p) Alzheimer's disease, (q) osteoporosis, (r) multiple sclerosis, (s) traumatic brain injury, (t) arthritis, or (u) neuropathic pain, in a subject in need thereof. In another example, the present invention is directed to a compound as described herein for use in method for treating a disorder selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain, in a subject in need thereof.

In additional embodiments the present invention is as described herein.

DETAILED DESCRIPTION OF THE INVENTION

The present invention is directed to compounds of formula (I)

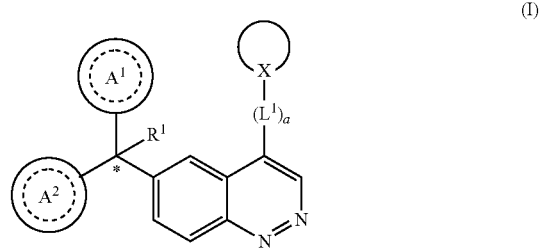

wherein $R^1$,

a, $L^1$ and

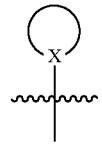

are as herein defined; and stereoisomers, tautomers and pharmaceutically acceptable salts thereof.

The compounds of formula (I) of the present invention are CB-1 receptor inverse agonists, useful in the treatment of metabolic disorders, including but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

In an embodiment, the present invention is directed to compounds of formula (I) wherein

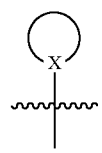

is selected from the group consisting of

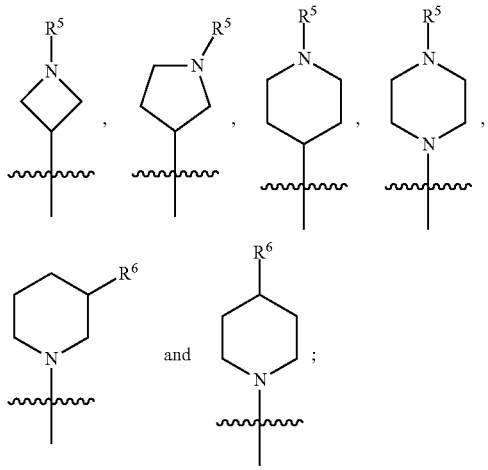

R⁵ is

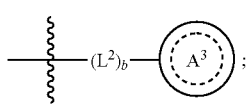

R⁶ is

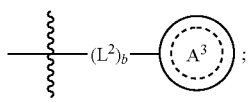

b is an integer from 0 to 1; L² is selected from the group consisting of —CH₂—, —CH₂CH₂—, —NH—, —N(CH₃)—, —C(O)— and —SO₂—; provided that when

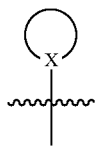

is selected from the group consisting of

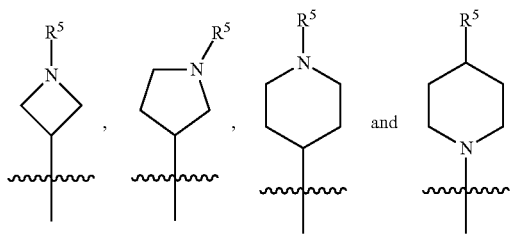

then b is 0 or b is 1 and L² is other than —NH— or —N(CH₃)—;

is selected from the group consisting of phenyl, furan-2-yl, thien-2-yl; wherein the phenyl is optionally substituted with a substituent selected from the group consisting of halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —CO₂H, —C(O)O—($C_{1-4}$alkyl), —($C_{1-4}$alkyl)-CO₂H, —($C_{1-4}$alkyl)-C(O)O—($C_{1-4}$alkyl), —SO₂—($C_{1-4}$alkyl) and —SO₂-(halogenated $C_{1-4}$alkyl); and wherein the phenyl is further optionally substituted with one to two additional substituents independently selected from the group consisting of halogen, $C_{1-4}$alkyl, halogenated $C_{1-2}$alkyl, $C_{1-4}$alkoxy and halogenated $C_{1-2}$alkoxy; and wherein the furan-2-yl or thien-2-yl is optionally substituted with a substituent selected from the group consisting of halogen, $C_{1-4}$alkyl, halogenated $C_{1-4}$alkyl, $C_{1-4}$alkoxy, halogenated $C_{1-4}$alkoxy, —CO₂H, —C(O)O—($C_{1-4}$alkyl) and —C(O)—NR^G R^H; wherein R^G and R^H are each independently selected from the group consisting of hydrogen, methyl and ethyl; and stereoisomers, tautomers and pharmaceutically acceptable salt thereof In another embodiment, the present invention is directed to compounds of formula (I) wherein

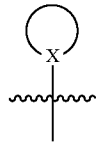

is selected from the group consisting of

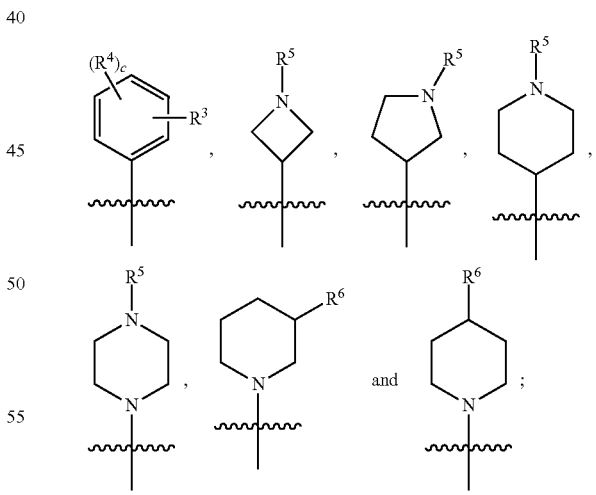

wherein R³ is selected from the group consisting of hydrogen, halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —CO₂H, —C(O)O—($C_{1-4}$alkyl), —($C_{1-4}$alkyl)-CO₂H, —($C_{1-4}$alkyl)-C(O)O—($C_{1-4}$alkyl), —SO₂—($C_{1-4}$alkyl) and —SO₂-(halogenated $C_{1-4}$alkyl); c is an integer from 0 to 2; and wherein each R⁴ is independently selected from the group consisting of halogen, $C_{1-4}$alkyl, halogenated $C_{1-2}$alkyl, $C_{1-4}$alkoxy and halogenated $C_{1-2}$alkoxy; wherein $R^5$ is selected from the group consisting of —C(O)—($C_{1-4}$alkyl), —C(O)O—($C_{1-4}$alkyl), —$SO_2$—($C_{1-4}$alkyl) and —$SO_2$-(halogenated $C_{1-4}$alkyl); wherein $R^6$ is selected from the group consisting of $C_{1-4}$alkyl, halogenated $C_{1-4}$alkyl, —C(O)—$NR^{E1}R^F$, —$NR^E$—C(O)—($C_{1-4}$alkyl) and —$NR^E$—$SO_2$—($C_{1-4}$alkyl); and wherein $R^E$ and $R^F$ are each independently selected from the group consisting of hydrogen, methyl and ethyl; and stereoisomers, tautomers and pharmaceutically acceptable salt thereof.

In an embodiment, the present invention is directed to compounds of formula (I) wherein $R^1$ is hydrogen. In another embodiment, the present invention is directed to compounds of formula (I) wherein $R^1$ is hydroxy.

In an embodiment, the present invention is directed to compounds of formula (I) wherein

is selected from the group consisting of phenyl, furyl, thienyl and thiazolyl; wherein the phenyl, furyl, thienyl or thiazolyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, C(O)O—$C_{1-4}$alkyl and $NR^AR^B$; wherein $R^A$ and $R^B$ are each independently selected from the group consisting of hydrogen and $C_{1-2}$alkyl; provided that each substituent is bound to a carbon atom of the ring. In another embodiment, the present invention is directed to compounds of formula (I)

is selected from the group consisting of phenyl and thiazol-2-yl; wherein the phenyl is optionally substituted with a substituent selected from the group consisting of halogen and $C_{1-2}$alkoxy.

In another embodiment, the present invention is directed to compounds of formula (I) wherein

is selected from the group consisting of 4-chlorophenyl, 4-fluorophenyl, 4-methoxyphenyl and thiazol-2-yl. In another embodiment, the present invention is directed to compounds of formula (I) wherein

is selected from the group consisting of 4-chlorophenyl, 4-fluorophenyl, and thiazol-2-yl.

In an embodiment, the present invention is directed to compounds of formula (I) wherein

is selected from the group consisting of phenyl, furyl, thienyl and thiazolyl; wherein the phenyl, furyl, thienyl or thiazolyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, C(O)O—$C_{1-4}$alkyl and $NR^AR^B$; wherein $R^A$ and $R^B$ are each independently selected from the group consisting of hydrogen and $C_{1-2}$alkyl; provided that each substituent is bound to a carbon atom of the ring. In another embodiment, the present invention is directed to compounds of formula (I) wherein

is phenyl; wherein the phenyl is optionally substituted with a substituent selected from the group consisting of halogen.

In another embodiment, the present invention is directed to compounds of formula (I) wherein

is selected from the group consisting of 4-chlorophenyl and 4-fluorophenyl. In another embodiment, the present invention is directed to compounds of formula (I) wherein

is 4-chlorophenyl.

In an embodiment, the present invention is directed to compounds of formula (I) wherein a is 0. In another embodiment, the present invention is directed to compounds of formula (I) wherein a is 1.

In an embodiment, the present invention is directed to compounds of formula (I) wherein $L^1$ is selected from the group consisting of —N($R^2$)—, —N($R^2$)—$CH_2$— and —N($R^2$)—$CH_2CH_2$—; and wherein the $L^1$ is bound to the cinnoline core through a nitrogen atom. In an embodiment, the present invention is directed to compounds of formula (I) wherein $R^2$ is selected from the group consisting of hydrogen and methyl.

In another embodiment, the present invention is directed to compounds of formula (I) wherein $L^1$ is selected from the group consisting of —NH—, —NH—$CH_2$— and —NH—$CH_2CH_2$—; and wherein the $L^1$ is bound to the cinnoline core through a nitrogen atom. In another embodiment, the present invention is directed to compounds of formula (I) wherein $L^1$ is selected from the group consisting of —NH— and —NH—CH$_2$—; and wherein the L$^1$ is bound to the cinnoline core through a nitrogen atom.

In an embodiment, the present invention is directed to compounds of formula (I) wherein

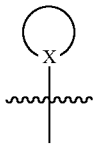

is selected from the group consisting of

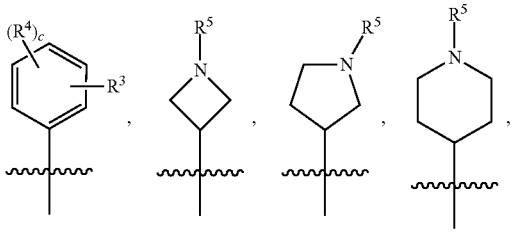

In another embodiment, the present invention is directed to compounds of formula (I) wherein

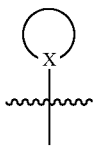

is selected from the group consisting of

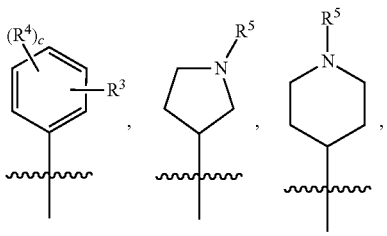

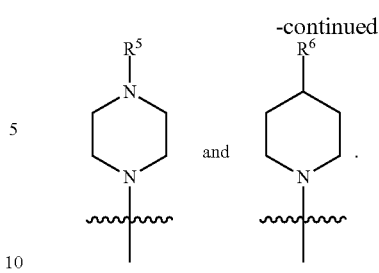

and

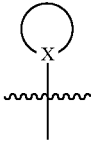

In an embodiment, the present invention is directed to compounds of formula (I) wherein

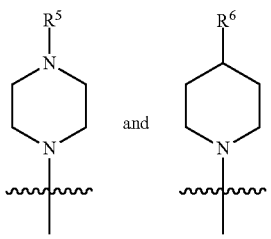

is selected from the group consisting of phenyl, 3-(trifluoromethyl)-phenyl, 4-(trifluoromethyl)-phenyl, 4-methoxyphenyl, 4-hydroxy-phenyl, 3-carboxy-phenyl, 4-carboxy-phenyl, 1-(t-butoxycarbonyl)-piperidin-4-yl, 1-(trifluoromethyl-sulfonyl)-piperidin-4-yl, 4-(trifluoromethyl-sulfonyl)-piperazin-1-yl, 1-(trifluoromethyl-sulfonyl)-pyrrolidin-3-yl, 1-(phenyl-sulfonyl)-pyrrolidin-3-yl, 1-(phenyl-methyl)-pyrrolidin-3-yl, 1-(4-carboxy-phenyl)-piperidin-4-yl, 1-(phenyl-carbonyl)-piperidin-4-yl, 1-(phenyl-sulfonyl)-piperidin-4-yl, 1-((2-carboxy-phenyl)-sulfonyl)-piperidin-4-yl, 1-((3-carboxy-phenyl)-sulfonyl)-piperidin-4-yl, 1-((4-carboxy-phenyl-sulfonyl)-piperidin-4-yl, 1-((2-carboxy-phenyl)-methyl)-piperidin-4-yl, 1-((3-carboxy-phenyl)-methyl)-piperidin-4-yl, 1-((4-carboxy-phenyl)-methyl)-piperidin-4-yl, 1-(phenyl-ethyl)-piperidin-4-yl, 1-((3-carboxy-phenyl)-ethyl)-piperidin-4-yl, 1-((4-carboxy-phenyl)-ethyl)-piperidin-4-yl, 1-((5-carboxy-furan-2-yl)-sulfonyl)-piperidin-4-yl, 1-((5-carboxy-thien-2-yl)-sulfonyl)-piperidin-4-yl, 1-((5-carboxy-thien-2-yl)-methyl)-piperidin-4-yl, 1-((4-carboxy-thien-2-yl)-sulfonyl)-piperidin-4-yl, 1-(phenyl-methyl)-piperazin-1-yl and 1-(phenyl-amino)-piperidin-1-yl.

In another embodiment, the present invention is directed to compounds of formula (I) wherein

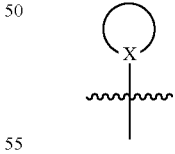

is selected from the group consisting of phenyl, 3-(trifluoromethyl)-phenyl, 4-(trifluoromethyl)-phenyl, 4-methoxyphenyl, 1-(t-butoxycarbonyl)-piperidin-4-yl, 1-(trifluoromethyl-sulfonyl)-piperidin-4-yl, 4-(trifluoromethyl-sulfonyl)-piperazin-1-yl, 1-(trifluoromethyl-sulfonyl)-pyrrolidin-3-yl, 1-(phenyl-sulfonyl)-pyrrolidin-3-yl, 1-(phenyl-carbonyl)-piperidin-4-yl, 1-(phenyl-sulfonyl)-piperidin-4-yl, 1-((3-carboxy-phenyl)-sulfonyl)-piperidin-4-yl, 1-((4-carboxy-phenyl-sulfonyl)-piperidin-4-yl, 1-((3-carboxy-phenyl)-methyl)-piperidin-4-yl, 1-((5-carboxy-thien-2-yl)-sulfonyl)-piperidin-4-yl, 1-((5-carboxy-thien-2-yl)-methyl)-piperidin- 4-yl, 1-((4-carboxy-thien-2-yl)-sulfonyl)-piperidin-4-yl and 1-(phenyl-amino)-piperidin-1-yl.

In another embodiment, the present invention is directed to compounds of formula (I) wherein

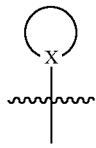

is selected from the group consisting of phenyl, 3-(trifluoromethyl)-phenyl, 4-(trifluoromethyl)-phenyl, 4-methoxyphenyl, 1-(t-butoxycarbonyl)-piperidin-4-yl, 1-(trifluoromethyl-sulfonyl)-piperidin-4-yl, 1-(trifluoromethyl-sulfonyl)-pyrrolidin-3-yl, 1-(phenyl-sulfonyl)-piperidin-4-yl, 1-((3-carboxy-phenyl)-sulfonyl)-piperidin-4-yl, 1-((4-carboxy-thien-2-yl)-sulfonyl)-piperidin-4-yl, and 1-(phenyl-amino)-piperidin-1-yl.

In another embodiment, the present invention is directed to compounds of formula (I) wherein

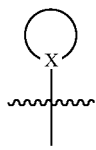

is selected from the group consisting of phenyl, 3-(trifluoromethyl)-phenyl, 4-(trifluoro-methyl)-phenyl, 1-(trifluoro-methyl-sulfonyl)-piperidin-4-yl, 1-(trifluoro-methyl-sulfonyl)-pyrrolidin-3-yl, 1-(phenyl-sulfonyl)-piperidin-4-yl, 1-(4-carboxy-thien-2-yl)-sulfonyl)-piperidin-4-yl and 4-(phenyl-amino)-piperidin-1-yl.

In another embodiment, the present invention is directed to compounds of formula (I) wherein

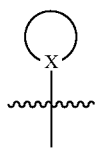

is selected from the group consisting of 3-(trifluoromethyl)-phenyl; 1-(trifluoromethyl-sulfonyl)-piperidin-4-yl and 1-((4-carboxy-thien-2-yl)-sulfonyl)-piperidin-4-yl.

In an embodiment, the present invention is directed to compounds of formula (I) wherein $R^3$ is selected from the group consisting of halogen, hydroxy, cyano, $C_{1-4}$alkyl, fluorinated $C_{1-4}$alkyl, hydroxy substituted $C_{1-1}$alkyl, $C_{1-4}$alkoxy, fluorinated $C_{1-2}$alkoxy, —$CO_2H$, —C(O)O—($C_{1-4}$alkyl), —$SO_2$—($C_{1-4}$alkyl) and —$SO_2$-(fluorinated $C_{1-2}$alkyl). In another embodiment, the present invention is directed to compounds of formula (I) wherein $R^3$ is selected from the group consisting of hydroxy, fluorinated $C_{1-2}$alkyl, $C_{1-2}$alkoxy and carboxy.

In another embodiment, the present invention is directed to compounds of formula (I) wherein $R^3$ is selected from the group consisting of hydroxy, trifluoromethyl, methoxy and carboxy.

In an embodiment, the present invention is directed to compounds of formula (I) wherein c is an integer from 0 to 1. In another embodiment, the present invention is directed to compounds of formula (I) wherein c is 1. In another embodiment, the present invention is directed to compounds of formula (I) wherein c is 0. In another embodiment, the present invention is directed to compounds of formula (I) wherein c is an integer from 1 to 2.

In an embodiment, the present invention is directed to compounds of formula (I) wherein each $R^4$ is independently selected from the group consisting of halogen, $C_{1-4}$alkyl, fluorinated $C_{1-2}$alkyl, $C_{1-4}$alkoxy and fluorinated $C_{1-2}$alkoxy. In another embodiment, the present invention is directed to compounds of formula (I) wherein each $R^4$ is independently selected from the group consisting of fluoro, chloro, bromo, methyl, ethyl, t-butyl, trifluoromethyl, methoxy, ethoxy, t-butoxy and trifluoromethoxy.

In an embodiment, the present invention is directed to compounds of formula (I) wherein $R^5$ is selected from the group consisting of —C(O)—($C_{1-2}$alkyl), —C(O)O—($C_{1-4}$alkyl), —$SO_2$—($C_{1-2}$alkyl) and —$SO_2$-(fluorinated $C_{1-2}$alkyl); and

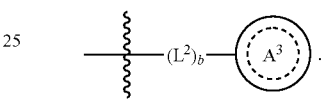

In another embodiment, the present invention is directed to compounds of formula (I) wherein $R^5$ is selected from the group consisting of —C(O)O—($C_{1-4}$alkyl), —$SO_2$-(fluorinated $C_{1-2}$alkyl) and

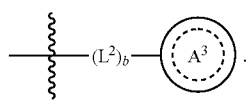

In another embodiment, the present invention is directed to compounds of formula (I) wherein $R^5$ is selected from the group consisting of t-butoxycarbonyl-, trifluoromethyl-sulfonyl- and

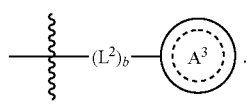

In another embodiment, the present invention is directed to compounds of formula (I) wherein $R^5$ is selected from the group consisting of t-butoxycarbonyl- and trifluoromethylsulfonyl-. In another embodiment, the present invention is directed to compounds of formula (I) wherein $R^5$ is

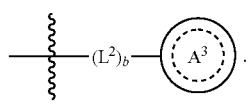

In an embodiment, the present invention is directed to compounds of formula (I) wherein $R^6$ is selected from the group consisting of $C_{1-4}$alkyl, fluorinated $C_{1-2}$alkyl, —C(O)—$NR^ER^F$, —$NR^E$—C(O)—($C_{1-4}$alkyl), —$NR^E$—$SO_2$—($C_{1-4}$alkyl), and

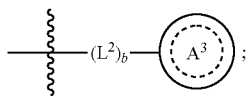

wherein $R^E$ and $R^F$ are each independently selected from the group consisting of hydrogen and methyl. In another embodiment, the present invention is directed to compounds of formula (I) wherein $R^6$ is

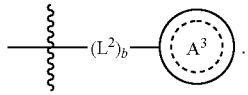

In an embodiment, the present invention is directed to compounds of formula (I) wherein b is 0. In another embodiment, the present invention is directed to compounds of formula (I) wherein b is 1.

In an embodiment, the present invention is directed to compounds of formula (I) wherein $L^2$ is selected from the group consisting of —$CH_2$—, —$CH_2CH_2$—, —NH—, —N($CH_3$)—, —C(O)— and —$SO_2$—. In another embodiment, the present invention is directed to compounds of formula (I) wherein $L^2$ is selected from the group consisting of —$CH_2$—, —$CH_2CH_2$—, —NH—, —C(O)— and —$SO_2$—.

In another embodiment, the present invention is directed to compounds of formula (I) wherein $L^2$ is selected from the group consisting of —$CH_2$— and —$CH_2CH_2$—. In another embodiment, the present invention is directed to compounds of formula (I) wherein $L^2$ is selected from the group consisting of —C(O)— and —$SO_2$—. In another embodiment, the present invention is directed to compounds of formula (I) wherein $L^2$ is —NH—.

In an embodiment, the present invention is directed to compounds of formula (I) wherein

is selected from the group consisting of phenyl, furan-2-yl, thien-2-yl; wherein the phenyl is optionally substituted with a substituent selected from the group consisting of halogen, hydroxy, cyano, $C_{1-4}$alkyl, fluorinated $C_{1-2}$alkyl, hydroxy substituted $C_{1-4}$alkyl, $C_{1-2}$alkoxy, fluorinated $C_{1-2}$alkoxy, —$CO_2H$, —C(O)O—($C_{1-4}$alkyl), —$SO_2$—($C_{1-4}$alkyl) and —$SO_2$-(fluorinated $C_{1-2}$alkyl); wherein the phenyl is further optionally substituted with one to two additional substituents independently selected from the group consisting of halogen, $C_{1-4}$alkyl, fluorinated $C_{1-2}$alkyl, $C_{1-4}$alkoxy and fluorinated $C_{1-2}$alkoxy; and wherein the furan-2-yl or thien-2-yl is optionally substituted with a substituent selected from the group consisting of halogen, $C_{1-4}$alkyl, fluorinated $C_{1-2}$alkyl, $C_{1-4}$alkoxy, fluorinated $C_{1-2}$alkoxy, —$CO_2H$, —C(O)O—($C_{1-4}$alkyl) and —C(O)—$NR^GR^H$; wherein $R^G$ and $R^H$ are each independently selected from the group consisting of hydrogen and methyl. In another embodiment, the present invention is directed to compounds of formula (I) wherein

is selected from the group consisting of phenyl, furan-2-yl and thien-2-yl; wherein the phenyl, furan-2-yl or thien-2-yl is optionally substituted with carboxy.

In an embodiment, the present invention is directed to a compound of formula (I) selected from the group consisting of 6-(bis(4-chlorophenyl)methyl)-N-(1-((trifluoromethyl)sulfonyl)piperidin-4-yl)cinnolin-4-amine (Compound #5);

6-(bis(4-chlorophenyl)methyl)-N-(3-(trifluoromethyl)benzyl)cinnolin-4-amine (Compound #8);

5-[4-([6-[bis(4-chlorophenyl)methyl]cinnolin-4-yl]amino)piperidine-1-sulfonyl]thiophene-3-carboxylic acid (Compound #32);

6-((4-chlorophenyl)(4-fluorophenyl)methyl)-N-(1-(trifluoromethylsulfonyl)piperidin-4-yl)cinnolin-4-amine (Compound #34);

6-((4-chlorophenyl)(thiazol-2-yl)methyl)-N-(1-(trifluoromethylsulfonyl)piperidin-4-yl)cinnolin-4-amine (Compound #36);

and stereoisomers, tautomers and pharmaceutically acceptable salts thereof.

Additional embodiments of the present invention, include those wherein the substituents selected for one or more of the variables defined herein (e.g. a, b, c, $R^1$, $R^2$, $R^3$, $R^4$, $R^5$, $R^6$, $L^1$, $L^2$,

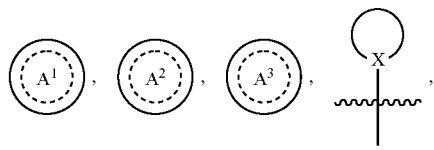

etc.) are independently selected to be any individual substituent or any subset of substituents selected from the complete list as defined herein.

In additional embodiments, the present invention is directed to any single compound or subset of compounds, independently selected from the representative compounds listed in Tables 1-2, below.

Representative compounds of the present invention are as listed in Tables 1-2, below. Unless otherwise noted, wherein a stereogenic center is present in the listed compound, the compound was prepared as a mixture of stereo-configurations.

TABLE 1

Representative Compounds of Formula (I)

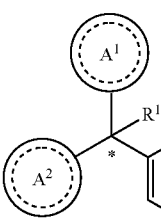

| ID No. | A¹ | A² | R¹ | —(L¹)ₐ— |  |
|---|---|---|---|---|---|
| 1 | 4-chlorophenyl | 4-chlorophenyl | —OH | —NH— | 1-(trifluoro-methyl-sulfonyl)-piperidin-4-yl |
| 2 | 4-chloro-phenyl | 4-chloro-phenyl | —OH | —NH— | 1-(t-butoxy-carbonyl)-piperidin-4-yl |
| 5 | 4-chloro-phenyl | 4-chloro-phenyl | H | —NH— | 1-(trifluoro-methyl-sulfonyl)-piperidin-4-yl |
| 6 | 4-chloro-phenyl | 4-chloro-phenyl | —OH | —NH—CH₂— | 3-(trifluoro-methyl)-phenyl |
| 7 | 4-chloro-phenyl | 4-chloro-phenyl | —OH | —NH—CH₂— | 4-(trifluoro-methyl)-phenyl |
| 8 | 4-chloro-phenyl | 4-chloro-phenyl | H | —NH—CH₂— | 3-(trifluoro-methyl)-phenyl |
| 9 | 4-chloro-phenyl | 4-chloro-phenyl | H | —NH—CH₂— | 4-(trifluoro-methyl)-phenyl |
| 20 | 4-chloro-phenyl | 4-chloro-phenyl | H | —NH—CH₂— | 4-methoxy-phenyl |
| 21 | 4-chloro-phenyl | 4-chloro-phenyl | H | —NH—CH₂— | 4-hydroxy-phenyl |
| 24 | 4-chloro-phenyl | 4-chloro-phenyl | H | a = 0 | 4-(trifluoro-methyl-sulfonyl)-piperazin-1-yl |
| 25 | 4-chloro-phenyl | 4-chloro-phenyl | H | —NH—CH₂CH₂— | phenyl |
| 26 | 4-chloro-phenyl | 4-chloro-phenyl | H | —NH— | 1-(trifluoro-methyl-sulfonyl)-pyrrolidin-3-yl |
| 33 | 4-fluoro-phenyl | 4-fluoro-phenyl | H | —NH— | 1-(trifluoro-methyl-sulfonyl)-piperidin-4-yl |
| 34 | 4-fluoro-phenyl | 4-chloro-phenyl | H | —NH— | 1-(trifluoro-methyl-sulfonyl)-piperidin-4-yl |
| 35 | 4-methoxy-phenyl | 4-chlorophenyl | H | —NH— | 1-(trifluoro-methyl-sulfonyl)-piperidin-4-yl |
| 36 | thiazol-2-yl | 4-chloro-phenyl | H | —NH— | 1-(trifluoro-methyl-sulfonyl)-piperidin-4-yl |
| 37 | 4-chloro-phenyl | 4-chloro-phenyl | H | —NH—CH₂CH₂— | 4-carboxy-phenyl |
| 38 | 4-chloro-phenyl | 4-chloro-phenyl | H | —NH—CH₂CH₂— | 3-carboxy-phenyl |

TABLE 2

Representative Compounds of Formula (I)

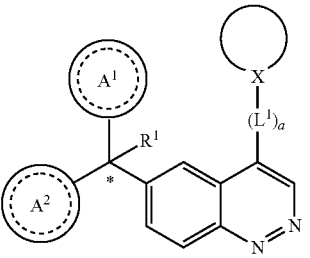

| ID No. | A¹ | A² | R¹ | —(L¹)ₐ— | 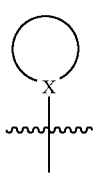 |
|---|---|---|---|---|---|
| 3 | 4-chloro-phenyl | 4-chloro-phenyl | H | —NH— | 1-(phenyl-carbonyl)-piperidin-4-yl |
| 4 | 4-chloro-phenyl | 4-chloro-phenyl | H | —NH— | 1-(phenyl-sulfonyl)-piperidin-4-yl |
| 10 | 4-chloro-phenyl | 4-chloro-phenyl | H | —NH— | 1-((4-carboxy-phenyl)-sulfonyl)-piperidin-4-yl |
| 11 | 4-chloro-phenyl | 4-chloro-phenyl | H | —NH— | 1-((3-carboxy-phenyl)-sulfonyl)-piperidin-4-yl |
| 12 | 4-chloro-phenyl | 4-chloro-phenyl | H | —NH— | 1-((3-carboxy-phenyl)-CH₂)-piperidin-4-yl |
| 13 | 4-chloro-phenyl | 4-chloro-phenyl | H | —NH— | 1-((4-carboxy-phenyl)-CH₂)-piperidin-4-yl |
| 14 | 4-chloro-phenyl | 4-chloro-phenyl | H | —NH— | 1-((5-carboxy-furan-2-yl)-sulfonyl)-piperidin-4-yl |
| 15 | 4-chloro-phenyl | 4-chloro-phenyl | H | —NH— | 1-((5-carboxy-thien-2-yl)-CH₂)-piperidin-4-yl |
| 16 | 4-chloro-phenyl | 4-chloro-phenyl | H | —NH— | 1-((5-carboxy-thien-2-yl)-sulfonyl)-piperidin-4-yl |
| 17 | 4-chloro-phenyl | 4-chloro-phenyl | H | —NH— | 1-(4-carboxy-phenyl)-piperidin-4-yl |
| 18 | 4-chloro-phenyl | 4-chloro-phenyl | H | —NH— | 1-((2-carboxy-phenyl)-CH₂)-piperidin-4-yl |
| 19 | 4-chloro-phenyl | 4-chloro-phenyl | H | —NH— | 1-((2-carboxy-phenyl)-sulfonyl)-piperidin-4-yl |
| 22 | 4-chloro-phenyl | 4-chloro-phenyl | H | a = 0 | 4-(phenyl-CH₂)-piperazin-1-yl |
| 23 | 4-chloro-phenyl | 4-chloro-phenyl | H | —NH— | 1-((3-carboxy-phenyl)-CH₂CH₂)-piperidin-4-yl |
| 27 | 4-chloro-phenyl | 4-chloro-phenyl | H | —NH— | 1-(phenyl-sulfonyl)-pyrrolidin-3-yl |
| 28 | 4-chloro-phenyl | 4-chloro-phenyl | H | —NH— | 1-(phenyl-CH₂-pyrrolidin-3-yl |
| 29 | 4-chloro-phenyl | 4-chloro-phenyl | H | a = 0 | 4-(phenyl-NH)-piperidin-1-yl |
| 30 | 4-chloro-phenyl | 4-chloro-phenyl | H | —NH— | 1-(phenyl-CH₂CH₂)-piperidin-4-yl |
| 31 | 4-chloro-phenyl | 4-chloro-phenyl | H | —NH— | 1-(4-carboxy-phenyl)-CH₂CH₂)-piperidin-4-yl |
| 32 | 4-chloro-phenyl | 4-chloro-phenyl | H | —NH— | 1-(4-carboxy-thien-2-yl)-sulfonyl)-piperidin-4-yl |

Definitions

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$alkyl" shall mean any straight or branched chain composition of between 1 and 4 carbon atoms.

Further, one skilled in the art will recognize that the term "—($C_{X-Y}$alkyl)-" shall denote any $C_{X-Y}$alkyl straight or branched chain composition as defined above, wherein said $C_{X-Y}$alkyl straight or branched chain composition is divalent and is therefore bound through two points of attachment, preferably through two terminal carbon atoms.

As used herein, unless otherwise noted, the term "halogenated $C_{X-Y}$alkyl" wherein X and Y are integers, shall mean any $C_{X-Y}$alkyl group as defined above substituted with at least one halogen atom, preferably substituted with a least one fluoro atom. For example, the term "halogenated $C_{1-4}$alkyl" shall mean any $C_{1-4}$alkyl group as defined above substituted with at least one halogen atom, preferably substituted with at least one fluoro atom. Suitable examples of "halogenated $C_{1-4}$alkyl" include but are not limited to —$CH_2F$, —$CH_2I$, —$CH_2Br$, —$CH_2Cl$, —$CF_3$, —$CCl_3$, —$CH_2$—$CF_3$, —$CH_2$—$CCl_3$, —$CF_2$—$CF_2$—$CF_2$—$CF_3$, and the like.

Similarly, the term "fluorinated $C_{X-Y}$alkyl" wherein X and Y are integers, shall mean any $C_{X-Y}$alkyl group as defined above substituted with at least one fluoro atom, preferably one to three fluoro atoms. For example, the term "fluorinated $C_{1-24}$alkyl" shall mean any $C_{1-4}$alkyl group as defined above substituted with at least one fluoro atom, preferably one to three fluoro atoms. Suitable examples of "fluorinated $C_{1-4}$alkyl" include but are not limited to —$CF_3$, —$CH_2$—$CF_3$, —$CF_2$—$CF_2$—$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched carbon chain composition of between X and Y carbon atoms. For example, "$C_{1-4}$alkoxy" shall mean any oxygen ether radical of the above described straight or branched chain composition of between 1 and 4 carbon atoms.

As used herein, unless otherwise noted, the term "halogenated $C_{X-Y}$alkoxy" wherein X and Y are integers, shall mean any $C_{X-Y}$alkoxy group as defined above substituted with at least one halogen atom, preferably substituted with a least one fluoro atom. For example, the term "halogenated $C_{1-4}$alkoxy" shall mean any $C_{1-4}$alkoxy group as defined above substituted with at least one halogen atom, preferably substituted with a least one fluoro atom. Suitable examples of "halogenated $C_{1-4}$alkoxy" include but are not limited to —$OCH_2F$, —$OCH_2I$, —$OCH_2Br$, —$OCH_2Cl$, —$OCF_3$, —$OCCl3$, —$OCH_2$—$CF_3$, —$OCH_2$—$CCl_3$, —$OCF_2$—$CF_2$—$CF_2$—$CF_3$, and the like.

Similarly, the term "fluorinated $C_{X-Y}$alkoxy" wherein X and Y are integers shall mean any $C_{X-Y}$alkoxy group as defined above substituted with at least one fluoro atom, preferably one to three fluoro atoms. For example, the term "fluorinated $C_{1-4}$alkoxy" shall mean any $C_{1-4}$alkoxy group as defined above substituted with at least one halogen atom, preferably substituted with a least one fluoro atom. Suitable examples of "fluorinated $C_{1-4}$alkoxy" include but are not limited to —$OCF_3$, —$OCH_2$—$CF_3$, —$OCF_2$—$CF_2$—$CF_3$, and the like.

When a particular group is "substituted" (e.g., alkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

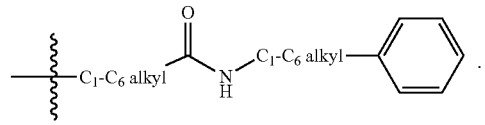

Abbreviations used in the specification, particularly the Schemes and Examples, are as follows:
AcOH=Acetic acid
aq.=Aqueous
BINAP=(2,2'-Bis(diphenylphosphino)-1,1'-binaphthyl)
Boc or BOC=tert-butoxycarbonyl
BSA=Bovine Serum Albumin
cAMP=Cyclic Adenosine Monophosphate
CB1 or CB1R or CB1R=Cannabanoid 1 Receptor
CB2 or CB2R or CB2R=Cannabanoid 2 Receptor
CBz of Cbz=Carboxybenzyl
conc.=Concentrated
DCC=N,N'-Dicyclohexylcarbodiimide
DCE=1,1-Dichloroethane
DCM=Dichloromethane
DIPEA or DIEA or Hunig's=Diisopropylethylamine Base
DME=Dimethoxyethane
DMEM=Dulbecco's Modified Eagle Medium
DMF=N,N-Dimethylformamide
DMSO=Dimethylsulfoxide
dppf=1,1'-Bis(diphenylphosphino)ferrocene
EDCI=1-Ethyl-3-(3-dimethylaminopropyl)carbodiimide
EtOAc or EA=Ethyl acetate
EtOH=Ethanol
Et$_3$SiH=Triethylsilane
FBS=Fetal Bovine Serum GCMS or GC-MS=Gas Chromatography-Mass Spectroscopy
GPCR=G-coupled Receptor
HATU=O-(7-Azabenzotriazol-1-yl)-N,N,N",N"-Tetramethyl Uronium Hexafluorophosphate
HBSS=Hank's Balanced Salt Solution
HBTU=N N,N,N',N'-Tetramethyl-O-(1H-benzotriazol-1-yl)uronium hexafluorophosphate
HDL=High Density Lipoprotein
HEPES=4-(2-Hydroxyethyl)-1-Piperazine Ethane Sulfonic Acid
HEX=Hexanes
HPLC=High Performance Liquid Chromatography
IPA or i-PrOH=Isopropyl alcohol
KHMDS=Potassium bis(trimethylsilyl)amide
KOt-Bu or KOtBu=Potassium t-butoxide
LADA=Latent Autoimmune Diabetes of Adults
LCMS or LC-MS=Liquid Cromatography-Mass Spectrometry
LDL=Low Density Lipoprotein
LiHMDS or LiN(SiMe$_3$)$_2$=Lithium bis(trimethylsilyl)amide
MeOH=Methanol
Mesyl=Methylsulfonyl
MTBE=Methyl t-butyl ether
n-BuLi=n-Butyl Lithium
NaBH(OAc)$_3$=Sodium triacetoxyborohydride
NaHMDS or NaN(SiMe$_3$)$_2$=Sodium bis(trimethylsilyl)amide
NASH=NonAlcoholic Steatohepatitis
NMR=Nuclear magnetic Resonance
NSB=Non-Specific Binding
PBS=Phosphate Buffered Saline
Pd$_2$(OAc)$_2$=Palladium(II)acetate
Pd$_2$(dba)$_3$=Tris(dibenzylidene acetone)dipalladium(0)
PE=Petroleum Ether
sat.=Saturated
sec-BuLi=sec-Butyl lithium
t-BuLi=tert-Butyl lithium
TEA=Triethylamine
TFA=Trifluoroacetic Acid
THF=Tetrahydrofuran
TLC=Thin Layer Chromatography
Tosyl=p-Toluenesulfonyl
Tris HCl or Tris-Cl=Tris[hydroxymethyl]aminomethyl hydrochloride
XantPhos=4,5-Bis(diphenylphosphino)-9,9-dimethylxanthene
XPhos=2-Dicyclohexylphosphino-2',4',6'-triisopropylbiphenyl The compounds of the present invention are CB-1 inverse agonists useful for the treatment and/or prevention of metabolic disorders, including obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain. Preferably, the metabolic disorder is selected from the group consisting of obesity, Type II diabetes, and dyslipidemias. More preferably, the metabolic disorder is obesity or Type II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of one or more additional symptoms; and/or (d) delay or avoidance of the development or progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named. One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

One skilled in the art will recognize that during any of the processes for preparation of the compounds of the present invention, as herein described In more detail, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($R$moles−$S$moles)/($R$moles+$S$moles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee$=([α-obs]/[α-max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

General Synthetic Schemes:

In the preparation of the compounds of the present invention, the

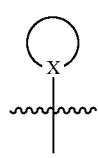

substituent group may be incorporated into the compounds of formula (I) by coupling the substituent group in a single step or alternatively, by incorporated the substituent group via two or more coupling steps, each of which steps incorporates a portion of the complete substituent group. For completeness and clarity, in the general synthetic schemes which follow herein, the

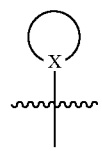

substituent group shall be represented as

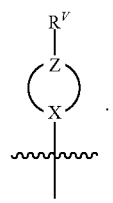

Thus, in the general synthetic schemes which follow herein, (a) wherein

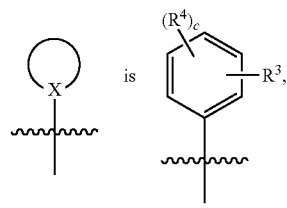

then

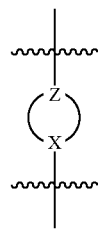

represents

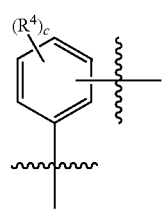

(wherein X and Z are each C), and $R^V$ represents $R^3$;

(b) wherein
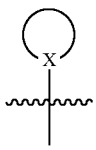
is selected from the group consisting of
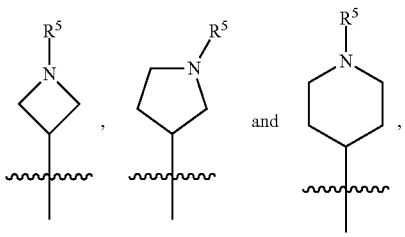
then
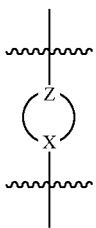
represents
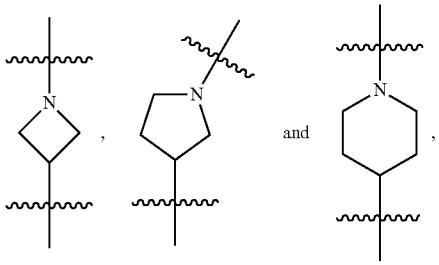 [SMILES: *C1CN(*)C1 ; *C1CCN(*)C1 ; *C1CCN(*)CC1]
respectively (wherein X is C and Z is N); and $R^V$ represents $R^5$;
(c) wherein
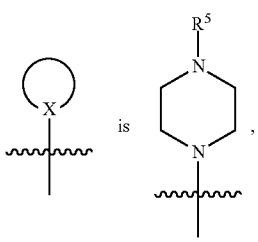 is 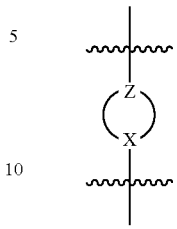,
then
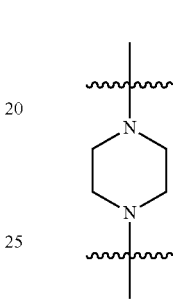
represents
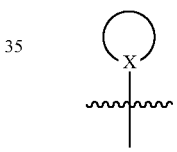
(wherein X and Z are each N), and $R^V$ represent $R^5$;
and (d) wherein
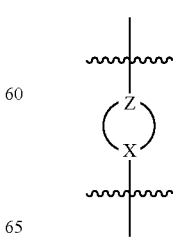
is selected from the group consisting of
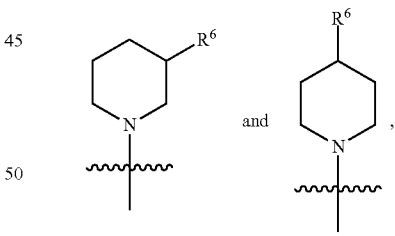
then
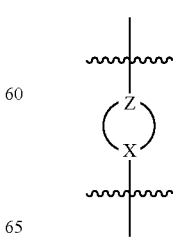

represents
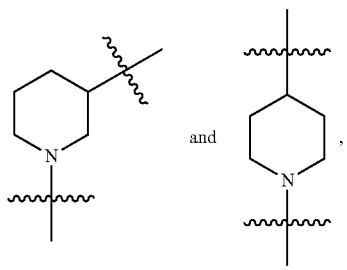 [SMILES: *C1CCCN(*)C1 ; *C1CCN(*)CC1]
respectively (wherein X is N and Z is C), and $R^V$ represent $R^6$.
Compounds of formula (I) wherein
is an optionally substituted phenyl, wherein
is an optionally substituted phenyl and wherein
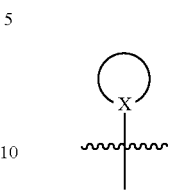
is selected from the group consisting of
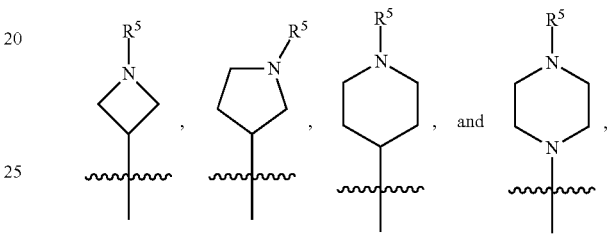
may be prepared according to the process outlined in Scheme 1.
Scheme 1
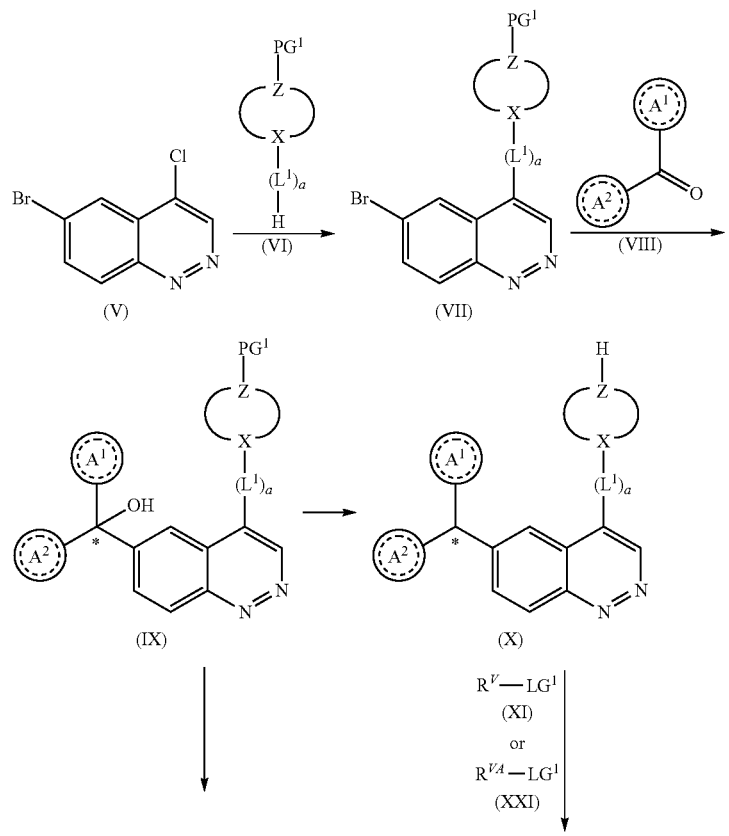

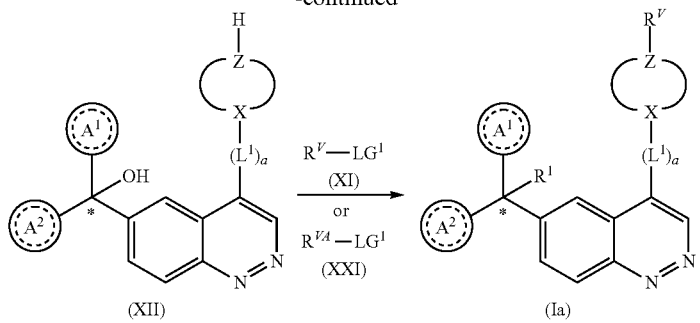

Accordingly, a suitably substituted compound of formula (V), a known compound or compound prepared by known methods, is reacted with a suitably substituted compound of formula (VI), wherein $PG^1$ is a suitably selected nitrogen-bound protecting group such as Boc, Cbz, and the like, preferably Boc; in the presence of a suitably selected base such as TEA, DIPEA, pyridine, and the like; in a suitably selected organic solvent such as IPA, MeOH, EtOH, and the like; preferably at a temperature in the range of from about room temperature to about 100° C., more preferably at a temperature in the range of from about 75° C. to about 90° C.; to yield the corresponding compound of formula (VII).

The compound of formula (VII) is reacted first with a suitably substituted alkyl lithium reagent such as n-BuLi, sec-BuLi, t-BuLi, and the like; and then reacted with a suitably substituted compound of formula (VIII), a known compound or compound prepared by known methods; in a suitably selected organic solvent such as THF, diethyl ether, and the like; to yield the corresponding compound of formula (IX). Wherein the compound of formula (VII), -$(L^1)_a$- is —NH—, then the compound of formula (VII) is first reacted with a suitably selected base such as KHMDS, LiHMDS, NaHMDS, NaH, and the like; prior to reacting with the suitably selected alkyl lithium reagent and the compound of formula (VIII); to yield the corresponding compound of formula (IX).

The compound of formula (IX) is reacted to remove the $R^1$ hydroxy group, according to known methods, for example by reacting with $Et_3SiH$ in TFA; to yield the corresponding compound of formula (X). One skilled in the art will recognize that under said reaction conditions, the $PG^1$ protecting group on the compound of formula (X) may be simultaneously removed.

The compound of formula (X) is reacted with a suitably selected compound of formula (XI), wherein $LG^1$ is a suitably selected group such as chloro, bromo, iodo, mesylate, triflate, tosylate, and the like, according to known methods as would be readily recognized by those skilled in the art, to yield the corresponding compound of formula (Ia) wherein $R^1$ is hydrogen. Alternatively, the compound of formula (X) is reacted with a suitably substituted compound of formula (XI), wherein $R^V$-$LG^1$ is a suitably substituted carbonyl or sulfonyl anhydride, according to known methods as would be readily recognized by those skilled in the art, to yield the corresponding compound of formula (Ia) wherein $R^1$ is hydrogen.

Alternatively still, the compound of formula (X) is reacted with a suitably substituted compound of formula (XXI), wherein $R^{VA}$ corresponds to $R^V$ minus any component of $R^V$ which is incorporated into the final compound from the $LG^1$ group. For example, wherein $R^V$ corresponds to

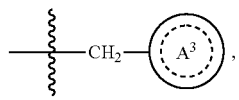

then (as detailed below), the $R^V$ group is incorporated into the final compound by reacting the compound of formula (X) with a compound of formula (XXI) wherein $R^{VA}$ is $$\text{—}\!\!\!\!\!\!\!\!\xi\text{—} \boxed{A^3}$$

and $LG^1$ is —C(O)H, such that the —$CH_2$— portion is introduced into the final compound through the $LG^1$ group.

In an example, the compound of formula (X) is reacted with a suitably substituted compound of formula (XI), wherein $LG^1$ is a suitably selected leaving group such as chloro, bromo, iodo, tosylate, mesylate, and the like; in the presence of a suitably selected base such as TEA, Hunig's base, $Na_2CO_3$, and the like; in a suitably selected solvent such as DMF, acetonitrile, DCM, and the like; to yield the corresponding compound of formula (Ia). Said reaction is preferred in the preparation of compounds of formula (Ia) wherein $R^V$ is bound to the Z atom on the compound of formula (Ia) via a —$CH_2$— or —$CH_2CH_2$— group.

In another example, wherein $R^V$ is bound to the rest of the compound of formula (Ia) through a —$CH_2$— group, the compound of formula (X) is reacted with a suitably substituted compound of formula (XXI), wherein $LG^1$ is —C(O)H and wherein $R^{VA}$ is $R^V$ minus the —$CH_2$— group; in the presence of a suitably selected reducing agent such as $NaCNBH_3$, sodium triacetoxyborohydride, and the like; in a suitably selected organic solvent such as DCE, methanol, ethanol, and the like; to yield the corresponding compound of formula (Ia). Said reaction is preferred for the preparation of compounds of formula (Ia) wherein $R^V$ is bound to the Z atom on the compound of formula (Ia) through a —$CH_2$— group. One skilled in the art will recognize that for said compounds, $R^V$ corresponds to —$CH_2$—$R^{VA}$; wherein $LG^1$ provides the —$CH_2$— portion of $R^V$.

In another example, the compound of formula (X) is reacted with a suitably substituted compound of formula (XI) wherein $LG^1$ is for example, Cl; in the presence of a suitably selected tertiary organic base such as TEA, Hunig's base, and the like; in a suitably selected solvent such as DCM, THF, and the like; to yield the corresponding compound of formula (Ia). Said coupling is preferred for the preparation of compounds of formula (Ia) wherein $R^V$ is bound to the Z atom on the compound of formula (Ia) via —C(O)— or —SO$_2$—. In a particular example, wherein $R^V$ is CF$_3$—SO$_2$—, the compound of formula (X) is reacted with triflic anhydride, a known compound, in the presence of TEA, in methylene chloride; to yield the corresponding compound of formula (Ia)

In another example, the compound of formula (X) is reacted with a suitably substituted compound of formula (XI) wherein LG$^1$ is —OH; in the presence of a suitably selected peptide coupling agent such as DCC, HATU, HBTU, EDCI, and the like; optionally in the presence of a suitably selected base such as Hunig's base, TEA, and the like; in a suitably selected solvent such as DMF, DCM, and the like; to yield the corresponding compound of formula (Ia). Said coupling is preferred for the preparation of compounds of formula (Ia) wherein $R^V$ is bound to the Z atom on the compound of formula (Ia) via —C(O)—.

In another example, the compound of formula (X) is reacted with a suitably substituted compound of formula (XI) wherein LG$^1$ is a suitably selected group such as Cl, Br, I, triflate, and the like; in the presence of a suitably selected catalyst such as Pd$_2$(dba)$_3$, Pd(OAc)$_2$, and the like; in the presence of a suitably selected ligand such as BINAP, dppf, XantPhos, XPhos, and the like; in the presence of a suitably selected base such as Cs$_2$CO$_3$, K$_2$CO$_3$, K$_3$PO$_4$, and the like; in a suitably selected organic solvent such as 1,4-dioxane, toluene, THF, DME, and the like; to yield the corresponding compound of formula (Ia). Said coupling is preferred for the preparation of compounds of formula (Ia) wherein, for example, $R^V$ is

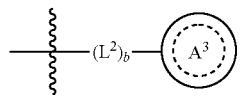

and wherein b is 0 (L$^2$ is absent).

In another example, the compound of formula (X) is reacted with a suitably substituted compound of formula (XI), wherein LG$^1$ is a suitably selected group such as Cl, Br, I, mesylate, tosylate, and the like; in the presence of a suitably selected base such as TEA, Hunig's base, Na$_2$CO$_3$, and the like; in a suitably selected solvent such as DMF, acetonitrile, DCM, and the like; to yield the corresponding compound of formula (Ia). Said coupling is preferred for the preparation of compounds of formula (Ia) wherein, for example, $R^V$ is

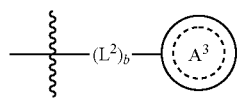

and wherein b is 1 and L$^2$ is CH$_2$.

Alternatively, the compound of formula (IX) is de-protected, under conditions which will not remove the R$^1$ hydroxy group, as would be readily recognized by one skilled in the art, for example, by reacting with a suitably selected acid such as TFA or 4M HCl in 1,4-dioxane; to yield the corresponding compound of formula (XII).

The compound of formula (XII) is reacted with a suitably selected compound of formula (XI), wherein LG$^1$ is a suitably selected group such as chloro, bromo, iodo, mesylate, triflate, tosylate and the like, according to known methods as would be readily recognized by those skilled in the art (for example as described in the reaction of the compound of formula (X) with the compound of formula (XI) above), to yield the corresponding compound of formula (Ia) wherein R$^1$ is hydroxy. Alternatively, the compound of formula (XII) is reacted with a suitably substituted compound of formula (XI), wherein R$^V$-LG$^1$ is a suitably selected carbonyl or sulfonyl anhydride, according to known methods as would be readily recognized by those skilled in the art; to yield the corresponding compound of formula (Ia) wherein R$^1$ is hydroxy.

Compounds of formula (I) wherein

is an optionally substituted phenyl and wherein

is an optionally substituted phenyl may be prepared according to the process as outlined in Scheme 2, below.

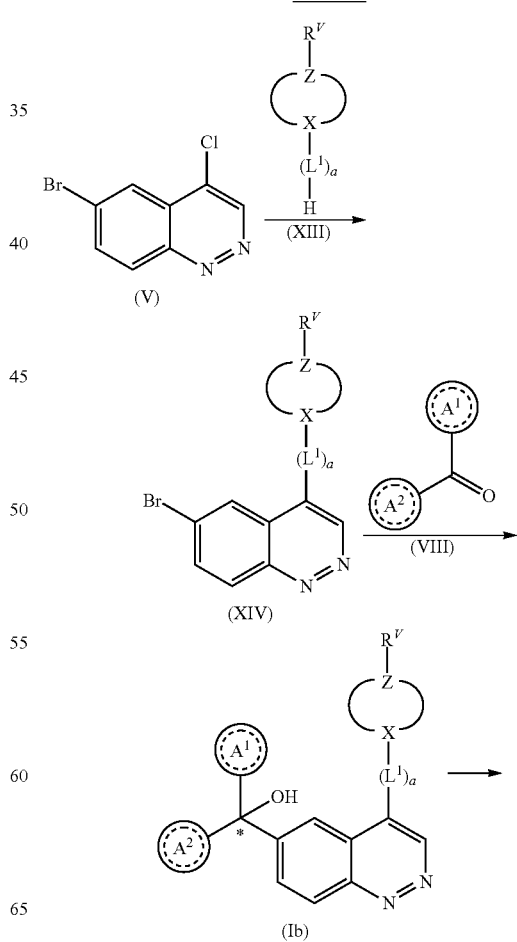

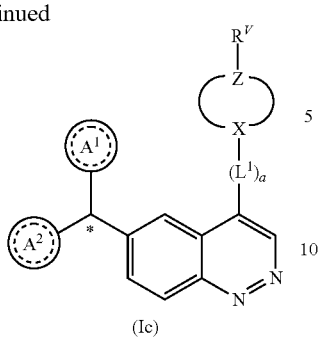

(Ic)

Accordingly, a suitably substituted compound of formula (V), a known compound or compound prepared by known methods, is reacted with a suitably substituted compound of formula (XIII); in the presence of a suitably selected base such as TEA, DIPEA, pyridine, and the like; in a suitably selected organic solvent such as IPA, MeOH, EtOH, and the like; preferably at a temperature in the range of from about room temperature to about 100° C., more preferably at a temperature in the range of from about 75° C. to about 90° C.; to yield the corresponding compound of formula (XIV).

The compound of formula (XIV) is reacted first with a suitably substituted alkyl lithium reagent such as n-BuLi, sec-BuLi, t-BuLi, and the like; and then reacted with a suitably substituted compound of formula (VIII), a known compound or compound prepared by known methods; in a suitably selected organic solvent such as THF, diethyl ether, and the like; to yield the corresponding compound of formula (Ib). Wherein the compound of formula (XIV), -(L$^1$)$_a$- is —NH—, then the compound of formula (XIV) is first reacted with a suitably selected base such as KHMDS, LiHMDS, NaHMDS, NaH, and the like; prior to reacting with the suitably selected alkyl lithium reagent and the compound of formula (VIII); to yield the corresponding compound of formula (Ib).

The compound of formula (Ib) is further optionally reacted according to known methods, for example with Et$_3$SiH in TFA; to yield the corresponding compound of formula (Ic).

Compounds of formula (I) wherein one or both of

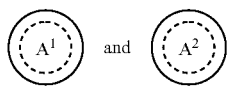

are other than an optionally substituted phenyl, may be prepared according to the process outlined in Scheme 3, below.

Scheme 3

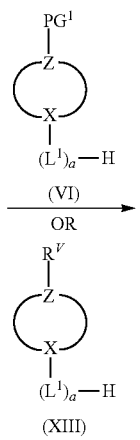

(V)    (VI)
       OR
       (XIII)

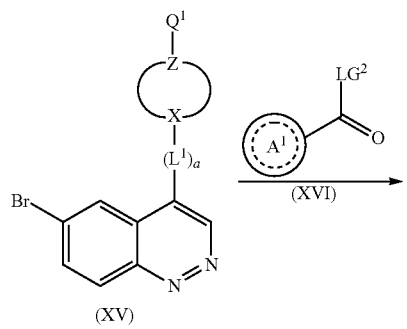

(XV)    (XVI)

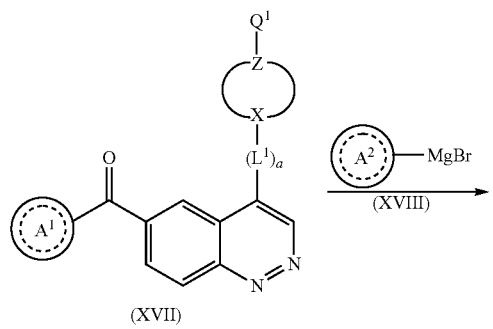

(XVII)    (XVIII)

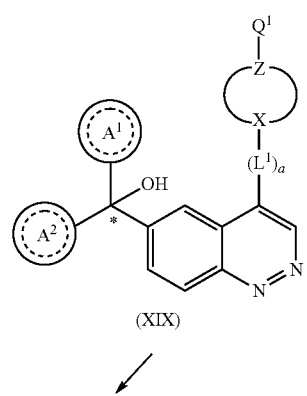

(XIX)

-continued

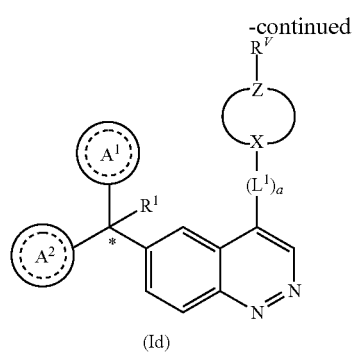

(Id)

Accordingly, a suitably substituted compound of formula (V), a known compound or compound prepared by known methods, is reacted with a suitably substituted compound of formula (VI), a known compound or compound prepared by known methods or with a suitably substituted compound of formula (XIII), a known compound or compound prepared by known methods, as described in Schemes 1 and 2 above, to yield the corresponding compound of formula (XV), wherein $Q^1$ is $R^V$ or a suitably selected nitrogen protecting group.

The compound of formula (XV) is reacted with a suitably selected alkyl lithium reagent such as n-BuLi, sec-BuLi, t-BuLi, and the like; and then reacted with a suitably substituted compound of formula (XVI), wherein $LG^2$ is a suitably selected leaving group such as methoxymethylamino, and the like; in a suitably selected solvent such as THF, diethylether, and the like; to yield the corresponding compound of formula (XVII). Wherein the compound of formula (XV), $-(L^1)_a-$ is —NH—, then the compound of formula (XV) is first reacted with a suitably selected base such as KHMDS, LiHMDS, NaHMDS, and the like; prior to reacting with the suitably selected alkyl lithium reagent and the compound of formula (XVI).

The compound of formula (XVII) is reacted with a suitably substituted compound of formula (XVIII), under anhydrous conditions, in a suitably selected organic solvent such as THF, diethyl ether, and the like; at a temperature in the range of from about −20° C. to about 0° C.; to yield the corresponding compound of formula (XIX).

The compound of formula (XIX) is then further, optionally reacted as herein described, to yield the desired compound of formula (Id), wherein one or both of

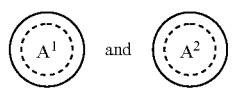

are other than an optionally substituted phenyl. For example, wherein $Q^1$ is $R^V$, the compound of formula (XIX) corresponds to a compound of formula (I) wherein $R^1$ is hydroxy. Said compound may be optionally reacted, as herein described to remove the hydroxy group. Alternatively, wherein $Q^1$ is a suitably selected protecting group, the compound of formula (XIX) may be substituted for the compound of formula (IX), in Scheme 1, and reacted as described in Scheme 1, to yield the desired compound of formula (I).

Compounds of formula (I) wherein $R^6$ is

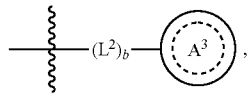

b is 1 and $L^2$ is selected from the group consisting of —NH— and —N(CH$_3$)— may be prepared according to the process as described in Scheme 4, below, Scheme 4

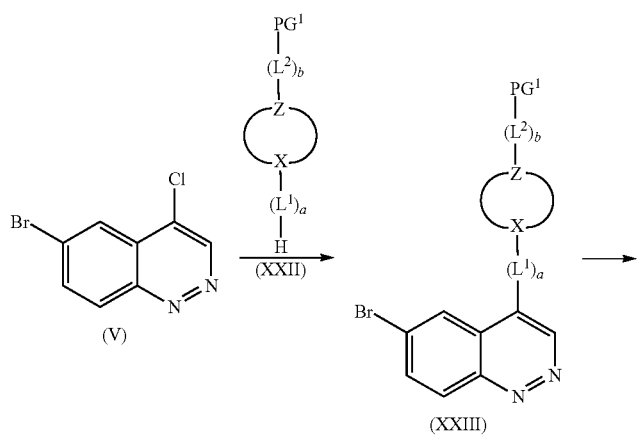

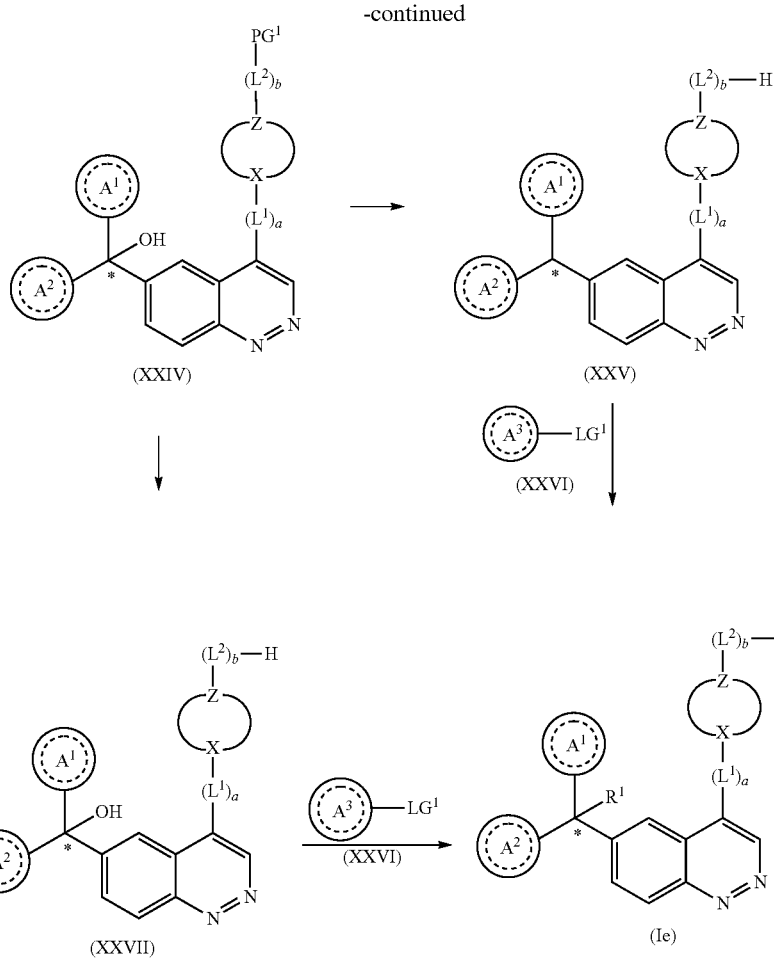

Accordingly, a suitably substituted compound of formula (V) is reacted with a suitably substituted compound of formula (XXII), wherein -(L$_2$)$_b$- is selected from the group consisting of —NH— and —N(CH$_3$)—; and wherein PG$^1$ is a suitably selected nitrogen-bound protecting group such as Boc, Cbz, and the like, preferably Boc; in the presence of a suitably selected base such as TEA, DIPEA, pyridine, and the like; in a suitably selected organic solvent such as IPA, MeOH, EtOH, and the like; preferably at a temperature in the range of from about room temperature to about 100° C., more preferably at a temperature in the range of from about 75° C. to about 90° C.; to yield the corresponding compound of formula (XXIII).

The compound of formula (XXIII) is then reacted to yield the corresponding compound of formula (XXIV). More particularly, the compound of formula (XXIII) may be substituted for the compound of formula (VII) in Scheme 1, and reacted with a suitably substituted compound of formula (VIII), as described in Scheme 1, to yield the corresponding compound of formula (XXIV). Alternatively, the compound of formula (XXIII) may be substituted for the compound of formula (XV) in Scheme 3, and reacted sequential with a suitably substituted compound of formula (XVI) and a suitably substituted compound of formula (XVIII), as described in Scheme 3, to yield the corresponding compound of formula (XXIV).

The compound of formula (XXIV) is de-protected according to known methods, for example as described in Scheme 1 above, to yield the corresponding compound of formula (XXV) or the corresponding compound of formula (XXVII).

The compound of formula (XXV) or the compound of formula (XXVII) is then reacted with a suitably substituted compound of formula (XXVI), wherein LG$^1$ is a suitably selected halide such as bromo, chloro or iodo; in the presence of a suitably selected catalyst such as Pd$_2$(dba)$_3$, Pd(OAc)$_2$, and the like; in the presence of a suitably selected ligand such as BINAP, dppf, XantPhos, XPhos, and the like; in the presence of a suitably selected base such as Cs$_2$CO$_3$, K$_2$CO$_3$, K$_3$PO$_4$, and the like; in a suitably selected organic solvent such as 1,4-dioxane, toluene, THF, DME, and the like; (e.g. under Buchwald animation conditions); to yield the corresponding compound of formula (Ie).

Compounds of formula (XIII) wherein R$^V$ is

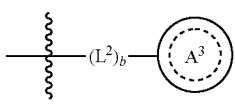

b is 1 and L$^2$ is selected from the group consisting of —NH— and —N(CH$_3$)— may prepared according to the procedure as described in Scheme 5 below.

Scheme 5

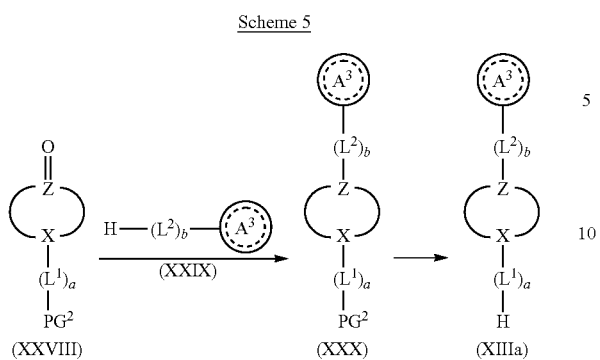

Accordingly, a suitably substituted compound of formula (XXVIII), wherein PG$^2$ is a suitably selected protecting group, and wherein Z is carbon, a known compound or compound prepared by known methods, is reacted with a suitably substituted compound of formula (XXIX), a known compound or compound prepared by known methods; in the presence of a suitably selected reducing agent such as Na(OAc)$_3$BH, NaBH$_3$CN, NaBH$_4$, and the like; in a suitably selected solvent, such as acetic acid/DCM, acetic acid/DCE, and the like; to yield the corresponding compound of formula (XXX). The compound of formula (XXX) is then de-protected according to known methods, to yield the corresponding compound of formula (XIIIa).

Compounds of formula (I) wherein R$^6$ is

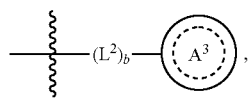

b is 1 and L$^2$ is selected from the group consisting of —NH— and —N(CH$_3$)— may be similarly prepared according to the process as outlined in Scheme 6, below.

Scheme 6

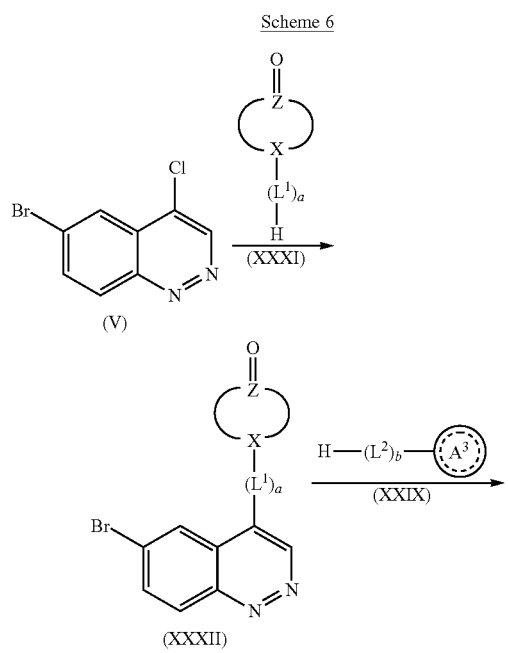

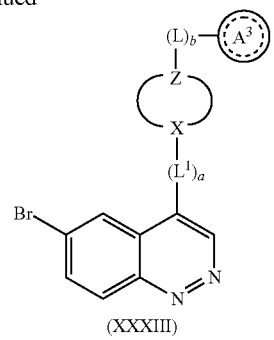

Accordingly, a suitably substituted compound of formula (V), a known compound or compound prepared by known methods is reacted with a suitably substituted compound of formula (XXXI), wherein Z is carbon, a known compound or compound prepared by known methods, in the presence of a suitably selected base such as TEA, DIPEA, pyridine, and the like; in a suitably selected organic solvent such as IPA, MeOH, EtOH, and the like; preferably at a temperature in the range of from about room temperature to about 100° C., more preferably at a temperature in the range of from about 75° C. to about 90° C.; to yield the corresponding compound of formula (XXXII).

The compound of formula (XXXII) is reacted with a suitably substituted compound of formula (XXIX), a known compound or compound prepared by known methods, in the presence of a suitably selected reducing agent such as Na(OAc)$_3$BH, NaBH$_3$CN, NaBH$_4$, and the like; in a suitably selected organic solvent such as acetic acid/DCM, acetic acid/DCE, and the like; to yield the corresponding compound of formula (XXXIII).

The compound of formula (XXXIII) is then further reacted as described herein, to yield the corresponding, desired compound of formula (I). For example, the compound of formula (XXXIII) may be substituted for the compound of formula (XIV) in Scheme 2 and reacted as described herein, to yield the desired, corresponding compound of formula (I). Alternatively, the compound of formula (XXXIII) may be substituted for the compound of formula (XV) in Scheme 3 and reacted as described herein.

One skilled in the art will recognize that in any of the processes described herein, the

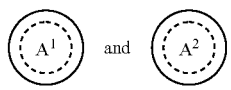

rings (as substituent groups or in reagents containing said substituent groups) may be interchanged, and the synthesis completed as described, to yield the corresponding desired compound.

One skilled in the art will further recognize that additional substitutions and/or substituent transformations (to yield the desired intermediates or compound(s) of the present invention) may be effected according to the procedures as described herein (in the general synthesis schemes and examples) or according to methods known to those skilled in the art.

Pharmaceutical Compositions and Methods of Treatment:

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.5 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may contain suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of metabolic disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.01 to about 50.0 mg/kg of body weight per day, or any amount or range therein. More preferably, from about 0.05 to about 15.0 mg/kg of body weight per day, or any amount or range therein. More preferably, from about 0.07 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Synthesis Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Synthesis Example 1

4-(4-(6-(bis(4-chlorophenyl)methyl)cinnolin-4-ylamino)piperidin-1-yl)benzoic acid Compound #17

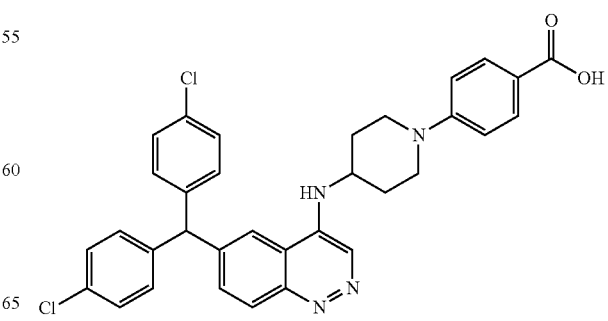

Step 1: Synthesis of tert-butyl 4-(6-bromocinnolin-4-ylamino)piperidine-1-carboxylate Into a 100-mL round-bottom flask, was placed a solution of 6-bromo-4-chlorocinnoline (2 g, 8.21 mmol, 1.00 equiv) in isopropanol (60 mL). To the resulting mixture was then added DIEA (2.15 mL, 1.50 equiv) dropwise with stirring. To the mixture was then added tert-butyl 4-aminopiperidine-1-carboxylate (4.9 g, 24.47 mmol, 3.00 equiv), in portions. The resulting solution was stirred overnight at 90° C. The reaction was then quenched by the addition of sat. sodium bicarbonate (100 mL). The resulting solution was extracted with of ethyl acetate (3×100 mL) and the organic layers combined, dried over anhydrous sodium sulfate and concentrated under vacuum. The resulting residue was applied onto a silica gel column with ethyl acetate to yield tert-butyl 4-[(6-bromocinnolin-4-yl)amino]piperidine-1-carboxylate as a yellow solid.

LC-MS (ES, m/z) 407 [M+H]$^+$

Step 2: Synthesis of tert-butyl 4-(6-(bis(4-chlorophenyl)(hydroxy)methyl)cinnolin-4-ylamino)piperidine-1-carboxylate Into a 250-mL 3-necked round-bottom flask purged and maintained with an inert atmosphere of nitrogen, was placed a solution of tert-butyl 4-[(6-bromocinnolin-4-yl)amino]piperidine-1-carboxylate (2.29 g, 5.62 mmol, 1.00 equiv) in tetrahydrofuran (84 mL). To the resulting mixture was then added of LiHMDS (8.45 mL, 1.50 equiv, 1M) dropwise with stirring at 0° C. The resulting solution was stirred for 20 min at 0° C. To the mixture was then added n-BuLi (14.08 mL, 4.00 equiv, 1.6M) dropwise with stirring at −78° C. The resulting solution was allowed to react, with stirring, for an additional 40 min at −78° C. To the mixture was added bis(4-chlorophenyl)methanone (5.65 g, 22.50 mmol, 4.00 equiv) dropwise with stirring at −78° C. The resulting solution was allowed to react, with stirring, for an additional 1 h at −78° C. The mixture was then warmed to 0° C. and stirred for 1 hour. The solution was then quenched by the addition of sat. NH$_4$Cl (200 mL). The resulting solution was extracted with ethyl acetate (2×100 mL) and the organic layers combined. The resulting solution was extracted with DCM (2×200 mL), the organic layers combined, dried over anhydrous sodium sulfate and concentrated under vacuum. The resulting residue was purified by re-crystallization from ethyl acetate to yield tert-butyl 4-([6-[bis(4-chlorophenyl)(hydroxy)methyl]cinnolin-4-yl]amino)piperidine-1-carboxylate as a yellow solid.

LC-MS (ES, m/z) 579 [M+H]$^+$

Step 3: Synthesis of 6-(bis(4-chlorophenyl)methyl)-N-(piperidin-4-yl)cinnolin-4-amine Into a 100-mL round-bottom flask purged and maintained with an inert atmosphere of nitrogen, was placed a solution of tert-butyl 4-([6-[bis(4-chlorophenyl)(hydroxy)methyl] cinnolin-4-yl]amino)piperidine-1-carboxylate (3.14 g, 5.42 mmol, 1.00 equiv) in dichloromethane (50 mL). To the resulting mixture was then added Et$_3$SiH (3.41 mL, 4.00 equiv) dropwise with stirring at 0° C. To the mixture was then added trifluoroacetic acid (10.4 mL, 25.00 equiv) dropwise with stirring at 0° C. The resulting solution was stirred for 3 h at room temperature. The reaction was then quenched by the addition of sat. sodium bicarbonate (100 mL). The resulting solution was extracted with DCM (2×100 mL) and the organic layers combined. The resulting solution was extracted with ethyl acetate (2×100 mL) and the organic layers combined, dried over anhydrous sodium sulfate and concentrated under vacuum. The resulting residue was re-crystallized from EA/PE in the ratio of 1:10 to yield 6-[bis (4-chlorophenyl)methyl]-N-(piperidin-4-yl)cinnolin-4-amine as a yellow solid.

LC-MS (ES, m/z) 463 [M+H]$^+$

Step 4: Synthesis of methyl 4-(4-(6-(bis(4-chlorophenyl)methyl)cinnolin-4-ylamino)piperidin-1-yl)benzoate Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (100 mg, 0.22 mmol, 1.00 equiv) in 1,4-dioxane (2 mL), methyl 4-bromobenzoate (56 mg, 0.26 mmol, 1.20 equiv), Pd(OAc)$_2$ (5.6 mg, 0.02 mmol, 0.11 equiv), BINAP (14.8 mg, 0.02 mmol, 0.11 equiv) and Cs$_2$CO$_3$ (110 mg, 0.34 mmol, 1.50 equiv). The resulting solution was stirred for 2 days at 105° C. The reaction was then quenched by the addition of sat. sodium bicarbonate (30 mL). The resulting solution was extracted with ethyl acetate (2×50 mL) and the organic layers combined, dried over anhydrous sodium sulfate and concentrated under vacuum. The resulting residue was applied onto a silica gel column with ethyl acetate too yield methyl 4-[4-([6-[bis(4-chlorophenyl)methyl]cinnolin-4-yl]amino)piperidin-1-yl]benzoate as a yellow solid.

LC-MS (ES, m/z) 597 [M+H]$^+$

Step 5: Synthesis of 4-(4-(6-(bis(4-chlorophenyl)methyl)cinnolin-4-ylamino)piperidin-1-yl)benzoic acid Into a 25-mL round-bottom flask, was placed methyl 4-[4-([6-[bis(4-chlorophenyl)methyl]cinnolin-4-yl]amino) piperidin-1-yl]benzoate (100 mg, 0.17 mmol, 1.00 equiv), sodium hydroxide (14 mg, 0.35 mmol, 2.00 equiv), methanol (3 mL), water (1 mL) and tetrahydrofuran (2 mL). The resulting solution was stirred overnight at 50° C. The resulting solution was diluted with water (20 mL). The pH value of the solution was adjusted to pH 1 with HCl (1 mol/L). The resulting solution was extracted with ethyl acetate (3×100 mL) and the organic layers combined, dried over anhydrous sodium sulfate and concentrated under vacuum. The resulting residue was purified by Prep-TLC with methanol/DCM ratio=1/4 as eluent to yield 4-[4-([6-[bis(4-chlorophenyl)methyl]cinnolin-4-yl]amino)piperidin-1-yl]benzoic acid as a yellow solid.

LC-MS (ES, m/z) 583 [M+H]$^+$ $^1$H-NMR (400 MHz, DMSO) δ 12.150 (br, 1H), 8.827 (s, 1H), 8.219 (s, 1H), 8.061 (d, J=8.8 Hz, 1H), 7.792-7.770 (m, 2H), 7.479 (d, J=8.8 Hz, 1H), 7.413-7.392 (m, 4H), 7.176-7.155 (m, 4H), 7.115-7.095 (m, 1H), 7.027-7.004 (m, 2H), 5.777 (s, 1H), 4.045-4.015 (m, 3H), 3.134-3.101 (m, 2H), 2.081-2.010 (m, 2H), 1.648-1.616 (m, 2H).

Synthesis Example 2

3-[[4-([6-[bis(4-chlorophenyl)methyl]cinnolin-4-yl]amino)piperidin-1-yl]methyl]benzoic acid Compound #12

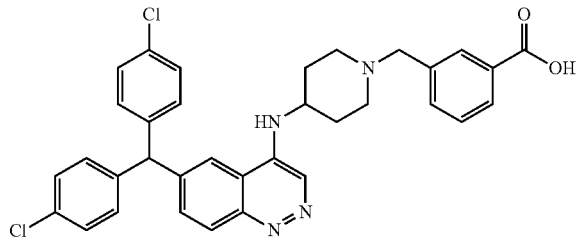 [SMILES: O=C(O)c1cccc(CN2CCC(Nc3cnnc4ccc(C(c5ccc(Cl)cc5)c5ccc(Cl)cc5)cc34)CC2)c1]

Step 1: Synthesis of methyl 3-((4-(6-(bis(4-chlorophenyl)methyl)cinnolin-4-ylamino)piperidin-1-yl)methyl)benzoate Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (100 mg, 0.22 mmol, 1.00 equiv) in N,N-dimethylformamide (10 mL), methyl 3-(bromomethyl)benzoate (50 mg, 0.22 mmol, 1.00 equiv) and potassium carbonate (61 mg, 0.44 mmol, 2.00 equiv). The resulting solution was stirred for 2 h at room temperature. The resulting solution was diluted with brine (50 mL). The resulting solution was extracted with ethyl acetate (2×50 mL) and the organic layers combined and concentrated under vacuum to yield methyl 3-[[4-([6-[bis(4-chlorophenyl)methyl]cinnolin-4-yl]amino)piperidin-1-yl]methyl]benzoate as yellow oil, which was used directly in the next step.

LC-MS (ES, m/z) 611 [M+H]+

Step 2: Synthesis of (4-tert-butoxyquinazolin-6-yl)(4-chlorophenyl)methanone Into a 25-mL round-bottom flask, was placed methyl 3-[[4-([6-[bis(4-chlorophenyl)methyl]cinnolin-4-yl]amino)piperidin-1-yl]methyl]benzoate (135 mg, 0.22 mmol, 1.00 equiv), sodium hydroxide (18 mg, 0.45 mmol, 2.00 equiv), methanol (3 mL), water (1 mL) and tetrahydrofuran (2 mL). The resulting solution was stirred overnight at 50° C. The pH value of the solution was adjusted to pH 2 with HCl (1 mol/L). The resulting solution was diluted with water (30 mL). The resulting solution was extracted with ethyl acetate (2×50 mL) and the organic layers combined, dried over anhydrous sodium sulfate and concentrated under vacuum. The resulting residue was purified by Prep-TLC with methanol/DCM ratio=1/1 as eluent to yield 3-[[4-([6-[bis(4-chlorophenyl)methyl]cinnolin-4-yl]amino)piperidin-1-yl]methyl]benzoic acid as a off-white solid.

LC-MS (ES, m/z) 597 [M+H]+

1H-NMR (300 MHz, DMSO) δ 8.666 (s, 1H), 8.201 (s, 1H), 8.000 (d, J=9.0 Hz, 1H), 7.894 (s, 1H), 7.806-7.780 (m, 1H), 7.528-7.352 (m, 7H), 7.150-7.122 (m, 4H), 7.044-7.034 (m, 1H), 5.753 (s, 1H), 3.692-3.665 (m, 1H), 3.544 (s, 2H), 2.834-2.795 (m, 2H), 2.227-2.180 (m, 2H), 1.943-1.911 (m, 2H), 1.662-1.594 (m, 2H).

Synthesis Example 3

4-((4-(6-(bis(4-chlorophenyl)methyl)cinnolin-4-ylamino)piperidin-1-yl)methyl)benzoic acid Compound #13

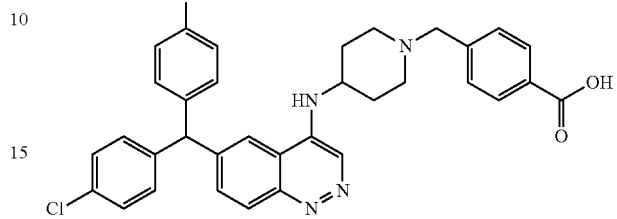

Step 1: Synthesis of methyl 4-((4-(6-(bis(4-chlorophenyl)methyl)cinnolin-4-ylamino)piperidin-1-yl)methyl) benzoate Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (100 mg, 0.22 mmol, 1.00 equiv) in N,N-dimethylformamide (10 mL), methyl 4-(bromomethyl)benzoate (50 mg, 0.22 mmol, 1.00 equiv) and potassium carbonate (61 mg, 0.44 mmol, 2.00 equiv). The resulting solution was stirred for 2 h at room temperature. The resulting solution was diluted with brine (50 mL). The resulting solution was extracted with ethyl acetate (2×50 mL) and the organic layers combined and concentrated under vacuum to yield methyl 4-[[4-([6-[bis(4-chlorophenyl)methyl]cinnolin-4-yl]amino)piperidin-1-yl]methyl]benzoate as a yellow solid, which was used for next step without further purification.

LC-MS (ES, m/z) 611 [M+H]+

Step 2: Synthesis of 4-((4-(6-(bis(4-chlorophenyl)methyl)cinnolin-4-ylamino)piperidin-1-yl)methyl) benzoic acid Into a 25-mL round-bottom flask, was placed methyl 4-[[4-([6-[bis(4-chlorophenyl)methyl]cinnolin-4-yl]amino)piperidin-1-yl]methyl]benzoate (135 mg, 0.22 mmol, 1.00 equiv), sodium hydroxide (18 mg, 0.45 mmol, 2.00 equiv), methanol (3 mL), water (1 mL) and tetrahydrofuran (2 mL). The resulting solution was stirred overnight at 50° C. The pH value of the solution was adjusted to pH 2 with HCl (1 mol/L). The resulting solution was diluted with water (30 mL). The resulting solution was extracted with ethyl acetate (2×50 mL) and the organic layers combined, dried over anhydrous sodium sulfate and concentrated under vacuum. The resulting residue was purified by Prep-TLC with methanol/DCM ratio=1/1 as eluent to yield 4-[[4-([6-[bis(4-chlorophenyl)methyl]cinnolin-4-yl]amino)piperidin-1-yl]methyl]benzoic acid as a off-white solid.

LC-MS (ES, m/z) 597 [M+H]+

1H-NMR (300 MHz, DMSO) δ 12.050 (br, 1H), 8.665 (s, 1H), 8.209 (s, 1H), 8.000 (d, J=9.0 Hz, 1H), 7.885-7.858 (m, 2H), 7.446-7.353 (m, 7H), 7.353-7.071 (m, 5H), 5.755 (s, 1H), 3.682 (br, 1H), 3.550 (s, 2H), 2.829-2.791 (m, 2H), 2.232-2.150 (m, 2H), 1.944-1.906 (m, 2H), 1.661-1.555 (m, 2H). PH-ZHS-YZ1-CI-004-0:

Synthesis Example 4

4-(4-(6-(bis(4-chlorophenyl)methyl)cinnolin-4-ylamino)piperidin-1-ylsulfonyl)benzoic acid Compound #10

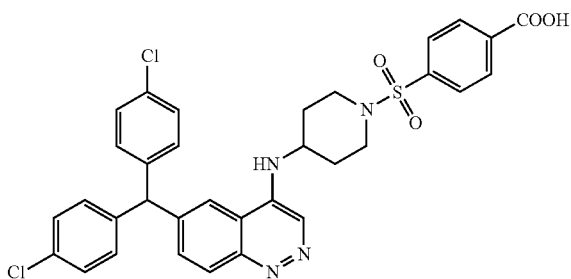 [SMILES: O=C(O)c1ccc(S(=O)(=O)N2CCC(Nc3cnnc4ccc(C(c5ccc(Cl)cc5)c5ccc(Cl)cc5)cc34)CC2)cc1]

Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (120 mg, 0.26 mmol, 1.00 equiv) in dichloromethane (10 mL) and triethylamine (0.073 mL, 2.00 equiv). To the resulting mixture was then added 4-(chlorosulfonyl)benzoic acid (64 mg, 0.29 mmol, 1.10 equiv), in portions at −40° C. The resulting solution was stirred for 20 min at −40° C. and then stirred for a hour at 0° C. The resulting mixture was concentrated under vacuum. The resulting residue was applied to Prep-TLC using methanol/DCM ratio=1/1 as eluent to yield 4-[4-([6-[bis(4-chlorophenyl)methyl]cinnolin-4-yl]amino)piperidine-1-sulfonyl]benzoic acid as a white solid.

LC-MS (ES, m/z) 647 [M+H]+

$^1$H-NMR (300 MHz, DMSO) δ 8.643 (s, 1H), 8.164-8.123 (m, 3H), 8.000 (d, J=9.0 Hz, 1H), 7.833-7.805 (m, 2H), 7.428-7.347 (m, 5H), 7.178-7.059 (m, 5H), 5.750 (s, 1H), 3.713-3.678 (m, 3H), 2.019-1.978 (m, 2H), 1.637-1.529 (m, 2H).

Synthesis Example 5

5-(4-(6-(bis(4-chlorophenyl)methyl)cinnolin-4-ylamino)piperidin-1-ylsulfonyl)thiophene-2-carboxylic acid Compound #16

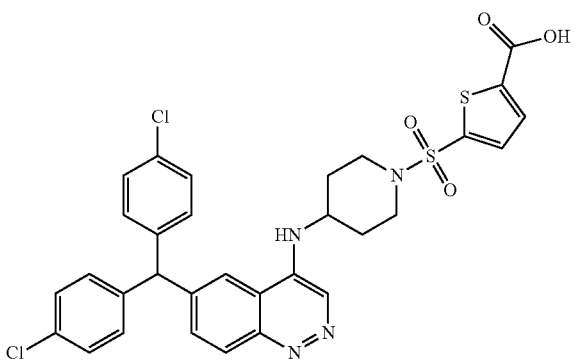 [SMILES: O=C(O)c1ccc(S(=O)(=O)N2CCC(Nc3cnnc4ccc(C(c5ccc(Cl)cc5)c5ccc(Cl)cc5)cc34)CC2)s1]

Step 1: Synthesis of methyl thiophene-2-carboxylate

Into a 500-mL round-bottom flask, was placed a solution of thiophene-2-carboxylic acid (50 g, 390.17 mmol, 1.00 equiv) in DCE (240 mL), methanol (47.4 mL) and sulfuric acid (1.6 mL). The resulting solution was heated to reflux overnight. The reaction was then quenched by the addition of sodium hydroxide (1M, 300 mL). The resulting solution was extracted with DCM (2×300 mL) and the organic layers combined. The resulting mixture was washed with brine (200 mL). The mixture was then dried over anhydrous sodium sulfate and concentrated under vacuum to yield methyl thiophene-2-carboxylate as colorless oil.

$^1$H-NMR (400 MHz, DMSO): δ 7.944-7.929 (m, 1H), 7.813-7.801 (m, 1H), 7.221-7.199 (m, 1H), 3.845 (s, 3H).

Step 2: Synthesis of methyl 5-(chlorosulfonyl)thiophene-2-carboxylate

Into a 250-mL round-bottom flask purged and maintained with an inert atmosphere of nitrogen, was placed a solution of methyl thiophene-2-carboxylate (7.1 g, 49.94 mmol, 1.00 equiv) in dichloromethane (70 mL). To the resulting mixture was then added chlorosulphonic acid (3.5 mL, 1.05 equiv) dropwise with stirring at −10° C. The resulting solution was stirred overnight at room temperature. The resulting solution was allowed to react, with stirring, for an additional 1 h at 45° C. To the resulting mixture was then added pyridine (4.4 mL, 1.10 equiv) dropwise with stirring at −10° C. To the mixture was then added PCl$_5$ (11.4 g, 54.74 mmol, 1.10 equiv) at −10° C. batchwise over 30 min. The resulting solution was allowed to react overnight at room temperature. The reaction mixture was transferred to an addition funnel and added dropwise to ice/water with stirring at room temperature. After addition, the mixture was stirred for additional 1 hour (to assure complete hydrolysis). The solution was extracted with methylene chloride (3×100 mL). The organic layers were combined and washed with water (200 mL) and dried over sodium sulfate. The resulting solution was evaporated in vacuo to yield methyl 5-(chlorosulfonyl)thiophene-2-carboxylate as colorless oil.

$^1$H-NMR (300 MHz, DMSO): δ 7.557-7.519 (m, 1H), 7.165-7.150 (m, 1H), 3.733 (s, 3H).

Step 3: Synthesis of methyl 5-(4-(6-(bis(4-chlorophenyl)methyl)cinnolin-4-ylamino)piperidin-1-ylsulfonyl) thiophene-2-carboxylate Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (100 mg, 0.22 mmol, 1.00 equiv) in dichloromethane (10 mL). To the resulting mixture was then added triethylamine (0.061 mL, 2.00 equiv) dropwise with stirring. To the mixture was then added methyl 5-(chlorosulfonyl)thiophene-2-carboxylate (53 mg, 0.22 mmol, 1.00 equiv) dropwise with stirring at −40° C. The resulting solution was stirred for 30 min at −40° C. and for additional 1 hour at 0° C. The reaction was then quenched by the addition of sat. sodium bicarbonate (30 mL). The resulting solution was extracted with ethyl acetate (2×50 mL) and the organic layers combined, dried over anhydrous sodium sulfate and concentrated under vacuum to yield methyl 5-[4-([6-[bis(4-chlorophenyl)methyl]cinnolin-4-yl]amino)piperidine-1-sulfonyl]thiophene-2-carboxylate as a yellow solid, which was used in next step without further purification.

LC-MS (ES, m/z) 667 [M+H]+

Step 4: Synthesis of 5-(4-(6-(bis(4-chlorophenyl)methyl)cinnolin-4-ylamino)piperidin-1-ylsulfonyl)thiophene-2-carboxylic acid Into a 25-mL round-bottom flask, was placed methyl 5-[4-([6-[bis(4-chlorophenyl)methyl]cinnolin-4-yl]amino)piperidine-1-sulfonyl]thiophene-2-carboxylate (147 mg, 0.22 mmol, 1.00 equiv), sodium hydroxide (18 mg, 0.45 mmol, 2.00 equiv), methanol (3 mL), water (1 mL) and tetrahydrofuran (2 mL). The resulting solution was stirred overnight at 50° C. The pH value of the solution was adjusted to pH 1 with HCl (1 mol/L). The resulting solution was diluted with water (20 mL). The resulting solution was extracted with ethyl acetate (2×100 mL) and the organic layers combined and dried over anhydrous sodium sulfate and concentrated under vacuum. The resulting residue was purified by Prep-TLC with methanol/DCM ratio=1/3 as eluent to yield 5-[4-([6-[bis(4-chlorophenyl)methyl]cinnolin-4-yl]amino)piperidine-1-sulfonyl]thiophene-2-carboxylic acid; trifluoroacetic acid as an off-white solid.

LC-MS (ES, m/z) 653 [M+H]+

1H-NMR (300 MHz, DMSO) δ 8.745 (s, 1H), 8.284 (s, 1H), 8.021 (d, J=9.0 Hz, 1H), 7.810-7.797 (m, 1H), 7.677-7.664 (m, 1H), 7.566-7.536 (m, 1H), 7.430-7.402 (m, 4H), 7.224-7.182 (m, 4H), 5.821 (s, 1H), 3.940 (br, 1H), 3.763-3.724 (m, 2H), 2.727-2.614 (m, 2H), 2.112-2.073 (m, 2H), 1.751-1.646 (m, 2H).

Synthesis Example 6

3-(4-(6-(bis(4-chlorophenyl)methyl)cinnolin-4-ylamino)piperidin-1-ylsulfonyl)benzoic acid Compound #11

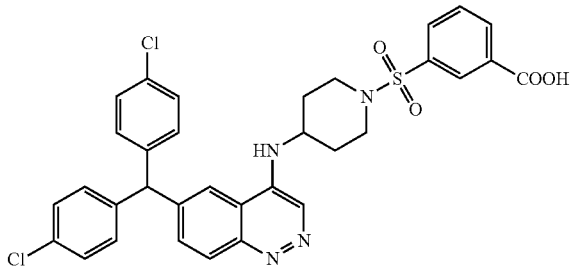 [SMILES: O=C(O)c1cccc(S(=O)(=O)N2CCC(Nc3cnnc4ccc(C(c5ccc(Cl)cc5)c5ccc(Cl)cc5)cc34)CC2)c1]

Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (120 mg, 0.26 mmol, 1.00 equiv) in dichloromethane (10 mL) and triethylamine (0.073 mL, 2.00 equiv). To the resulting mixture was then added 3-(chlorosulfonyl)benzoic acid (64 mg, 0.29 mmol, 1.10 equiv) in several batches at −40° C. The resulting solution was stirred for 20 min at −40° C. and then stirred for 1 hour at 0° C. The resulting mixture was concentrated under vacuum. The resulting residue was applied to Prep-TLC with methanol/DCM ratio=1/1 to yield 3-[4-([6-[bis(4-chlorophenyl)methyl]cinnolin-4-yl]amino)piperidine-1-sulfonyl]benzoic acid as a white solid.

LC-MS (ES, m/z) 647 [M+H]+

1H-NMR (300 MHz, DMSO) δ 8.684 (s, 1H), 8.287-8.262 (m, 3H), 8.051-7.999 (m, 2H), 7.849-7.797 (m, 1H), 7.476-7.386 (m, 5H), 7.173-7.114 (m, 5H), 5.787 (s, 1H), 3.753-3.716 (m, 3H), 2.067-2.029 (m, 2H), 1.683-1.579 (m, 2H). PH-ZHS-YZ1-CI-007-0:

Synthesis Example 7

5-((4-(6-(bis(4-chlorophenyl)methyl)cinnolin-4-ylamino)piperidin-1-yl)methyl)thiophene-2-carboxylic acid Compound #15

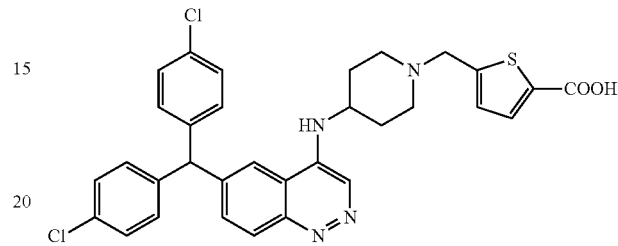

Into a 25-mL round-bottom flask, was placed a solution of 6-[bis(4-chlorophenyl)methyl]-N-(piperidin-4-yl)cinnolin-4-amine (100 mg, 0.22 mmol, 1.00 equiv) in methanol (10 mL), 5-formylthiophene-2-carboxylic acid (41 mg, 0.26 mmol, 1.20 equiv), NaBH3CN (42 mg, 0.67 mmol, 3.00 equiv) and AcOH (1.32 mg, 0.02 mmol, 0.10 equiv). The resulting solution was stirred overnight at room temperature. The resulting solution was diluted with water (20 mL). The solids were collected by filtration. The resulting residue was re-crystallized from EA/PE in the ratio of 1:10 to yield 5-[[4-([6-[bis(4-chlorophenyl)methyl]cinnolin-4-yl]amino)piperidin-1-yl]methyl]thiophene-2-carboxylic acid as a gray solid.

LC-MS (ES, m/z) 603 [M+H]+

1H-NMR (300 MHz, DMSO) δ 8.740 (s, 1H), 8.287 (s, 1H), 8.046-8.016 (m, 1H), 7.590 (s, 1H), 7.527-7.501 (m, 2H), 7.432-7.406 (m, 4H), 7.193-7.166 (m, 4H), 7.048 (s, 1H), 5.813 (s, 1H), 3.773 (br, 3H), 2.952-2.921 (m, 2H), 2.272-2.240 (m, 2H), 2.068-1.956 (m, 2H), 1.686-1.651 (m, 2H). PH-ZHS-YZ1-CI-008-0:

Synthesis Example 8

6-(bis(4-chlorophenyl)methyl)-N-(4-methoxybenzyl)cinnolin-4-amine Compound #20

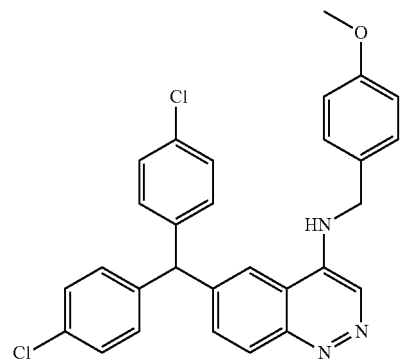 [SMILES: COc1ccc(CNc2cnnc3ccc(C(c4ccc(Cl)cc4)c4ccc(Cl)cc4)cc23)cc1]

Step 1: Synthesis of 6-bromo-N-(4-methoxybenzyl)cinnolin-4-amine

Into a 50-mL round-bottom flask purged and maintained with an inert atmosphere of nitrogen, was placed a solution of 6-bromo-4-chlorocinnoline (500 mg, 2.05 mmol, 1.00 equiv) in isopropanol (15 mL), (4-methoxyphenyl)methanamine (0.806 mL, 3.00 equiv) and DIEA (0.537 mL, 1.50 equiv). The resulting solution was stirred overnight at 90° C. The resulting mixture was concentrated under vacuum. The resulting residue was purified by re-crystallization from ethyl acetate. The solids were collected by filtration. The resulting residue was dissolved in MeOH (10 mL) and the desired product precipitated by addition into water (40 mL). The solids were collected by filtration to yield 6-bromo-N-[(4-methoxyphenyl)methyl]cinnolin-4-amine as a light yellow solid.

LC-MS (ES, m/z) 346 [M+2]$^+$

Step 2: Synthesis of bis(4-chlorophenyl)(4-(4-methoxybenzylamino)cinnolin-6-yl)methanol Into a 100-mL 3-necked round-bottom flask purged and maintained with an inert atmosphere of nitrogen, was placed a solution of 6-bromo-N-[(4-methoxyphenyl)methyl]cinnolin-4-amine (410 mg, 1.19 mmol, 1.00 equiv) in tetrahydrofuran (37 mL). To the resulting mixture was then added LiHMDS (2.98 mL, 2.50 equiv, 1M) dropwise with stirring at 0° C. The resulting solution was stirred for 30 min at 0° C. To the mixture was then added n-BuLi (2.98 mL, 4.00 equiv, 1.6M) dropwise with stirring at −78° C. The resulting solution was allowed to react, with stirring, for an additional 1 h at −78° C. To the mixture was then added bis(4-chlorophenyl)methanone (1.19 g, 4.74 mmol, 3.98 equiv, dissolved in a minimum volume of THF) dropwise with stirring at −78° C. The resulting solution was allowed to react, with stirring, for an additional 2 h at −78° C. and 1 h at 0° C. The reaction was then quenched by the addition of sat. sodium bicarbonate (30 mL). The resulting solution was extracted with ethyl acetate (3×50 mL) and the organic layers combined and dried over anhydrous sodium sulfate. The solids were filtered out. The resulting mixture was concentrated under vacuum. The resulting residue was applied onto a silica gel column with ethyl acetate to yield bis(4-chlorophenyl)(4-[[(4-methoxyphenyl)methyl]amino]cinnolin-6-yl)methanol as a yellow solid.

LC-MS (ES, m/z) 516 [M+1]$^+$

Step 3: Synthesis of 6-(bis(4-chlorophenyl)methyl)-N-(4-methoxybenzyl)cinnolin-4-amine Into a 100-mL 3-necked round-bottom flask purged and maintained with an inert atmosphere of nitrogen, was placed a solution of 6-bromo-N-[(4-methoxyphenyl)methyl]cinnolin-4-amine (410 mg, 1.19 mmol, 1.00 equiv) in tetrahydrofuran (37 mL). To the resulting mixture was then added LiHMDS (2.98 mL, 2.50 equiv, 1M) dropwise with stirring at 0° C. The resulting solution was stirred for 30 min at 0° C. To the resulting mixture was then added n-BuLi (2.98 mL, 4.00 equiv, 1.6M) dropwise with stirring at −78° C. The resulting solution was allowed to react, with stirring, for an additional 1 h at −78° C. To the mixture was added bis(4-chlorophenyl)methanone (1.19 g, 4.74 mmol, 3.98 equiv, dissolved in a minimum volume of THF) dropwise with stirring at −78° C. The resulting solution was allowed to react, with stirring, for an additional 2 h at −78° C. and 1 h at 0° C. The reaction was then quenched by the addition of sat. sodium bicarbonate (10 mL). The resulting solution was extracted with ethyl acetate (3×50 mL) and the organic layers combined and dried over anhydrous sodium sulfate. The solids were filtered out. The resulting mixture was concentrated under vacuum. The resulting residue was applied onto a silica gel column with ethyl acetate to yield bis(4-chlorophenyl)(4-[[(4-methoxyphenyl)methyl]amino]cinnolin-6-yl)methanol as a yellow solid.

LC-MS (ES, m/z) 500 [M+H]$^+$ $^1$H-NMR (400 MHz, DMSO) δ 8.550 (s, 1H), 8.166-8.098 (m, 2H), 8.060 (d, J=8.8 Hz, 1H), 7.552-7.527 (m, 1H), 7.438-7.417 (m, 4H), 7.340-7.319 (m, 2H), 7.219-7.198 (m, 4H), 6.922-6.900 (m, 2H), 5.844 (s, 1H), 4.544 (d, J=6.8 Hz, 2H), 3.723 (s, 3H).

Synthesis Example 9

4-((6-(bis(4-chlorophenyl)methyl)cinnolin-4-ylamino)methyl)phenol Compound #21

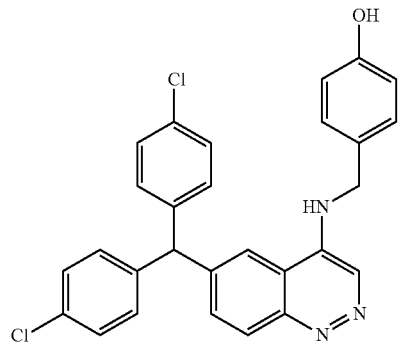 [SMILES: Oc1ccc(CNc2cnnc3ccc(C(c4ccc(Cl)cc4)c4ccc(Cl)cc4)cc23)cc1]

Into a 50-mL round-bottom flask, was placed a solution of 6-[bis(4-chlorophenyl)methyl]-N-[(4-methoxyphenyl)methyl]cinnolin-4-amine (390 mg, 0.78 mmol, 1.00 equiv) in dichloromethane (30 mL). To the resulting mixture was then added BBr$_3$ (3.12 mL, 1M, 4.00 equiv) dropwise with stirring at −78° C. The resulting solution was stirred for 1 h at −78° C. and 3 h at 0° C. The reaction was then quenched by the addition of sat. sodium bicarbonate (50 mL). The resulting solution was extracted with DCM (2×100 mL) and the organic layers combined and dried over sodium sulfate. The solids were filtered out. The resulting mixture was concentrated under vacuum. The resulting residue was purified by Prep-TLC with ethyl acetate as eluent to yield 4-[([6-[bis(4-chlorophenyl)methyl]cinnolin-4-yl]amino)methyl]phenol as a yellow solid.

LC-MS (ES, m/z) 486 [M+H]$^+$ $^1$H-NMR (300 MHz, DMSO) δ 9.322 (s, 1H), 8.497 (s, 1H), 8.151 (s, 1H), 8.069-8.018 (m, 2H), 7.522 (d, J=9.0 Hz, 1H), 7.431-7.403 (m, 4H), 7.214-7.186 (m, 6H), 6.720 (d, J=7.2 Hz, 2H), 5.828 (s, 1H), 4.482-4.463 (m, 2H).

Synthesis Example 10

5-(4-(6-(bis(4-chlorophenyl)methyl)cinnolin-4-ylamino)piperidin-1-ylsulfonyl)furan-2-carboxylic acid Compound #14

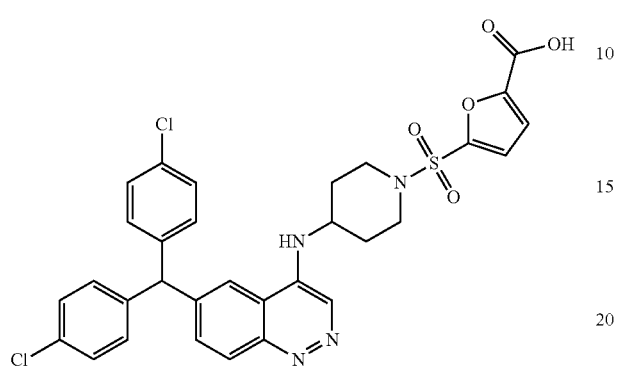

Step 1: Synthesis of methyl 5-(4-(6-(bis(4-chlorophenyl)methyl)cinnolin-4-ylamino)piperidin-1-ylsulfonyl) furan-2-carboxylate Into a 25-mL round-bottom flask purged and maintained with an inert atmosphere of nitrogen, was placed 6-[bis(4-chlorophenyl)methyl]-N-(piperidin-4-yl)cinnolin-4-amine (100 mg, 0.22 mmol, 1.00 equiv) in DCM (10 mL). To the resulting mixture was then added triethylamine (0.061 mL, 2.00 equiv) dropwise with stirring. To the mixture was then added methyl 5-(chlorosulfonyl)furan-2-carboxylate (54 mg, 0.24 mmol, 1.10 equiv) in several batches at −40° C. The resulting solution was stirred for 30 min at −40° C. and for additional 1 hour at 0° C. The reaction was then quenched by the addition of sat. sodium bicarbonate (30 mL). The resulting solution was extracted with ethyl acetate (2×50 mL) and the organic layers combined and dried over anhydrous sodium sulfate and concentrated under vacuum, to yield methyl 5-[4-([6-[bis(4-chlorophenyl)methyl]cinnolin-4-yl]amino)piperidine-1-sulfonyl]furan-2-carboxylate as a yellow solid, which was used directly to next step without further purification.

LC-MS (ES, m/z) 652 [M+2]$^+$

Step 2: Synthesis of 5-(4-(6-(bis(4-chlorophenyl)methyl)cinnolin-4-ylamino)piperidin-1-ylsulfonyl) furan-2-carboxylic acid Into a 25-mL round-bottom flask purged and maintained with an inert atmosphere of nitrogen, was placed methyl 5-[4-([6-[bis(4-chlorophenyl)methyl]cinnolin-4-yl]amino) piperidine-1-sulfonyl]furan-2-carboxylate (143 mg, 0.22 mmol, 1.00 equiv), sodium hydroxide (18 mg, 0.45 mmol, 2.00 equiv), methanol (3 mL), water (1 mL) and tetrahydrofuran (2 mL). The resulting solution was stirred overnight at 50° C. The resulting solution was diluted with water (20 mL). The pH value of the solution was adjusted to pH 1 with HCl (1 mol/L). The resulting solution was extracted with ethyl acetate (2×50 mL) and the organic layers combined and dried over anhydrous sodium sulfate and concentrated under vacuum. The resulting residue was purified by re-crystallization from EA to yield 5-[4-([6-[bis(4-chlorophenyl)methyl]cinnolin-4-yl]amino)piperidine-1-sulfonyl]furan-2-carboxylic acid as a yellow solid.

LC-MS (ES, m/z) 637 [M+H]$^+$ $^1$H-NMR (300 MHz, DMSO) δ 14.750 (br, 1H), 9.140 (br, 1H), 7.853 (s, 1H), 8.664 (s, 1H), 7.997 (d, J=9.0 Hz, 1H), 7.697-7.667 (m, 1H), 7.338-7.250 (m, 6H), 7.155-7.127 (m, 4H), 5.794 (s, 1H), 4.135 (br, 1H), 3.765-3.727 (m, 2H), 2.810-2.734 (m, 2H), 2.054-2.014 (m, 2H), 1.943-1.836 (m, 2H).

Synthesis Example 11

2-(4-(6-(bis(4-chlorophenyl)methyl)cinnolin-4-ylamino)piperidin-1-ylsulfonyl)benzoic acid Compound #19

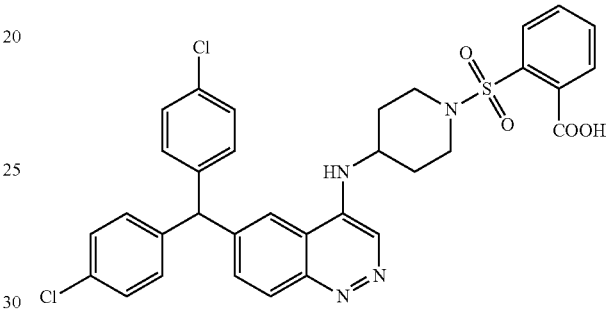

Step 1: Synthesis of methyl 2-(4-(6-(bis(4-chlorophenyl)methyl)cinnolin-4-ylamino)piperidin-1-ylsulfonyl) benzoate Into a 25-mL round-bottom flask purged and maintained with an inert atmosphere of nitrogen, was placed a solution of 6-[bis(4-chlorophenyl)methyl]-N-(piperidin-4-yl)cinnolin-4-amine (100 mg, 0.22 mmol, 1.00 equiv) in dichloromethane (10 mL) and triethylamine (44 mg, 0.43 mmol, 2.00 equiv). To the resulting mixture was then added methyl 2-(chlorosulfonyl)benzoate (56 mg, 0.24 mmol, 1.10 equiv) in several batches at −40° C. The resulting solution was stirred for 30 min at −40° C. and for additional 2 hours at 0° C. The resulting mixture was concentrated under vacuum. The resulting residue was applied onto a silica gel column with ethyl acetate to yield methyl 2-[4-([6-[bis(4-chlorophenyl)methyl]cinnolin-4-yl]amino)piperidine-1-sulfonyl]benzoate as a yellow solid.

LC-MS (ES, m/z) 661 [M+1]$^+$

Step 2: Synthesis of 2-(4-(6-(bis(4-chlorophenyl)methyl)cinnolin-4-ylamino)piperidin-1-ylsulfonyl) benzoic acid Into a 25-mL round-bottom flask, was placed methyl 2-[4-([6-[bis(4-chlorophenyl)methyl]cinnolin-4-yl]amino) piperidine-1-sulfonyl]benzoate (120 mg, 0.18 mmol, 1.00 equiv), sodium hydroxide (18 mg, 0.45 mmol, 2.00 equiv), methanol (3 mL), water (1 mL) and tetrahydrofuran (2 mL). The resulting solution was stirred overnight at 50° C. The pH value of the solution was adjusted to pH 1 with HCl (1 mol/L). The resulting solution was diluted with water (30 mL). The resulting solution was extracted with ethyl acetate (3×50 mL) and the organic layers combined and dried over anhydrous sodium sulfate. The solids were filtered out. The resulting mixture was concentrated under vacuum. The resulting residue was purified by Prep-TLC with methanol/DCM as eluent to yield 2-[4-([6-[bis(4-chlorophenyl)methyl]cinnolin-4-yl]amino)piperidine-1-sulfonyl]benzoic acid as an off-white solid.

LC-MS (ES, m/z) 647 [M+H]$^+$ $^1$H-NMR (300 MHz, DMSO) δ 8.174 (s, 1H), 8.264 (s, 1H), 8.055-8.025 (m, 1H), 7.621-7.596 (m, 1H), 7.495-7.391 (m, 6H), 7.320-7.272 (m, 1H), 7.224-7.096 (m, 6H), 5.792 (s, 1H), 3.903-3.862 (m, 2H), 3.799-3.733 (m, 1H), 2.761-2.683 (m, 2H), 1.989-1.956 (m, 2H), 1.654-1.546 (m, 2H).

Synthesis Example 12

2-((4-(6-(bis(4-chlorophenyl)methyl)cinnolin-4-ylamino)piperidin-1-yl)methyl)benzoic acid Compound #18

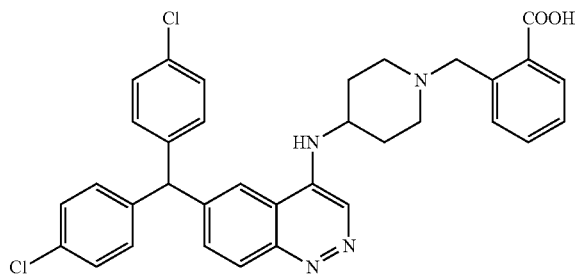 [SMILES: O=C(O)c1ccccc1CN1CCC(Nc2cnnc3ccc(C(c4ccc(Cl)cc4)c4ccc(Cl)cc4)cc23)CC1]

Into a 25-mL round-bottom flask, was placed a solution of 6-[bis(4-chlorophenyl)methyl]-N-(piperidin-4-yl)cinnolin-4-amine (80 mg, 0.17 mmol, 1.00 equiv) in methanol (10 mL), 2-formylbenzoic acid (30 mg, 0.20 mmol, 1.20 equiv), AcOH (1.02 mg, 0.02 mmol, 0.10 equiv) and NaBH$_3$CN (32 mg, 0.51 mmol, 3.00 equiv). The resulting solution was stirred overnight at room temperature. The pH value of the solution was adjusted to pH 1 with HCl (1 mol/L). The resulting solution was extracted with ethyl acetate (2×50 mL) and the organic layers combined and dried over anhydrous sodium sulfate. The solids were filtered out. The resulting mixture was concentrated under vacuum. The resulting residue was purified by Prep-TLC with methanol/DCM ratio=1/4 as eluent to yield 2-[[4-([6-[bis(4-chlorophenyl)methyl]cinnolin-4-yl]amino)piperidin-1-yl]methyl]benzoic acid as a white solid.

LC-MS (ES, m/z) 597 [M+H]$^+$ $^1$H-NMR (400 MHz, DMSO) δ 8.800 (s, 1H), 8.223 (s, 1H), 8.074 (d, J=8.8 Hz, 1H), 7.884 (d, J=8.8 Hz, 1H), 7.500-7.390 (m, 8H), 7.189-7.168 (m, 5H), 5.805 (s, 1H), 4.047 (s, 2H), 3.954-3.936 (m, 1H), 3.099-3.070 (m, 2H), 2.790-2.731 (m, 2H), 2.129-2.099 (m, 2H), 1.755-1.668 (m, 2H).

Synthesis Example 13

5-[4-([6-[bis(4-chlorophenyl)methyl]cinnolin-4-yl]amino)piperidine-1-sulfonyl]thiophene-3-carboxylic acid Compound #32

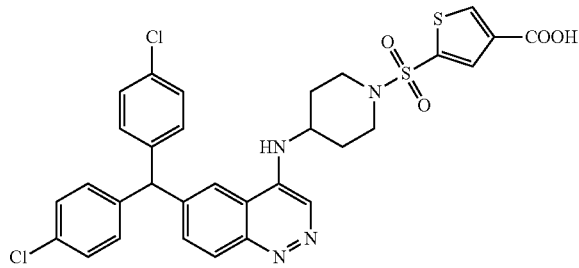 [SMILES: O=C(O)c1csc(S(=O)(=O)N2CCC(Nc3cnnc4ccc(C(c5ccc(Cl)cc5)c5ccc(Cl)cc5)cc34)CC2)c1]

Step 1: Synthesis of methyl thiophene-3-carboxylate

Into a 500-mL round-bottom flask, was placed thiophene-3-carboxylic acid (20 g, 156.07 mmol, 1.00 equiv), DCE (150 mL, 30.00 equiv), methanol (7.5 g, 234.08 mmol, 1.50 equiv) and sulfuric acid (23 g, 234.50 mmol, 1.50 equiv). The resulting solution was stirred overnight at 90° C. The resulting mixture was concentrated under vacuum. The resulting solution was diluted with DCM (500 mL). The resulting mixture was washed with 0.5 mol/L sodium hydroxide (aq.) (3×250 mL). The resulting mixture was washed with brine (3×250 mL). The mixture was dried over anhydrous sodium sulfate. The solids were filtered out. The resulting mixture was concentrated under vacuum, to yield methyl thiophene-3-carboxylate as a brown liquid.

LC-MS (ES, m/z): 143 [M+H]$^+$

Step 2: Synthesis of 4-(methoxycarbonyl)thiophene-2-sulfonic acid

Into a 250-mL round-bottom flask, was placed a solution of methyl thiophene-3-carboxylate (5 g, 35.17 mmol, 1.00 equiv) in dichloromethane (50 mL). To the resulting mixture was then added chloranesulfonic acid (4.5 g, 38.62 mmol, 1.10 equiv) dropwise with stirring at 0° C. The resulting solution was stirred overnight at room temperature. The resulting mixture was concentrated under vacuum to yield 4-(methoxycarbonyl)thiophene-2-sulfonic acid as brown crude oil, which was used in the next step directly.

Step 3: Synthesis of methyl 5-(chlorosulfonyl)thiophene-3-carboxylate

Into a 250-mL round-bottom flask, was placed a solution of 4-(methoxycarbonyl)thiophene-2-sulfonic acid (8 g, 36.00 mmol, 1.00 equiv) in dichloromethane (100 mL). To the resulting mixture was then added pyridine (3.2 g, 40.46 mmol, 1.10 equiv) at −20° C. To the mixture was then added PCl$_5$ (11 g, 52.82 mmol, 1.50 equiv) at −20° C. The resulting solution was stirred overnight at room temperature. The resulting solution was diluted with of water/ice (300 mL). The resulting solution was extracted with DCM (3×300 mL) and the organic layers combined and dried over anhydrous sodium sulfate. The resulting mixture was concentrated under vacuum. The resulting residue was applied onto a silica gel column with EA/PE (1:5) to yield methyl 5-(chlorosulfonyl)thiophene-3-carboxylate as off-white crude oil.

GC-MS (ES, m/z): 240

Step 4: Synthesis of methyl 5-(4-(6-(bis(4-chlorophenyl)methyl)cinnolin-4-ylamino)piperidin-1-ylsulfonyl) thiophene-3-carboxylate Into a 50-mL round-bottom flask, was placed a solution of 6-[bis(4-chlorophenyl)methyl]-N-(piperidin-4-yl)cinnolin-4-amine (100 mg, 0.22 mmol, 1.00 equiv) in dichloromethane (25 mL). To the resulting mixture was then added triethylamine (44 mg, 0.43 mmol, 1.10 equiv) dropwise with stirring. To the mixture was then added a solution of methyl 5-(chlorosulfonyl)thiophene-3-carboxylate (57 mg, 0.24 mmol, 1.10 equiv) in dichloromethane (1 mL) dropwise with stirring. The resulting solution was stirred overnight at room temperature. The reaction was then quenched by the addition of water (25 mL). The resulting solution was extracted with ethyl acetate (3×50 mL) and the organic layers combined and concentrated under vacuum. The resulting residue was applied onto a silica gel column with dichloromethane/methanol (5:1), to yield methyl 5-[4-([6-[bis(4-chlorophenyl)methyl]cinnolin-4-yl]amino)piperidine-1-sulfonyl]thiophene-3-carboxylate as a off-white solid.

LC-MS (ES, m/z): 667 [M+H]$^+$

Step 5: Synthesis of 5-[4-([6-[bis(4-chlorophenyl)methyl]cinnolin-4-yl]amino)piperidine-1-sulfonyl] thiophene-3-carboxylic acid Into a 50-mL round-bottom flask, was placed methyl 5-[4-([6-[bis(4-chlorophenyl)methyl]cinnolin-4-yl]amino) piperidine-1-sulfonyl]thiophene-3-carboxylate (100 mg, 0.15 mmol, 1.00 equiv), methanol (5 mL, 30.00 equiv), tetrahydrofuran (15 mL, 30.00 equiv) and sodium hydroxide (12 mg, 0.30 mmol, 2.00 equiv). The resulting solution was stirred overnight at room temperature. The pH value of the solution was adjusted to pH 4 with HCl (1 mol/L). The resulting solution was extracted with ethyl acetate (3×50 mL) and the organic layers combined and dried over anhydrous sodium sulfate. The solids were filtered out. The resulting mixture was concentrated under vacuum. The resulting residue was purified by Prep-HPLC with the following conditions (1#waters2767-5): Column, SunFire Prep C$_{18}$, 19*150 mm 5 umH PrepC-001(T) 18600256819513816414 04; mobile phase, Phase A: water with 0.05% NH$_4$HCO$_3$ Phase B: CH$_3$CN (45% CH$_3$CN up to 95% in 12 min, hold 95% in 1 min, down to 45% in 1 min, hold 45% in 1 min); Detector, UV220&254 nm, to yield 5-[4-([6-[bis(4-chlorophenyl)methyl]cinnolin-4-yl]amino) piperidine-1-sulfonyl]thiophene-3-carboxylic acid as an off-white solid.

LC-MS (ES, m/z): 653 [M+H]$^+$ $^1$H-NMR (400 MHz, DMSO) δ: 8.735 (s, 1H), 8.691 (s, 1H), 8.240 (s, 1H), 8.056 (d, J=8.8 Hz, 1H), 7.818-7.814 (m, 1H), 7.484 (d, J=8.8 Hz, 1H), 7.426-7.405 (m, 4H), 7.186-7.165 (m, 5H), 5.809 (s, 1H), 3.837 (br, 2H), 3.752-3.724 (m, 2H), 2.667-2.610 (m, 2H), 2.111-2.083 (m, 2H), 1.718-1.638 (m, 2H).

Synthesis Example 14

6-(bis(4-chlorophenyl)methyl)-N-(1-(trifluoromethylsulfonyl)pyrrolidin-3-yl)cinnolin-4-amine Compound #26

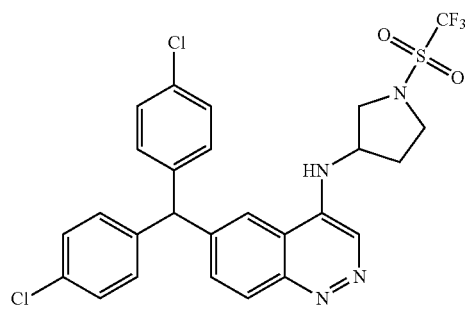 [SMILES: O=S(=O)(N1CCC(Nc2cnnc3ccc(C(c4ccc(Cl)cc4)c4ccc(Cl)cc4)cc23)C1)C(F)(F)F]

Step 1: Synthesis of tert-butyl 3-(6-bromocinnolin-4-ylamino)pyrrolidine-1-carboxylate Into a 100-mL round-bottom flask, was placed a solution of 6-bromo-4-chlorocinnoline (500 mg, 2.05 mmol, 1.00 equiv) in isopropanol (30 mL), DIEA (0.716 mL, 2.00 equiv) and tert-butyl 3-aminopyrrolidine-1-carboxylate (459 mg, 2.46 mmol, 1.20 equiv). The resulting solution was stirred overnight at 90° C. The resulting mixture was concentrated under vacuum. The resulting residue was applied onto a silica gel column with ethyl acetate to yield tert-butyl 3-[(6-bromocinnolin-4-yl)amino]pyrrolidine-1-carboxylate as a yellow solid.

LCMS (ES, m/z): 393 [M+H]$^+$

Step 2: Synthesis of tert-butyl 3-(6-(bis(4-chlorophenyl)(hydroxy)methyl)cinnolin-4-ylamino)pyrrolidine-1-carboxylate Into a 100-mL 3-necked round-bottom flask purged and maintained with an inert atmosphere of nitrogen, was placed a solution of tert-butyl 3-[(6-bromocinnolin-4-yl)amino]pyrrolidine-1-carboxylate (440 mg, 1.12 mmol, 1.00 equiv) in tetrahydrofuran (30 mL). To the resulting mixture was then added LiHMDS (2.24 mL, 2.00 equiv, 1M) dropwise with stirring at 0° C. The resulting solution was stirred for 30 min at 0° C. To the resulting mixture was then added n-BuLi (1.79 mL, 4.00 equiv, 2.5M) dropwise with stirring at −78° C. The resulting solution was allowed to react, with stirring, for an additional 1 h at −78° C. To the mixture was then added bis(4-chlorophenyl)methanone (1.12 g, 4.46 mmol, 4.00 equiv, dissolved in a minimum volume of THF) dropwise with stirring at −78° C. The resulting solution was allowed to react, with stirring, for an additional 1 h at −78° C. The resulting mixture was then warmed to room temperature slowly and quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate, to yield tert-butyl 3-([6-[bis(4-chlorophenyl)(hydroxy)methyl]cinnolin-4-yl] amino)pyrrolidine-1-carboxylate as a yellow solid.

Step 3: Synthesis of 6-(bis(4-chlorophenyl)methyl)-N-(pyrrolidin-3-yl)cinnolin-4-amine Into a 100-mL round-bottom flask, was placed a solution of tert-butyl 3-([6-[bis(4-chlorophenyl)(hydroxy)methyl]cinnolin-4-yl]amino)pyrrolidine-1-carboxylate (420 mg, 0.74 mmol, 1.00 equiv) in dichloromethane (30 mL). To the resulting mixture was then added Et$_3$SiH (0.472 mL, 4.00 equiv) dropwise with stirring at 0° C. To the mixture was then added trifluoroacetic acid (1.42 mL, 25.00 equiv) dropwise with stirring at 0° C. The resulting solution was stirred overnight at room temperature. The reaction was then quenched by the addition of sat. sodium bicarbonate (50 mL). The resulting solution was extracted with DCM (2×100 mL) and the organic layers combined and dried over anhydrous sodium sulfate. The solids were filtered out. The resulting mixture was concentrated under vacuum. The resulting residue was re-crystallized from EA/PE in the ratio of 1:9 to yield 6-[bis(4-chlorophenyl)methyl]-N-(pyrrolidin-3-yl)cinnolin-4-amine as a yellow solid.

LCMS (ES, m/z): 449 [M+H]$^+$

Step 4: Synthesis of 6-(bis(4-chlorophenyl)methyl)-N-(1-(trifluoromethylsulfonyl)pyrrolidin-3-yl)cinnolin-4-amine Into a 50-mL round-bottom flask, was placed 6-[bis(4-chlorophenyl)methyl]-N-(pyrrolidin-3-yl)cinnolin-4-amine (80 mg, 0.18 mmol, 1.00 equiv) and dichloromethane (15 mL, 30.00 equiv). To the resulting mixture was then added triethylamine (36 mg, 0.36 mmol, 2.00 equiv) and (trifluoromethane)sulfonyl trifluoromethanesulfonate (55 mg, 0.19 mmol, 1.10 equiv) dropwise with stirring at 0° C. The resulting solution was stirred for 2 h at 0° C. The reaction was then quenched by the addition of water (25 mL). The resulting solution was extracted with ethyl acetate (3×25 mL) and the organic layers combined. The resulting mixture was washed with water (3×25 mL) and brine (3×25 mL). The mixture was dried over anhydrous sodium sulfate. The solids were filtered out. The resulting mixture was concentrated under vacuum. The resulting residue was applied onto a silica gel column with ethyl acetate/petroleum ether (1:1). The resulting residue was purified by Prep-HPLC with the following conditions: Column, SunFire Prep C$_{18}$, 19*150 mm 5 umH PrepC-001(T)18600256819513816414 04; mobile phase, Phase A: water with 0.05% NH$_4$HCO$_3$ Phase B: CH$_3$CN (45% CH$_3$CN up to 95% in 12 min, hold 95% in 1 min, down to 45% in 1 min, hold 45% in 1 min); Detector, UV220&254 nm, to yield 6-[bis(4-chlorophenyl)methyl]-N-[1-(trifluoromethane)sulfonylpyrrolidin-3-yl]cinnolin-4-amine as a off-white solid.

LCMS (ES, m/z): 581[M+H]$^+$ $^1$H-NMR (400 MHz, DMSO) δ: 8.789 (s, 1H), 8.211 (s, 1H), 8.134 (d, J=8.8 Hz, 1H), 7.538 (d, J=1.6 Hz, 1H), 7.428-7.408 (m, 4H), 7.320 (d, J=6.0 Hz, 1H), 7.791-7.165 (m, 4H), 5.841 (s, 1H), 4.646-4.604 (m, 1H), 3.981-3.940 (m, 1H), 3.817-3.758 (m, 1H), 3.699-3.641 (m, 1H), 3.576-3.539 (m, 1H), 2.480-2.446 (m, 1H), 2.244-2.180 (m, 1H).

Synthesis Example 15

6-(bis(4-chlorophenyl)methyl)-N-phenethylcinnolin-4-amine Compound #25

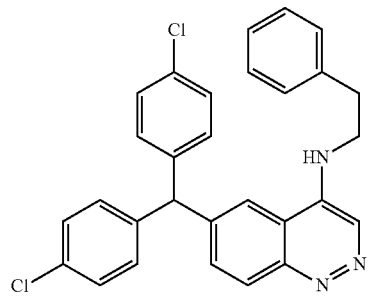 [SMILES: Clc1ccc(C(c2ccc(Cl)cc2)c2ccc3nncc(NCCc4ccccc4)c3c2)cc1]

Step 1: Synthesis of 6-bromo-N-phenethylcinnolin-4-amine

Into a 100-mL round-bottom flask, was placed a solution of 6-bromo-4-chlorocinnoline (300 mg, 1.23 mmol, 1.00 equiv) in isopropanol (30 mL), 2-phenylethan-1-amine hydrochloride (777 mg, 4.93 mmol, 4.00 equiv) and DIEA (2.14 mL, 10.00 equiv). The resulting solution was stirred overnight at 90° C. The resulting mixture was concentrated under vacuum. The resulting residue was dissolved in sat. sodium bicarbonate (50 mL). The resulting solution was extracted with ethyl acetate (2×50 mL) and the organic layers combined and dried over anhydrous sodium sulfate. The solids were filtered out. The resulting mixture was concentrated under vacuum. The resulting residue was applied onto a silica gel column with ethyl acetate to yield 6-bromo-N-(2-phenylethyl)cinnolin-4-amine as a yellow solid.

LC-MS (ES, m/z) 328 [M+H]$^+$

Step 2: Synthesis of bis(4-chlorophenyl)(4-(phenethylamino)cinnolin-6-yl)methanol Into a 100-mL 3-necked round-bottom flask purged and maintained with an inert atmosphere of nitrogen, was placed a solution of 6-bromo-N-(2-phenylethyl)cinnolin-4-amine (300 mg, 0.91 mmol, 1.00 equiv) in tetrahydrofuran (50 mL). To the resulting mixture was then added LiHMDS (2.28 mL, 2.50 equiv, 1M) dropwise with stirring at 0° C. The resulting solution was stirred for 30 min at 0° C. To the mixture was then added n-BuLi (1.46 mL, 4.00 equiv, 2.5M) dropwise with stirring at −78° C. The resulting solution was allowed to react, with stirring, for an additional 3 h at −78° C. To the mixture was then added bis(4-chlorophenyl)methanone (914 mg, 3.64 mmol, 4.00 equiv, dissolved in a minimum volume of THF) dropwise with stirring at −78° C. The resulting solution was allowed to react, with stirring, for an additional 1 h at −78° C. The resulting mixture was then warmed to room temperature slowly and quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate to yield bis(4-chlorophenyl)([4-[(2-phenylethyl)amino]cinnolin-6-yl])methanol as a yellow solid.

LC-MS (ES, m/z) 500 [M+H]$^+$

Step 3: Synthesis of 6-(bis(4-chlorophenyl)methyl)-N-phenethylcinnolin-4-amine

Into a 100-mL round-bottom flask, was placed a solution of bis(4-chlorophenyl)([4-[(2-phenylethyl)amino]cinnolin-6-yl])methanol (300 mg, 0.60 mmol, 1.00 equiv) in dichloromethane (30 mL). To the resulting mixture was then added Et$_3$SiH (0.382 mL, 4.00 equiv) dropwise with stirring at 0° C. To this was added trifluoroacetic acid (1.15 mL, 25.00 equiv) dropwise with stirring at 0° C. The resulting solution was stirred overnight at room temperature. The reaction was then quenched by the addition of sat. sodium bicarbonate (50 mL). The resulting solution was extracted with DCM (2×100 mL) and the organic layers combined and dried over anhydrous sodium sulfate. The solids were filtered out. The resulting mixture was concentrated under vacuum. The resulting residue was purified by Prep-TLC with 1:1 EA/PE as eluent to yield 6-[bis(4-chlorophenyl)methyl]-N-(2-phenylethyl)cinnolin-4-amine as a yellow solid.

LC-MS (ES, m/z) 484 [M+H]$^+$ $^1$H-NMR (300 MHz, DMSO) δ 8.688 (s, 1H), 8.075-8.046 (m, 2H), 7.545-7.520 (m, 2H), 7.430-7.402 (m, 4H), 7.299-7.284 (m, 4H), 7.255-7.177 (m, 5H), 5.818 (s, 1H), 3.615-3.547 (m, 2H), 2.982-2.932 (m, 2H)

Synthesis Example 16

6-(bis(4-chlorophenyl)methyl)-N-(1-(phenylsulfonyl)pyrrolidin-3-yl)cinnolin-4-amine Compound #27

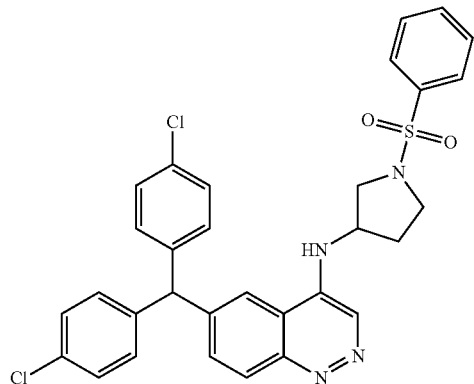 [SMILES: O=S(=O)(c1ccccc1)N1CCC(Nc2cnnc3ccc(C(c4ccc(Cl)cc4)c4ccc(Cl)cc4)cc23)C1]

Into a 100-mL round-bottom flask, was placed 6-[bis(4-chlorophenyl)methyl]-N-(pyrrolidin-3-yl)cinnolin-4-amine (80 mg, 0.18 mmol, 1.00 equiv), dichloromethane (30 mL, 30.00 equiv), triethylamine (36 mg, 0.36 mmol, 2.00 equiv) and benzenesulfonyl chloride (35 mg, 0.20 mmol, 1.10 equiv). The resulting solution was stirred for 2 h at 25° C. The reaction was then quenched by the addition of water (25 mL). The resulting solution was extracted with ethyl acetate (3×50 mL) and the organic layers combined. The resulting mixture was washed with water (3×50 mL) and brine (3×50 mL). The mixture was dried over anhydrous sodium sulfate. The solids were filtered out. The resulting mixture was concentrated under vacuum. The resulting solution was diluted with DMF (4 mL). The resulting residue was purified by Prep-HPLC with the following conditions (1#waters2767-5): Column, SunFire Prep C18, 19*150 mm 5 umH PrepC-001(T)18600256819513816414 04; mobile phase, Phase A: water with 0.05% NH$_4$HCO$_3$ Phase B: CH$_3$CN (45% CH$_3$CN up to 95% in 12 min, hold 95% in 1 min, down to 45% in 1 min, hold 45% in 1 min); Detector, UV220&254 nm, to yield N-[1-(benzenesulfonyl)pyrrolidin-3-yl]-6-[bis(4-chlorophenyl)methyl]cinnolin-4-amine as a off-white solid.

LC-MS (ES, m/z) 589 [M+H]$^+$ $^1$H-NMR (400 MHz, DMSO) δ 8.024 (s, 1H), 8.141-8.084 (m, 2H), 7.794-7.770 (m, 2H), 7.507-7.401 (m, 8H), 7.206-7.134 (m, 5H), 5.783 (s, 1H), 4.335-4.292 (m, 1H), 3.625-3.583 (m, 1H), 3.450-3.409 (m, 1H), 3.338-3.200 (m, 2H), 2.236-2.186 (m, 1H), 1.967-1.918 (m, 1H).

Synthesis Example 17

6-(bis(4-chlorophenyl)methyl)-N-(1-phenethylpiperidin-4-yl)cinnolin-4-amine Compound #30

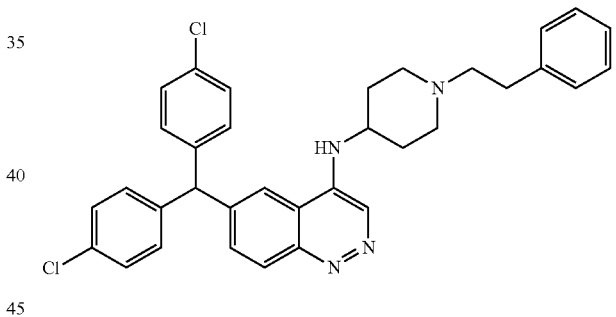

Into a 25-mL round-bottom flask, was placed 2-phenylacetaldehyde (29 mg, 0.24 mmol, 1.10 equiv), a solution of 6-[bis(4-chlorophenyl)methyl]-N-(piperidin-4-yl)cinnolin-4-amine (100 mg, 0.22 mmol, 1.00 equiv) in methanol (5 mL), AcOH (1.3 mg, 0.02 mmol, 0.10 equiv) and NaBH$_3$CN (42 mg, 0.67 mmol, 3.00 equiv). The resulting solution was stirred overnight at room temperature. The resulting mixture was concentrated under vacuum. The resulting residue was dissolved in sat. sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The resulting residue was purified by Prep-TLC with EA/PE ratio=1/1 as eluent, to yield 6-[bis(4-chlorophenyl)methyl]-N-[1-(2-phenylethyl)piperidin-4-yl]cinnolin-4-amine as a light yellow solid.

LC-MS (ES, m/z) 567 [M+H]$^+$ $^1$H-NMR (300 MHz, DMSO) δ 8.715 (s, 1H), 8.263 (s, 1H), 8.048 (d, J=9.0 Hz, 1H), 7.462 (d, J=8.8 Hz, 1H), 7.420-7.391 (m, 4H), 7.310-7.158 (m, 10H), 5.792 (s, 1H), 3.370 (br, 3H), 3.065-2.531 (m, 5H), 2.220-1.956 (m, 5H), 1.658 (br, 2H).

Synthesis Example 18

3-[2-[4-([6-[bis(4-chlorophenyl)methyl]cinnolin-4-yl]amino)piperidin-1-yl]ethyl]benzoate Compound #23

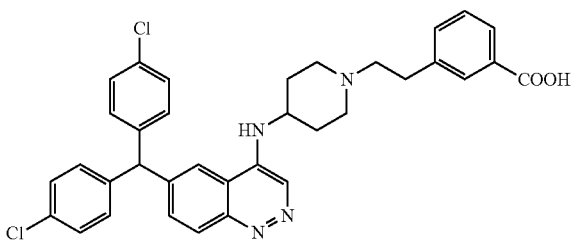 [SMILES: O=C(O)c1cccc(CCN2CCC(Nc3cnnc4ccc(C(c5ccc(Cl)cc5)c5ccc(Cl)cc5)cc34)CC2)c1]

Step 1: Synthesis of (E)-methyl 3-(2-methoxyvinyl)benzoate

Into a 100-mL 3-necked round-bottom flask purged and maintained with an inert atmosphere of nitrogen, was placed a solution of (methoxymethyl)triphenylphosphanium chloride (6.366 g, 18.57 mmol, 1.20 equiv) in tetrahydrofuran (50 mL). To the resulting mixture was then added KOtBu (20.2 mL, 1.30 equiv, 1M) dropwise with stirring at −78° C. The resulting solution was stirred for 1 h at −78° C. To the resulting mixture was then added a solution of methyl 3-formylbenzoate (2.531 g, 15.42 mmol, 1.00 equiv) in tetrahydrofuran (10 mL) dropwise with stirring at −78° C. The resulting solution was allowed to react, with stirring, for an additional 30 min at −78° C. The resulting solution was allowed to react, with stirring, for an additional 3 h at room temperature. The reaction was then quenched by the addition of sat. NH$_4$Cl (100 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:9) to yield methyl 3-[(E)-2-methoxyethenyl]benzoate as a colorless oil.

GCMS (ES, m/z) 192

Step 2: Synthesis of methyl 3-(2-oxoethyl)benzoate

Into a 100-mL round-bottom flask, was placed a solution of methyl 3-[(E)-2-methoxyethenyl]benzoate (300 mg, 1.56 mmol, 1.00 equiv) in tetrahydrofuran (15 mL). To the resulting mixture was then added conc. HCl (2.26 mL) dropwise with stirring at 0° C. The resulting solution was stirred for 2 h at room temperature. The reaction was then quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum to yield methyl 3-(2-oxoethyl)benzoate as yellow oil, which was used in the next step without purification.

GCMS (ES, m/z) 178

Step 3: Synthesis of (E)-methyl 3-(2-methoxyvinyl)benzoate

Into a 25-mL round-bottom flask, was placed a solution of 6-[bis(4-chlorophenyl)methyl]-N-(piperidin-4-yl)cinnolin-4-amine (50 mg, 0.11 mmol, 1.00 equiv) in methanol (5 mL), methyl 3-(2-oxoethyl)benzoate (23 mg, 0.13 mmol, 1.20 equiv), AcOH (0.7 mg, 0.01 mmol, 0.10 equiv) and NaBH$_3$CN (21 mL, 3.00 equiv). The resulting solution was stirred overnight at room temperature. The resulting mixture was concentrated under vacuum. The resulting residue was dissolved in sat. sodium bicarbonate (30 mL). The resulting solution was extracted with ethyl acetate (2×50 mL) and the organic layers combined and dried over anhydrous sodium sulfate and concentrated under vacuum. The resulting residue was purified by Prep-TLC with 5% methanol/DCM as eluent to yield methyl 3-[2-[4-([6-[bis(4-chlorophenyl)methyl]cinnolin-4-yl]amino)piperidin-1-yl]ethyl]benzoate as a yellow solid.

LC-MS (ES, m/z) 625 [M+H]$^+$

Step 4: Synthesis of (E)-methyl 3-(2-methoxyvinyl)benzoate

Into a 25-mL round-bottom flask, was placed methyl 3-[2-[4-([6-[bis(4-chlorophenyl)methyl]cinnolin-4-yl]amino)piperidin-1-yl]ethyl]benzoate (100 mg, 0.16 mmol, 1.00 equiv), sodium hydroxide (13 mg, 0.33 mmol, 2.00 equiv), methanol (3 mL), water (1 mL) and tetrahydrofuran (2 mL). The resulting solution was stirred overnight at room temperature. The resulting mixture was concentrated under vacuum. The resulting residue was dissolved in MeOH (5 mL) and 1M aq. NaOH (10 mL). The pH value of the solution was adjusted to pH 1 with HCl (1 mol/L). The solids were collected by filtration to yield 3-[2-[4-([6-[bis(4-chlorophenyl)methyl]cinnolin-4-yl]amino)piperidin-1-yl]ethyl]benzoic acid as an off-white solid.

LC-MS (ES, m/z) 611 [M+H]$^+$ $^1$H-NMR (300 MHz, DMSO) δ 11.259 (br, 1H), 9.947 (br, 1H), 8.927 (s, 1H), 8.824 (s, 1H), 8.033 (d, J=9.0 Hz, 1H), 7.914-7.845 (m, 3H), 7.585-7.425 (m, 5H), 7.207-7.180 (m, 4H), 5.869 (s, 1H), 4.432 (br, 1H), 3.738-3.701 (m, 2H), 3.238-3.145 (m, 6H), 2.336-2.225 (m, 4H).

Synthesis Example 19

4-(2-(4-(6-(bis(4-chlorophenyl)methyl)cinnolin-4-ylamino)piperidin-1-yl)ethyl)benzoic acid Compound #31

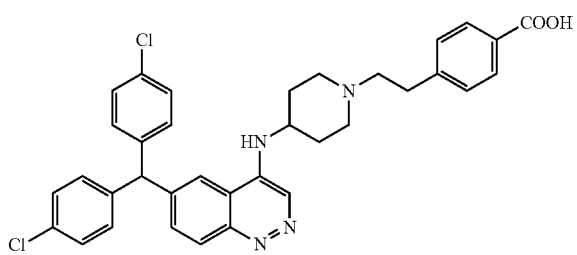 [SMILES: O=C(O)c1ccc(CCN2CCC(Nc3cnnc4ccc(C(c5ccc(Cl)cc5)c5ccc(Cl)cc5)cc34)CC2)cc1]

Step 1: Synthesis of (E)-methyl 4-(2-methoxyvinyl)benzoate

Into a 250-mL round-bottom flask, was placed a solution of (methoxymethyl)triphenylphosphanium chloride (13.6 g, 39.67 mmol, 1.30 equiv) in tetrahydrofuran (50 mL). To the resulting mixture was then added KOtBu (42.7 mL, 1.40 equiv, 1M) dropwise with stirring at −78° C. The resulting solution was stirred for 20 min at −78° C. To the resulting mixture was then added a solution of methyl 4-formylbenzoate (5 g, 30.46 mmol, 1.00 equiv) in tetrahydrofuran (15 mL) dropwise with stirring at −78° C. The resulting solution was allowed to react, with stirring, for an additional 30 min at −78° C. The resulting solution was allowed to react, with stirring, overnight, at room temperature. The reaction was then quenched by the addition of sat. sodium bicarbonate (100 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:9) to yield methyl 4-[(E)-2-methoxyethenyl]benzoate as a white solid.

GCMS (ES, m/z): 192

Step 2: Synthesis of methyl 4-(2-oxoethyl)benzoate

Into a 50-mL round-bottom flask, was placed a solution of methyl 4-[(E)-2-methoxyethenyl]benzoate (600 mg, 3.12 mmol, 1.00 equiv) in tetrahydrofuran (27 mL). To the resulting mixture was then added HCl conc. (4.53 mL) dropwise with stirring at 0° C. The resulting solution was stirred for 4 h at room temperature. The reaction was then quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum to yield methyl 4-(2-oxoethyl)benzoate as a yellow solid, which was used in the next step without purification.

GCMS (ES, m/z): 178

Step 3: Synthesis of methyl 4-(2-(4-(6-(bis(4-chlorophenyl)methyl)cinnolin-4-ylamino)piperidin-1-yl) ethyl) benzoate Into a 25-mL round-bottom flask, was placed a solution of 6-[bis(4-chlorophenyl)methyl]-N-(piperidin-4-yl)cinnolin-4-amine (100 mg, 0.22 mmol, 1.00 equiv) in methanol (5 mL), methyl 4-(2-oxoethyl)benzoate (46 mg, 0.26 mmol, 1.20 equiv), AcOH (1 mg, 0.02 mmol, 0.10 equiv) and NaBH₃CN (42 mg, 0.67 mmol, 3.00 equiv). The resulting solution was stirred overnight at room temperature. The resulting mixture was concentrated under vacuum. The resulting residue was purified by Prep-TLC with EA/PE ratio=2/1 to yield methyl 4-[2-[4-([6-[bis(4-chlorophenyl) methyl]cinnolin-4-yl]amino)piperidin-1-yl]ethyl]benzoate as a yellow solid.

LC-MS (ES, m/z): 625 [M+H]⁺

Step 4: Synthesis of 4-(2-(4-(6-(bis(4-chlorophenyl) methyl)cinnolin-4-ylamino)piperidin-1-yl)ethyl) benzoic acid Into a 25-mL round-bottom flask, was placed methyl 4-[2-[4-([6-[bis(4-chlorophenyl)methyl]cinnolin-4-yl] amino)piperidin-1-yl]ethyl]benzoate (50 mg, 0.08 mmol, 1.00 equiv), sodium hydroxide (6.4 mg, 0.16 mmol, 2.00 equiv), methanol (3 mL), water (1 mL) and tetrahydrofuran (2 mL). The resulting solution was stirred overnight at 50° C. The pH value of the solution was adjusted to pH 1 with HCl (1 mol/L). The resulting solution was extracted with ethyl acetate (2×30 mL) and the organic layers combined. The solids were filtered out. The resulting mixture was concentrated under vacuum. The resulting residue was purified by Prep-TLC with methanol/DCM ratio=1/4 as eluent to yield 4-[2-[4-([6-[bis(4-chlorophenyl)methyl]cinnolin-4-yl] amino)piperidin-1-yl]ethyl]benzoic acid as an off-white solid.

LC-MS (ES, m/z): 611 [M+H]⁺

¹H-NMR (400 MHz, DMSO) δ: 8.703 (s, 1H), 8.254 (s, 1H), 8.047 (d, J=9.0 Hz, 1H), 7.837-7.812 (m, 2H), 7.468-7.396 (m, 5H), 7.312-7.268 (m, 2H), 7.191-7.163 (m, 4H), 7.086-7.056 (m, 1H), 5.794 (s, 1H), 3.710 (br, 1H), 3.956-3.912 (m, 2H), 3.812-3.800 (m, 2H), 2.556-2.510 (m, 2H), 2.195-2.111 (m, 2H), 1.958-1.922 (m, 2H), 1.688-1.556 (m, 2H).

Synthesis Example 20

6-(bis(4-chlorophenyl)methyl)-N-(pyrrolidin-3-yl) cinnolin-4-amine Compound #24

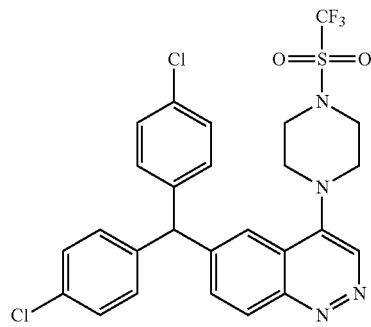 [SMILES: O=S(=O)(N1CCN(c2cnnc3ccc(C(c4ccc(Cl)cc4)c4ccc(Cl)cc4)cc23)CC1)C(F)(F)F]

Step 1: Synthesis of 6-bromo-4-(4-(trifluoromethylsulfonyl)piperazin-1-yl)cinnoline Into a 100-mL round-bottom flask, was placed a solution of 6-bromo-4-chlorocinnoline (300 mg, 1.23 mmol, 1.00 equiv) in isopropanol (30 mL), 1-(trifluoromethane)sulfonylpiperazine hydrochloride (1.25 g, 4.91 mmol, 4.00 equiv) and DIEA (1.71 mL, 8.00 equiv). The resulting solution was stirred overnight at 90° C. The resulting mixture was concentrated under vacuum. The resulting residue was dissolved in sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (10:1) to yield 6-bromo-4-[4-(trifluoromethane)sulfonylpiperazin-1-yl]cinnoline as a yellow solid.

LCMS (ES, m/z): 427 [M+H]⁺

Step 2: Synthesis of bis(4-chlorophenyl)(4-(4-(trifluoromethylsulfonyl)piperazin-1-yl)cinnolin-6-yl) methanol Into a 100-mL 3-necked round-bottom flask purged and maintained with an inert atmosphere of nitrogen, was placed a solution of 6-bromo-4-[4-(trifluoromethane)sulfonylpiperazin-1-yl]cinnoline (300 mg, 0.71 mmol, 1.00 equiv) in tetrahydrofuran (40 mL). To the resulting mixture was then added n-BuLi (1.14 mL, 4.00 equiv, 2.5M) dropwise with stirring at −78° C. Immediately, to the mixture was then added bis(4-chlorophenyl)methanone (713 mg, 2.84 mmol, 4.00 equiv, dissolved in a minimum volume of THF) dropwise with stirring at −78° C. The reaction was then warmed to room temperature slowly and quenched by the addition of saturated sodium bicarbonate (50 mL). The resulting solution was extracted with ethyl acetate (3×50 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:1) to yield bis(4-chlorophenyl)([4-[4-(trifluoromethane)sulfonylpiperazin-1-yl]cinnolin-6-yl])methanol as a yellow solid.

LCMS (ES, m/z): 597 [M+H]+

Step 3: Synthesis of 6-(bis(4-chlorophenyl)methyl)-N-(pyrrolidin-3-yl)cinnolin-4-amine Into a 50-mL round-bottom flask, was placed a solution of bis(4-chlorophenyl)([4-[4-(trifluoromethane)sulfonylpiperazin-1-yl]cinnolin-6-yl])methanol (80 mg, 0.13 mmol, 1.00 equiv) in dichloromethane (10 mL). To the resulting mixture was then added Et₃SiH (0.083 mL, 4.00 equiv) dropwise with stirring at 0° C. To the mixture was then added trifluoroacetic acid (0.249 mL, 25.00 equiv) dropwise with stirring at 0° C. The resulting solution was stirred for 3 h at room temperature. The reaction was then quenched by the addition of sat. sodium bicarbonate (50 mL). The resulting solution was extracted with DCM (2×50 mL) and the organic layers combined, dried over anhydrous sodium sulfate and concentrated under vacuum. The resulting residue was purified by Prep-TLC with EA/PE ratio=1/1 as eluent to yield 6-[bis(4-chlorophenyl)methyl]-4-[4-(trifluoromethane)sulfonylpiperazin-1-yl]cinnoline as a yellow solid.

LCMS (ES, m/z): 581[M+H]+
1H-NMR (300 MHz, DMSO) δ: 8.986 (s, 1H), 8.312 (d, J=9.0 Hz, 1H), 7.655-7.620 (m, 1H), 7.454-7.387 (m, 5H), 7.219-7.191 (m, 4H), 6.019 (s, 1H), 3.550 (br, 4H), 3.350 (br, 4H).

Synthesis Example 21

4-(4-benzylpiperazin-1-yl)-6-(bis(4-chlorophenyl)methyl)cinnoline Compound #22

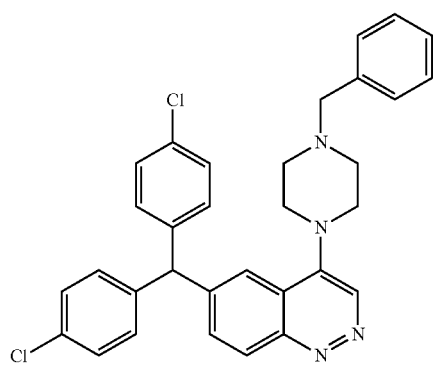 [SMILES: Clc1ccc(C(c2ccc(Cl)cc2)c2ccc3nncc(N4CCN(Cc5ccccc5)CC4)c3c2)cc1]

Step 1: Synthesis of 4-(4-benzylpiperazin-1-yl)-6-bromocinnoline

Into a 100-mL round-bottom flask, was placed 6-bromo-4-chlorocinnoline (300 mg, 1.23 mmol, 1.00 equiv), 1-benzylpiperazine (866 mg, 4.91 mmol, 4.00 equiv), DIEA (0.428 mL, 2.00 equiv) and i-PrOH (30 mL). The resulting solution was stirred overnight at 90° C. The resulting mixture was concentrated under vacuum. The resulting residue was dissolved in sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate to yield 4-(4-benzylpiperazin-1-yl)-6-bromocinnoline as a yellow solid.

LC-MS (ES, m/z) 383 [M+H]+

Step 2: Synthesis of (4-(4-benzylpiperazin-1-yl)cinnolin-6-yl)bis(4-chlorophenyl)methanol Into a 100-mL 3-necked round-bottom flask purged and maintained with an inert atmosphere of nitrogen, was placed 4-(4-benzylpiperazin-1-yl)-6-bromocinnoline (230 mg, 0.60 mmol, 1.00 equiv) in THF (36 mL). To the resulting mixture was then added n-BuLi (0.96 mL, 4.00 equiv, 2.5M) dropwise with stirring at −78° C. The resulting solution was stirred for 30 min at −78° C. To the resulting mixture was then added bis(4-chlorophenyl)methanone (602 mg, 2.40 mmol, 4.00 equiv, dissolved in a minimum volume of THF) dropwise with stirring at −78° C. The reaction was then warmed to room temperature slowly and quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:1) to yield [4-(4-benzylpiperazin-1-yl)cinnolin-6-yl]bis(4-chlorophenyl)methanol as a yellow solid.

LC-MS (ES, m/z) 555 [M+H]+

Step 3: Synthesis of 4-(4-benzylpiperazin-1-yl)-6-(bis(4-chlorophenyl)methyl)cinnoline Into a 25-mL round-bottom flask, was placed a solution of [4-(4-benzylpiperazin-1-yl)cinnolin-6-yl]bis(4-chlorophenyl)methanol (170 mg, 0.31 mmol, 1.00 equiv) in dichloromethane (10 mL). To the resulting mixture was then added Et₃SiH (0.198 mL, 4.00 equiv) dropwise with stirring at 0° C. To this was added trifluoroacetic acid (0.593 mL, 25.00 equiv) dropwise with stirring at 0° C. The resulting solution was stirred for 3 h at room temperature. The reaction was then quenched by the addition of sat. sodium bicarbonate (30 mL). The resulting solution was extracted with DCM (3×50 mL) and the organic layers combined and dried over anhydrous sodium sulfate. The solids were filtered out. The resulting mixture was concentrated under vacuum. The resulting residue was purified by Prep-TLC with EA/PE ratio=1/1 as eluent to yield 4-(4-benzylpiperazin-1-yl)-6-[bis(4-chlorophenyl)methyl]cinnoline as a yellow solid.

LC-MS (ES, m/z) 539 [M+H]+
1H-NMR (300 MHz, DMSO) δ 8.890 (s, 1H), 8.245 (d, J=9.0 Hz, 1H), 7.577 (d, J=9.0 Hz, 1H), 7.442-7.171 (m, 14H), 5.983 (s, 1H), 3.522 (s, 2H), 3.178 (br, 4H), 2.271 (br, 4H).

Synthesis Example 22

1-[6-[bis(4-chlorophenyl)methyl]cinnolin-4-yl]-N-phenylpiperidin-4-amine Compound #29

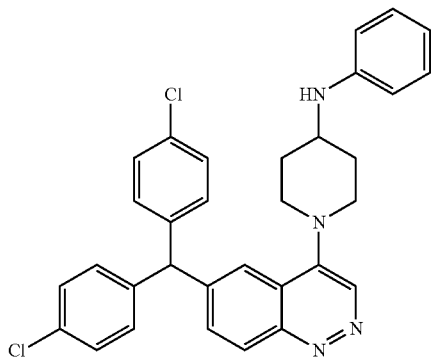 [SMILES: Clc1ccc(C(c2ccc(Cl)cc2)c2ccc3nncc(N4CCC(Nc5ccccc5)CC4)c3c2)cc1]

Step 1: Synthesis of tert-butyl 4-(phenylamino)piperidine-1-carboxylate

Into a 500-mL round-bottom flask, was placed a solution of tert-butyl 4-oxopiperidine-1-carboxylate (25 g, 125.47 mmol, 1.30 equiv) in dichloromethane (125 mL), aniline (9.75 g, 104.70 mmol, 1.00 equiv) and AcOH (12.1 mL). The resulting solution was stirred for 30 min at room temperature. To the resulting mixture was then added NaHB(OAc)$_3$ (20.45 g, 96.46 mmol, 1.00 equiv) in several batches at 0° C. The resulting solution was stirred overnight at room temperature. The reaction was then quenched by the addition of sat. NH$_4$Cl (100 mL). The resulting solution was extracted with DCM (3×100 mL) and the organic layers combined and dried over anhydrous sodium sulfate. The solids were filtered out. The resulting mixture was concentrated under vacuum. The resulting residue was re-crystallized from EA/HEX in the ratio of 1:9 to yield tert-butyl 4-(phenylamino)piperidine-1-carboxylate as a light yellow solid.

LC-MS (ES, m/z) 277 [M+H]$^+$

Step 2: Synthesis of N-phenylpiperidin-4-amine

Into a 250-mL round-bottom flask, was placed tert-butyl 4-(phenylamino)piperidine-1-carboxylate (14 g, 50.66 mmol, 1.00 equiv) and sat. HCl/EtOH (30 mL). The resulting solution was stirred overnight at room temperature. The resulting mixture was concentrated under vacuum. The resulting residue was dissolved in ethyl acetate (100 mL). The solids were collected by filtration and washed with ethyl acetate (50 mL) to yield N-phenylpiperidin-4-amine dihydrochloride as a white solid.

LC-MS (ES, m/z) 177 [M+H]$^+$

Step 3: Synthesis of 1-(6-bromocinnolin-4-yl)-N-phenylpiperidin-4-amine

Into a 100-mL round-bottom flask, was placed a solution of 6-bromo-4-chlorocinnoline (300 mg, 1.23 mmol, 1.00 equiv) in isopropanol (30 mL), N-phenylpiperidin-4-amine dihydrochloride (1.23 g, 4.94 mmol, 4.00 equiv) and DIEA (2.14 mL, 10.00 equiv). The resulting solution was stirred overnight at 90° C. The resulting mixture was concentrated under vacuum. The resulting residue was dissolved in sat. sodium bicarbonate (50 mL). The resulting solution was extracted with ethyl acetate (2×100 mL) and the organic layers combined and dried over sodium sulfate. The solids were filtered out. The resulting mixture was concentrated under vacuum. The resulting residue was applied onto a silica gel column with ethyl acetate to yield 1-(6-bromocinnolin-4-yl)-N-phenylpiperidin-4-amine as a yellow solid.

Step 4: Synthesis of bis(4-chlorophenyl)(4-(4-(phenylamino)piperidin-1-yl)cinnolin-6-yl)methanol Into a 100-mL 3-necked round-bottom flask purged and maintained with an inert atmosphere of nitrogen, was placed a solution of 1-(6-bromocinnolin-4-yl)-N-phenylpiperidin-4-amine (200 mg, 0.52 mmol, 1.00 equiv) in tetrahydrofuran (20 mL). To the resulting mixture was then added LiHMDS (1.31 mL, 2.50 equiv, 1M) dropwise with stirring at −20° C. The resulting solution was stirred for 20 min at −20° C. To the resulting mixture was then added n-BuLi (0.84 mL, 4.00 equiv, 2.5M) dropwise with stirring at −78° C. The resulting solution was allowed to react, with stirring, for an additional 30 min at −78° C. To the mixture was added bis(4-chlorophenyl)methanone (524 mg, 2.09 mmol, 4.00 equiv) dropwise with stirring at −78° C. The resulting solution was allowed to react, with stirring, for an additional overnight at room temperature. The reaction was then quenched by the addition of water (25 mL). The resulting solution was extracted with ethyl acetate (3×50 mL) and the organic layers combined. The resulting mixture was washed with water (3×25 mL) and brine (3×25 mL). The mixture was dried over sodium sulfate. The solids were filtered out. The resulting mixture was concentrated under vacuum. The resulting residue was applied onto a silica gel column with EA/PE (1:1) to yield bis(4-chlorophenyl)([4-[4-(phenylamino)piperidin-1-yl]cinnolin-6-yl])methanol as a brown solid.

LC-MS (ES, m/z) 555 [M+H]$^+$

Step 5: Synthesis of 1-[6-[bis(4-chlorophenyl)methyl]cinnolin-4-yl]-N-phenylpiperidin-4-amine Into a 50-mL round-bottom flask, was placed bis(4-chlorophenyl)([4-[4-(phenylamino)piperidin-1-yl]cinnolin-6-yl])methanol (120 mg, 0.22 mmol, 1.00 equiv), dichloromethane (20 mL, 30.00 equiv), trifluoroacetic acid (524 mg, 4.64 mmol, 25.00 equiv) and Et$_3$SiH (100 mg, 0.86 mmol, 4.00 equiv). The resulting solution was stirred overnight at room temperature. The resulting mixture was concentrated under vacuum. The reaction was then quenched by the addition of water (25 mL). The resulting solution was extracted with ethyl acetate (3×50 mL) and the organic layers combined. The resulting mixture was washed with water (3×50 mL) and brine (3×50 mL). The mixture was dried over anhydrous sodium sulfate and concentrated under vacuum. The resulting residue was purified by Prep-HPLC with the following conditions (1#waters2767-5): Column, SunFire Prep C$_{18}$, 19*150 mm 5 umH PrepC-001(T) 18600256819513816414 04; mobile phase, Phase A: water with 0.05% NH$_4$HCO$_3$ Phase B: CH$_3$CN (45% CH$_3$CN up to 95% in 12 min, hold 95% in 1 min, down to 45% in 1 min, hold 45% in 1 min); Detector, UV220&254 nm, to yield 1-[6-[bis(4-chlorophenyl)methyl]cinnolin-4-yl]-N-phenylpiperidin-4-amine as a light yellow solid.

LC-MS (ES, m/z) 539 [M+H]$^+$ $^1$H-NMR (400 MHz, DMSO) δ 8.919 (s, 1H), 8.246 (d, J=8.8 Hz, 1H), 7.602 (d, J=8.8 Hz, 1H), 7.430-7.383 (m,

5H), 7.198-7.177 (m, 4H), 7.098-7.060 (m, 2H), 6.629 (d, J=8.0 Hz, 2H), 6.543-6.507 (m, 1H), 5.997 (s, 1H), 5.450 (d, J=8.0 Hz, 1H), 3.553-3.479 (m, 3H), 3.108-3.054 (m, 2H), 1.954-1.927 (m, 2H), 1.481-1.431 (m, 2H).

Synthesis Example 23

N-(1-benzylpyrrolidin-3-yl)-6-(bis(4-chlorophenyl)methyl)cinnolin-4-amine Compound #28

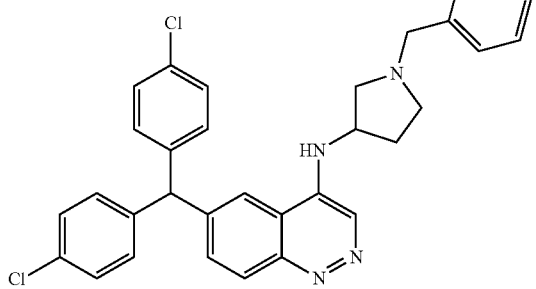

Into a 50-mL round-bottom flask, was placed 6-[bis(4-chlorophenyl)methyl]-N-(pyrrolidin-3-yl)cinnolin-4-amine (80 mg, 0.18 mmol, 1.00 equiv), N,N-dimethylformamide (15 mL, 30.00 equiv), potassium carbonate (49 mg, 0.35 mmol, 2.00 equiv) and (bromomethyl)benzene (34 mg, 0.20 mmol, 1.10 equiv). The resulting solution was stirred for 2 h at 25° C. The reaction was then quenched by the addition of water (25 mL). The resulting solution was extracted with ethyl acetate (3×25 mL) and the organic layers combined. The resulting mixture was washed with water (3×25 mL) and brine (3×25 mL). The mixture was dried over anhydrous sodium sulfate. The solids were filtered out. The resulting mixture was concentrated under vacuum. The resulting residue was applied onto a silica gel column with ethyl acetate/petroleum ether (1:1). The resulting residue was purified by Prep-HPLC with the following conditions (1#waters2767-5): Column, SunFire Prep C18, 19*150 mm 5 umH PrepC-001(T)18600256819513816414 04; mobile phase, Phase A: water with 0.05% NH$_4$HCO$_3$ Phase B: CH$_3$CN (45% CH$_3$CN up to 95% in 12 min, hold 95% in 1 min, down to 45% in 1 min, hold 45% in 1 min); Detector, UV220&254 nm, to yield N-(1-benzylpyrrolidin-3-yl)-6-[bis(4-chlorophenyl)methyl]cinnolin-4-amine as an off-white solid.

LC-MS (ES, m/z) 539 [M+H]$^+$ $^1$H-NMR (400 MHz, DMSO) δ 8.600 (s, 1H), 8.306 (s, 1H), 8.070 (d, J=8.8 Hz, 1H), 7.496 (d, J=8.8 Hz, 1H), 7.427-7.406 (m, 4H), 7.325-7.305 (m, 5H), 7.262-7.172 (m, 5H), 5.801 (s, 1H), 4.290-4.284 (m, 1H), 3.626 (s, 2H), 2.943-2.901 (m, 1H), 2.722-2.681 (m, 1H), 2.630-2.595 (m, 1H), 2.385-2.339 (m, 1H), 1.895-1.853 (m, 1H).

Synthesis Example 24

4-(2-(6-(bis(4-chlorophenyl)methyl)cinnolin-4-ylamino)ethyl)benzoic acid Compound #37

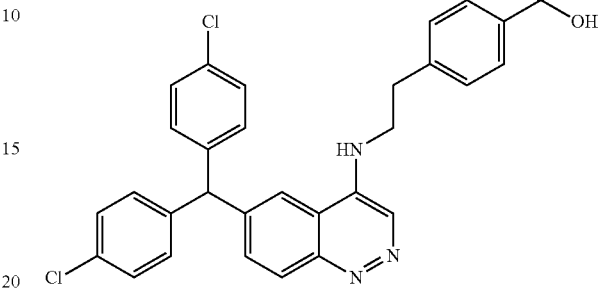

Step 1: Synthesis of 6-bromo-4-tert-butoxycinnoline

Into a 100-mL round-bottom flask purged and maintained with an inert atmosphere of nitrogen, was placed a solution of 6-bromo-4-chlorocinnoline (1 g, 4.11 mmol, 1.00 equiv) in tetrahydrofuran (30 mL). To the resulting mixture was then added KOtBu (4.94 mL, 1.20 equiv, 1M) dropwise with stirring at −20° C. The resulting solution was stirred for 3 h at 0° C. The resulting solution was diluted with ethyl acetate (100 mL). The resulting mixture was washed with water (2×80 mL). The mixture was dried over anhydrous sodium sulfate. The solids were filtered out. The resulting mixture was concentrated under vacuum. The resulting residue was applied onto a silica gel column with ethyl acetate/petroleum ether (3:1) to yield 6-bromo-4-(tert-butoxy)cinnoline as a yellow solid.

LC-MS (ES, m/z): 225 [M+H]$^+$

Step 2: Synthesis of (4-tert-butoxycinnolin-6-yl)bis(4-chlorophenyl)methanol

Into a 100-mL 3-necked round-bottom flask purged and maintained with an inert atmosphere of nitrogen, was placed a solution of 6-bromo-4-(tert-butoxy)cinnoline (500 mg, 1.78 mmol, 1.00 equiv) in tetrahydrofuran (30 ml). To the resulting mixture was then added n-BuLi (0.85 mL) dropwise with stirring. The resulting solution was stirred for 20 min at −78° C. To the mixture was then added a solution of bis(4-chlorophenyl)methanone (536 mg, 2.13 mmol, 1.20 equiv) in tetrahydrofuran (20 ml) dropwise with stirring. The resulting solution was stirred for 30 min at −78° C. The reaction was then quenched by the addition of water (50 mL). The resulting solution was extracted with ethyl acetate (2×100 mL) and the organic layers combined and dried over sodium sulfate. The solids were filtered out. The resulting mixture was concentrated under vacuum. The resulting residue was applied onto a silica gel column with EA:PE (3:1), to yield [4-(tert-butoxy)cinnolin-6-yl]bis(4-chlorophenyl)methanol as a yellow solid.

Step 3: Synthesis of 6-(bis(4-chlorophenyl)methyl)cinnolin-4-ol

Into a 100-mL round-bottom flask, was placed [4-(tert-butoxy)cinnolin-6-yl]bis(4-chlorophenyl)methanol (500 mg, 1.10 mmol, 1.00 equiv), dichloromethane (50 mL), Et₃SiH (0.7 mL) and trifluoroacetic acid (2.1 mL). The resulting solution was stirred overnight at 25° C. The resulting mixture was concentrated under vacuum. The resulting residue was applied onto a silica gel column with ethyl acetate/petroleum ether (5:1) to yield 6-[bis(4-chlorophenyl)methyl]cinnolin-4-ol as a yellow solid.

LC-MS (ES, m/z): 381[M+H]⁺

Step 4: Synthesis of 6-(bis(4-chlorophenyl)methyl)-4-chlorocinnoline

Into a 100-mL round-bottom flask, was placed 6-[bis(4-chlorophenyl)methyl]cinnolin-4-ol (400 mg, 1.05 mmol, 1.00 equiv), dichloromethane (40 mL), DIEA (130 mg), N,N-dimethylformamide (50 mg) and ClOCCOCl (1.32 g, 10.39 mmol, 10.00 equiv). The resulting solution was stirred overnight at 25° C. The resulting solution was diluted with DCM (100 mL). The resulting mixture was washed with aq. sodium bicarbonate (2×80 mL). The mixture was dried over sodium sulfate. The solids were filtered out. The resulting mixture was concentrated under vacuum to yield 6-[bis(4-chlorophenyl)methyl]-4-chlorocinnoline as yellow oil.

Step 5: Synthesis of methyl 4-(2-(6-(bis(4-chlorophenyl)methyl)cinnolin-4-ylamino)ethyl)benzoate Into a 10-mL round-bottom flask purged and maintained with an inert atmosphere of nitrogen, was placed 6-[bis(4-chlorophenyl)methyl]-4-chlorocinnoline (100 mg, 0.25 mmol, 1.00 equiv), methyl 4-(2-aminoethyl)benzoate hydrochloride (80 mg, 0.37 mmol, 1.50 equiv), Pd₂(dba)₃ (12 mg), XantPhos (24 mg), Cs₂C03 (245 mg, 0.75 mmol, 3.00 equiv) and 1,4-dioxane (2 mL). The resulting solution was stirred overnight at 90° C. The solids were filtered out. The resulting mixture was concentrated under vacuum. The resulting residue was applied onto a silica gel column with EA:PE (3:1) to yield methyl 4-[2-([6-[bis(4-chlorophenyl)methyl]cinnolin-4-yl]amino)ethyl]benzoate as a yellow solid.

LC-MS (ES, m/z):542 [M+H]⁺

Step 6: Synthesis of 4-(2-(6-(bis(4-chlorophenyl)methyl)cinnolin-4-ylamino)ethyl)benzoic acid Into a 100-mL round-bottom flask, was placed methyl 4-[2-([6-[bis(4-chlorophenyl)methyl]cinnolin-4-yl]amino)ethyl]benzoate (80 mg, 0.15 mmol, 1.00 equiv), methanol (10 mL) and 1M sodium hydroxide (20 mL). The resulting solution was stirred overnight at 25° C. The resulting mixture was concentrated under vacuum. The pH value of the solution was adjusted to pH 3-4 with 10% HCl. The solids were collected by filtration. The resulting residue was purified by Prep-HPLC with the following conditions (1#waters2767-5): Column, SunFire Prep C18, 19*150 mm 5 umH PrepC-001(T)18600256819513816414 04; mobile phase, Phase A: water with 0.05% TFA Phase B: CH₃CN (35% CH₃CN up to 70% in 12 min, hold 95% in 1 min, down to 35% in 1 min, hold 35% in 1 min); Detector, UV220&254 nm, to yield 4-[2-([6-[bis(4-chlorophenyl)methyl]cinnolin-4-yl]amino)ethyl]benzoic acid as a white solid.

LC-MS (ES, m/z) 526 [M−H]⁻

¹H-NMR (400 MHz, DMSO) δ 8.711 (s, 1H), 8.249 (s, 1H), 7.932-7.860 (m, 4H), 7.458-7.429 (m, 6H), 7.211-7.190 (m, 4H), 5.891 (s, 1H), 3.981 (t, J=6.8 Hz, 2H), 3.116 (t, J=6.8 Hz, 2H).

Synthesis Example 25

3-(2-(6-(bis(4-chlorophenyl)methyl)cinnolin-4-ylamino)ethyl)benzoic acid Compound #38

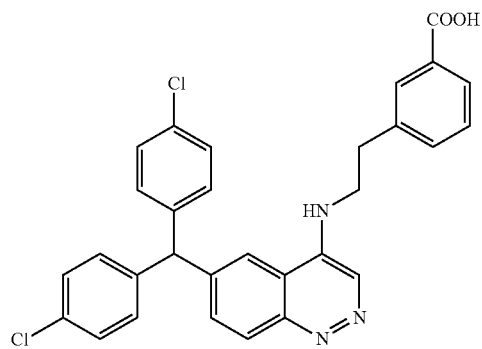 [SMILES: O=C(O)c1cccc(CCNc2cnnc3ccc(C(c4ccc(Cl)cc4)c4ccc(Cl)cc4)cc23)c1]

Step 1: Synthesis of methyl 3-(2-(6-(bis(4-chlorophenyl)methyl)cinnolin-4-ylamino)ethyl)benzoate Into a 10-mL round-bottom flask purged and maintained with an inert atmosphere of nitrogen, was placed 6-[bis(4-chlorophenyl)methyl]-4-chlorocinnoline (100 mg, 0.25 mmol, 1.00 equiv), methyl 3-(2-aminoethyl)benzoate hydrochloride (80 mg, 0.37 mmol, 1.50 equiv), Pd₂(dba)₃ (12 mg), XantPhos (24 mg), Cs₂C03 (245 mg, 0.75 mmol, 3.00 equiv) and 1,4-dioxane (2 mL). The resulting solution was stirred overnight at 90° C. The solids were filtered out. The resulting mixture was concentrated under vacuum. The resulting residue was applied onto a silica gel column with EA:PE (1:3) to yield methyl 3-[2-([6-[bis(4-chlorophenyl)methyl]cinnolin-4-yl]amino)ethyl]benzoate as a yellow solid.

LC-MS (ES, m/z): 542 [M+H]⁺

Step 2: Synthesis of 3-(2-(6-(bis(4-chlorophenyl)methyl)cinnolin-4-ylamino)ethyl)benzoic acid Into a 100-mL round-bottom flask, was placed methyl 3-[2-([6-[bis(4-chlorophenyl)methyl]cinnolin-4-yl]amino)ethyl]benzoate (80 mg, 0.15 mmol, 1.00 equiv), methanol (10 mL) and 1M sodium hydroxide (20 mL). The resulting solution was stirred overnight at 25° C. The resulting mixture was concentrated under vacuum. The pH value of the solution was adjusted to pH 3-4 with 10% HCl. The solids were collected by filtration. The resulting residue was purified by Prep-HPLC with the following conditions (1#waters2767-5): Column, SunFire Prep C18, 19*150 mm 5 umH PrepC-001(T)18600256819513816414 04; mobile phase, Phase A: water with 0.05% TFA Phase B: CH₃CN (35% CH₃CN up to 70% in 12 min, hold 95% in 1 min, down to 35% in 1 min, hold 35% in 1 min); Detector, UV220&254 nm to yield 3-[2-([6-[bis(4-chlorophenyl)methyl]cinnolin-4-yl]amino)ethyl]benzoic acid as a white solid.

LC-MS (ES, m/z): 526 [M-CF₃COOH—H]⁻

¹H-NMR (300 MHz, DMSO) δ 8.672 (s, 1H), 8.209 (s, 1H), 7.925-7.795 (m, 4H), 7.562-7.537 (m, 1H), 7.449-7.385 (m, 5H), 7.198-7.170 (m, 4H), 5.873 (s, 1H), 3.945 (t, J=6.9 Hz, 2H), 3.098 (t, J=6.9 Hz, 2H).

Synthesis Example 26

6-((4-chlorophenyl)(4-fluorophenyl)methyl)-N-(1-(trifluoromethylsulfonyl)piperidin-4-yl)cinnolin-4-amine Compound #34

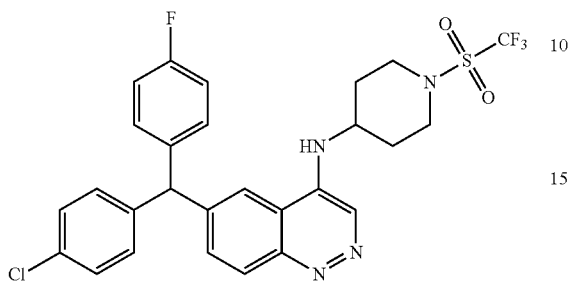

Step 1: Synthesis of 6-bromo-N-(1-(trifluoromethylsulfonyl)piperidin-4-yl)cinnolin-4-amine Into a 100-mL round-bottom flask purged and maintained with an inert atmosphere of nitrogen, was placed a solution of 6-bromo-4-chlorocinnoline (500 mg, 2.05 mmol, 1.00 equiv) in isopropanol (30 mL), 1-(trifluoromethane)sulfonylpiperidin-4-amine hydrochloride (1.11 g, 4.13 mmol, 2.00 equiv) and DIEA (3.58 mL, 10.00 equiv). The resulting solution was stirred overnight at 90° C. The resulting mixture was concentrated under vacuum. The resulting residue was dissolved in sat. sodium bicarbonate (100 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate, to yield 6-bromo-N-[1-(trifluoromethane)sulfonylpiperidin-4-yl]cinnolin-4-amine as a yellow solid.

LCMS (ES, m/z): 439 [M+H]+

Step 2: Synthesis of (4-chlorophenyl)(4-fluorophenyl)(4-(1-(trifluoromethylsulfonyl)piperidin-4-ylamino)cinnolin-6-yl)methanol Into a 50-mL 3-necked round-bottom flask purged and maintained with an inert atmosphere of nitrogen, was placed a solution of 6-bromo-N-[1-(trifluoromethane)sulfonylpiperidin-4-yl]cinnolin-4-amine (100 mg, 0.23 mmol, 1.00 equiv) in tetrahydrofuran (20 mL). To the resulting mixture was then added LiHMDS (0.46 mL, 2.00 equiv, 1M) dropwise with stirring at 0° C. The resulting solution was stirred for 30 min at 0° C. To the mixture was then added n-BuLi (0.37 mL, 4.00 equiv, 2.5M) dropwise with stirring at −78° C. The resulting solution was allowed to react, with stirring, for an additional 30 min at −78° C. To the mixture was then added (4-chlorophenyl)(4-fluorophenyl)methanone (216 mg, 0.92 mmol, 4.00 equiv, dissolved in a minimum volume of THF) dropwise with stirring at −78° C. The resulting solution was allowed to react, with stirring, for an additional 30 min at −78° C. The reaction was then warmed to room temperature slowly and quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:1) to yield (4-chlorophenyl)(4-fluorophenyl)(4-[[1-(trifluoromethane)sulfonylpiperidin-4-yl]amino]cinnolin-6-yl)methanol as a yellow solid.

Step 3: Synthesis of 6-((4-chlorophenyl)(4-fluorophenyl)methyl)-N-(1-(trifluoromethylsulfonyl)piperidin-4-yl)cinnolin-4-amine Into a 25-mL round-bottom flask, was placed a solution of (4-chlorophenyl)(4-fluorophenyl)(4-[[1-(trifluoromethane)sulfonylpiperidin-4-yl]amino]cinnolin-6-yl)methanol (100 mg, 0.17 mmol, 1.00 equiv) in dichloromethane (10 mL). To the resulting mixture was then added Et₃SiH (0.108 mL, 4.00 equiv) dropwise with stirring at 0° C. To the resulting mixture was then added trifluoroacetic acid (4.25 mL, 25.00 equiv) dropwise with stirring at 0° C. The resulting solution was stirred for 3 h at room temperature. The reaction was then quenched by the addition of sat. sodium bicarbonate (30 mL). The resulting solution was extracted with ethyl acetate (2×100 mL) and the organic layers combined and dried over anhydrous sodium sulfate. The solids were filtered out. The resulting mixture was concentrated under vacuum. The resulting residue was purified by Prep-HPLC with the following conditions (Waters2767-1): Column, X-Bridge Prep C18, 5 um, 19×100 mm; mobile phase, 0.05% NH₄HCO₃ in water and CH₃CN (35% CH₃CN to 75% in 12 min); Detector, UV 254, to yield 6-[(4-chlorophenyl)(4-fluorophenyl)methyl]-N-[1-(trifluoromethane)sulfonylpiperidin-4-yl]cinnolin-4-amine as a light yellow solid.

LCMS (ES, m/z): 579 [M+H]+

$^1$H-NMR (300 MHz, DMSO) δ 8.804 (s, 1H), 8.221 (s, 1H), 8.077 (d, J=9.0 Hz, 1H), 7.498 (d, J=9.0 Hz, 1H), 7.424-7.396 (m, 2H), 7.198-7.154 (m, 7H), 5.813 (s, 1H), 4.050 (br, 1H), 3.919-3.874 (m, 2H), 3.487-3.387 (m, 2H), 2.153-2.115 (m, 2H), 1.657-1.617 (m, 2H).

Synthesis Example 27

6-((4-chlorophenyl)(4-methoxyphenyl)methyl)-N-(1-(trifluoromethylsulfonyl)piperidin-4-yl)cinnolin-4-amine Compound #35

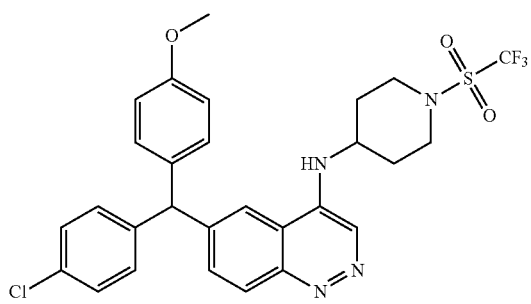 [SMILES: COc1ccc(C(c2ccc(Cl)cc2)c2ccc3nncc(NC4CCN(S(=O)(=O)C(F)(F)F)CC4)c3c2)cc1]

Step 1: Synthesis of (4-chlorophenyl)(4-methoxyphenyl)(4-(1-(trifluoromethylsulfonyl)piperidin-4-ylamino)cinnolin-6-yl)methanol Into a 50-mL 3-necked round-bottom flask purged and maintained with an inert atmosphere of nitrogen, was placed a solution of 6-bromo-N-[1-(trifluoromethane)sulfonylpiperidin-4-yl]cinnolin-4-amine (100 mg, 0.23 mmol, 1.00 equiv) in tetrahydrofuran (20 mL). To the resulting mixture was then added LiHMDS (0.46 mL, 2.00 equiv, 1M) dropwise with stirring at 0° C. The resulting solution was stirred for 20 min at 0° C. To the mixture was then added n-BuLi (0.37 mL, 4.00 equiv, 2.5M) dropwise with stirring at −78° C. The resulting solution was allowed to react, with stirring, for an additional 30 min at −78° C. To the mixture was added (4-chlorophenyl)(4-methoxyphenyl)methanone (227 mg, 0.92 mmol, 4.00 equiv, dissolved in a minimum volume of THF) dropwise with stirring at −78° C. The resulting solution was allowed to react, with stirring, for an additional 30 min at −78° C. The reaction was then warmed to room temperature slowly and quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:1) to yield (4-chlorophenyl)(4-methoxyphenyl)(4-[[1-(trifluoromethane)sulfonylpiperidin-4-yl]amino]cinnolin-6-yl)methanol as a yellow solid.

LC-MS (ES, m/z) 607 [M+H]$^+$

Step 2: Synthesis of 6-((4-chlorophenyl)(4-methoxyphenyl)methyl)-N-(1-(trifluoromethylsulfonyl)piperidin-4-yl)cinnolin-4-amine Into a 25-mL round-bottom flask, was placed a solution of (4-chlorophenyl)(4-methoxyphenyl)(4-[[1-(trifluoromethane)sulfonylpiperidin-4-yl]amino]cinnolin-6-yl)methanol (100 mg, 0.16 mmol, 1.00 equiv) in dichloromethane (10 mL). To the resulting mixture was then added Et$_3$SiH (0.102 mL, 4.00 equiv) dropwise with stirring at 0° C. To the mixture was then added trifluoroacetic acid (0.306 mL, 25.00 equiv) dropwise with stirring at 0° C. The resulting solution was stirred for 3 h at room temperature. The reaction was then quenched by the addition of sat. sodium bicarbonate (30 mL). The resulting solution was extracted with ethyl acetate (2×100 mL) and the organic layers combined and dried over anhydrous sodium sulfate. The solids were filtered out. The resulting mixture was concentrated under vacuum. The resulting residue was purified by Prep-HPLC with the following conditions (Waters2767-1): Column, X-Bridge Prep C18, 5 um, 19×100 mm; mobile phase, Phase A: water with 0.05% NH$_4$HCO$_3$ Phase B: CH$_3$CN (35% CH$_3$CN up to 95% in 12 min); Detector, UV 254, to yield 6-[(4-chlorophenyl)(4-methoxyphenyl)methyl]-N-[1-(trifluoromethane)sulfonylpiperidin-4-yl]cinnolin-4-amine as a white solid.

LC-MS (ES, m/z) 591 [M+H]$^+$ $^1$H-NMR (300 MHz, DMSO) δ 8.796 (s, 1H), 8.221 (s, 1H), 8.065 (d, J=9.0 Hz, 1H), 7.489 (d, J=9.0 Hz, 1H), 7.408-7.380 (m, 2H), 7.209-7.140 (m, 3H), 7.085-7.056 (m, 2H), 6.931-6.892 (m, 2H), 5.725 (s, 1H), 4.055 (br, 1H), 3.920-3.876 (m, 2H), 3.726 (s, 3H), 3.466-3.383 (m, 2H), 2.154-2.112 (m, 2H), 1.670-1.621 (m, 2H).

Synthesis Example 28

6-(bis(4-fluorophenyl)methyl)-N-(1-(trifluoromethylsulfonyl)piperidin-4-yl)cinnolin-4-amine Compound #33

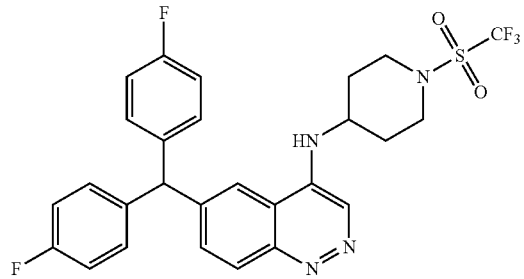 [SMILES: O=S(=O)(N1CCC(Nc2cnnc3ccc(C(c4ccc(F)cc4)c4ccc(F)cc4)cc23)CC1)C(F)(F)F]

Step 1: Synthesis of tert-butyl 4-(6-(bis(4-fluorophenyl)(hydroxy)methyl)cinnolin-4-ylamino)piperidine-1-carboxylate Into a 50-mL 3-necked round-bottom flask purged and maintained with an inert atmosphere of nitrogen, was placed a solution of tert-butyl 4-[(6-bromocinnolin-4-yl)amino]piperidine-1-carboxylate (100 mg, 0.25 mmol, 1.00 equiv) in tetrahydrofuran (20 mL). To the resulting mixture was then added LiHMDS (0.63 mL, 2.50 equiv, 1M) dropwise with stirring at 0° C. The resulting solution was stirred for 20 min at 0° C. To the mixture was then added n-BuLi (0.4 mL, 4.00 equiv, 2.5M) dropwise with stirring at −78° C. The resulting solution was allowed to react, with stirring, for an additional 30 min at −78° C. To the mixture was added bis(4-fluorophenyl)methanone (218 mg, 1.00 mmol, 4.00 equiv, dissolved in a minimum volume of THF) dropwise with stirring at −78° C. The resulting solution was allowed to react, with stirring, for an additional 1 h at −78° C. and then warmed to room temperature slowly. The reaction was then quenched by the addition of sat. sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (8:1) to yield tert-butyl 4-([6-[bis(4-fluorophenyl)(hydroxy)methyl]cinnolin-4-yl]amino)piperidine-1-carboxylate as a yellow solid.

LC-MS (ES, m/z) 547 [M+H]$^+$

Step 2: Synthesis of 6-(bis(4-fluorophenyl)methyl)-N-(piperidin-4-yl)cinnolin-4-amine Into a 25-mL round-bottom flask purged and maintained with an inert atmosphere of nitrogen, was placed a solution of tert-butyl 4-([6-[bis(4-fluorophenyl)(hydroxy)methyl]cinnolin-4-yl]amino)piperidine-1-carboxylate (100 mg, 0.18 mmol, 1.00 equiv) in dichloromethane (10 mL). To the resulting mixture was then added Et$_3$SiH (0.115 mL, 4.00 equiv) dropwise with stirring at 0° C. To this was added trifluoroacetic acid (0.345 mL, 25.00 equiv) dropwise with stirring at 0° C. The resulting solution was stirred for 3 h at room temperature. The resulting mixture was concentrated under vacuum. The resulting residue was dissolved in sat. sodium bicarbonate (30 mL). The resulting solution was extracted with ethyl acetate (2×50 mL) and the organic layers combined and dried over anhydrous sodium sulfate. The solids were collected by filtration. The resulting mixture was concentrated under vacuum to yield a residue which was used in the next step without purification.

LC-MS (ES, m/z) 431 [M+H]$^+$

Step 3: Synthesis of 6-(bis(4-fluorophenyl)methyl)-N-(1-(trifluoromethylsulfonyl)piperidin-4-yl)cinnolin-4-amine Into a 25-mL round-bottom flask purged and maintained with an inert atmosphere of nitrogen, was placed a solution of 6-[bis(4-fluorophenyl)methyl]-N-(piperidin-4-yl)cinnolin-4-amine (100 mg, 0.23 mmol, 1.00 equiv) in dichloromethane (10 mL). To the resulting mixture was then added triethylamine (0.096 mL, 3.00 equiv) dropwise with stirring at −20° C. To the mixture was then added Tf$_2$O (0.035 mL, 0.90 equiv) dropwise with stirring at −20° C. The resulting solution was stirred for 30 min at −20° C. The resulting solution was allowed to react, with stirring, for an additional 1 h at room temperature. The reaction was then quenched by the addition of sat. sodium bicarbonate (50 mL). The resulting solution was extracted with DCM (2×100 mL) and the organic layers combined and dried over anhydrous sodium sulfate. The solids were filtered out. The resulting mixture was concentrated under vacuum. The resulting residue was purified by Prep-HPLC with the following conditions (Waters2767-1): Column, X-Bridge Prep C18, 5 um, 19×100 mm; mobile phase, 0.05% NH$_4$HCO$_3$ in water and CH$_3$CN (35% CH$_3$CN to 75% in 12 min); Detector, UV 254, to yield 6-[bis(4-fluorophenyl)methyl]-N-[1-(trifluoromethane)sulfonylpiperidin-4-yl]cinnolin-4-amine as a light yellow solid.

LC-MS (ES, m/z) 563 [M+H]$^+$ $^1$H-NMR (400 MHz, DMSO) δ 8.833 (s, 1H), 8.308 (s, 1H), 8.047 (d, J=8.8 Hz, 1H), 7.840 (br, 1H), 7.593 (d, J=8.8 Hz, 1H), 7.200-7.182 (m, 8H), 5.839 (s, 1H), 4.181 (br, 1H), 3.936-3.902 (m, 2H), 3.452-3.389 (m, 2H), 2.159-2.128 (m, 2H), 1.727-1.646 (m, 2H).

Synthesis Example 29

6-((4-chlorophenyl)(thiazol-2-yl)methyl)-N-(1-(trifluoromethylsulfonyl)piperidin-4-yl)cinnolin-4-amine Compound #36

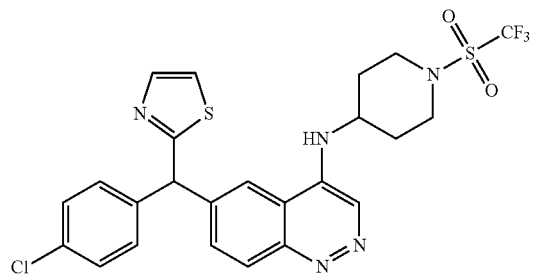 [SMILES: O=S(=O)(N1CCC(Nc2cnnc3ccc(C(c4ccc(Cl)cc4)c4nccs4)cc23)CC1)C(F)(F)F]

Into a 25-mL round-bottom flask purged and maintained with an inert atmosphere of nitrogen, was placed (4-chlorophenyl)(1,3-thiazol-2-yl)(4-[[1-(trifluoromethane)sulfonylpiperidin-4-yl]amino]cinnolin-6-yl)methanol (100 mg, 0.17 mmol, 1.00 equiv), SnCl$_2$.2H$_2$O (77 mg, 0.34 mmol, 2.00 equiv), HCl (1 mL) and AcOH (3 mL). The resulting solution was stirred for 6 h at 100° C. The reaction was then quenched by the addition of sat. sodium bicarbonate (150 mL). The resulting solution was extracted with ethyl acetate (2×200 mL) and the organic layers combined and dried over anhydrous sodium sulfate. The solids were filtered out. The resulting mixture was concentrated under vacuum. The resulting residue was purified by Prep-HPLC with the following conditions (Waters2767-1): Column, X-Bridge Prep C18, 5 um, 19×100 mm; mobile phase, Phase A: water with 0.05% NH$_4$HCO$_3$ Phase B: CH$_3$CN (35% CH$_3$CN up to 75% in 12 min); Detector, UV 254 to yield 6-[(4-chlorophenyl)(1,3-thiazol-2-yl)methyl]-N-[1-(trifluoromethane)sulfonylpiperidin-4-yl]cinnolin-4-amine as an off-white solid.

LC-MS (ES, m/z) 568 [M+H]$^+$ $^1$H-NMR (400 MHz, DMSO) δ 8.828 (s, 1H), 8.345 (s, 1H), 8.105 (d, J=8.8 Hz, 1H), 7.857-7.849 (m, 1H), 7.736-7.687 (m, 2H), 7.454-7.370 (m, 4H), 7.223 (d, J=8.0 Hz, 1H), 6.131 (s, 1H), 4.076-4.056 (m, 1H), 3.930-3.896 (m, 2H), 3.468-3.408 (m, 2H), 2.168-2.138 (m, 2H), 1.707-1.615 (m, 2H).

Additional representative compounds of formula (I) of the present invention were similarly prepared according to the procedures as described in the examples above. Table 3 below, lists said compounds and provides structures, names and measured 1H NMR and/or LCMS. More particularly, compound #2 was prepared as described in Example 1; compounds #6-9 were prepared as described in Example 8, compound #4 was prepared as described in Example 16; compound #3 was prepared as described in Example 25; and compounds #1 and 5 were prepared as described in Example 28.

TABLE 3

Additional Representative Compounds of Formula (I)

| ID No. | Structure/Name | 1H NMR and/or LCMS |
|---|---|---|
| 9 | 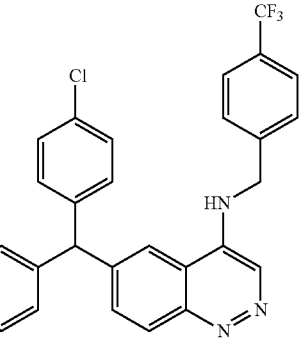<br>6-(bis(4-chlorophenyl)methyl)-N-(4-(trifluoromethyl)benzyl)cinnolin-4-amine | ¹H NMR (CHLOROFORM-d) δ: 8.51 (s, 1H), 8.22 (d, J = 8.6 Hz, 1H), 7.59 (d, J = 8.1 Hz, 2H), 7.47-7.54 (m, 2H), 7.45 (d, J = 8.1 Hz, 2H), 7.23-7.26 (m, 4H), 7.01 (d, J = 8.6 Hz, 4H), 5.85 (t, J = 5.6 Hz, 1H), 5.65 (s, 1H), 4.65 (d, J = 5.6 Hz, 2H) LCMS (ES. m/z) 538.0, 540.2 [M + H] |
| 8 | 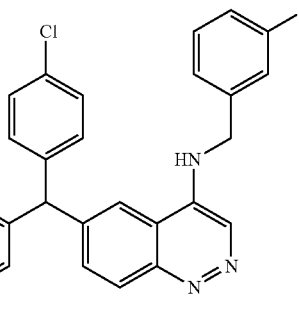<br>6-(bis(4-chlorophenyl)methyl)-N-(3-(trifluoromethyl)benzyl)cinnolin-4-amine | ¹H NMR (CHLOROFORM-d) δ: 8.55 (s, 1H), 8.23 (d, J = 9.1 Hz, 1H), 7.41-7.65 (m, 6H), 7.24-7.26 (m, 4H), 7.01 (d, J = 8.6 Hz, 4H), 5.78 (t, J = 5.3 Hz, 1H), 5.66 (s, 1H), 4.65 (d, J = 5.1 Hz, 2H) LCMS (ES. m/z) 538.0, 540.2 [M + H] |
| 7 | 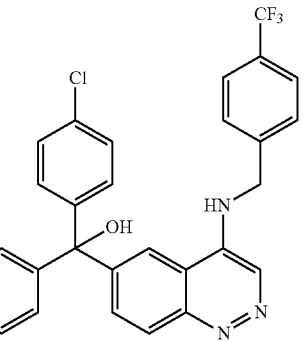<br>bis(4-chlorophenyl)(4-((4-(trifluoromethyl)benzyl)amino)cinnolin-6-yl)methanol | LCMS (ES. m/z) 554.1, 556.0 [M + H] |
| 6 | 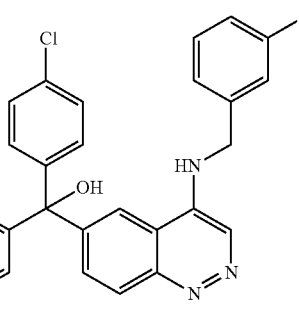 | LCMS (ES. m/z) 554.1, 556.0 [M + H] |

TABLE 3-continued

Additional Representative Compounds of Formula (I)

| ID No. | Structure/Name | 1H NMR and/or LCMS |
|---|---|---|
| | bis(4-chlorophenyl)(4-((3-(trifluoromethyl)benzyl)amino)cinnolin-6-yl)methanol | |
| 5 | 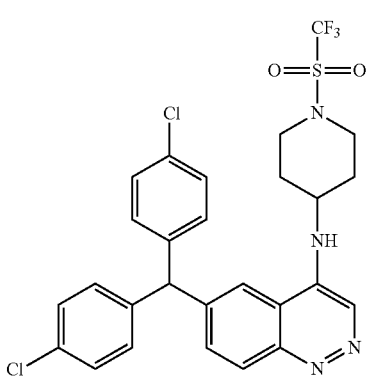 [SMILES: O=S(=O)(N1CCC(Nc2cnnc3ccc(C(c4ccc(Cl)cc4)c4ccc(Cl)cc4)cc23)CC1)C(F)(F)F]<br>6-(bis(4-chlorophenyl)methyl)-N-(1-((trifluoromethyl)sulfonyl)piperidin-4-yl)cinnolin-4-amine | ¹H NMR (CHLOROFORM-d) δ: 8.65 (s, 1H), 8.22 (d, J = 8.8 Hz, 1H), 7.55 (s, 1H), 7.48 (d, J = 8.8 Hz, 1H), 7.25 (d, J = 9.8 Hz, 4H), 6.99 (d, J = 8.3 Hz, 4H), 5.64 (s, 1H), 5.15 (br. s., 1H), 4.04 (d, J = 13.2 Hz, 2H), 3.84 (m, 1H), 3.28 (t, J = 11.7 Hz, 2H), 2.29 (d, J = 12.5 Hz, 2H), 1.63-1.77 (m, 2H)<br>LCMS (ES. m/z) 595.9, 597.2 [M + H] |
| 4 | 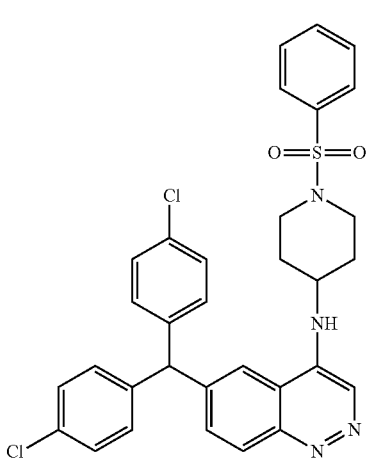 [SMILES: O=S(=O)(c1ccccc1)N1CCC(Nc2cnnc3ccc(C(c4ccc(Cl)cc4)c4ccc(Cl)cc4)cc23)CC1]<br>6-(bis(4-chlorophenyl)methyl)-N-(1-(phenylsulfonyl)piperidin-4-yl)cinnolin-4-amine | ¹H NMR (CHLOROFORM-d) δ: 8.54 (s, 1H), 8.20 (d, J = 9.1 Hz, 1H), 7.78 (d, J = 7.6 Hz, 2H), 7.62-7.71 (m, 1H), 7.53-7.62 (m, 3H), 7.44 (d, J = 8.6 Hz, 1H), 7.22 (d, J = 8.6 Hz, 4H), 6.95 (d, J = 8.1 Hz, 4H), 5.58 (s, 1H), 5.16 (d, J = 7.1 Hz, 1H), 3.91 (d, J = 11.6 Hz, 2H), 3.42-3.67 (m, 1H), 2.48 (t, J = 11.6 Hz, 2H), 2.15-2.32 (m, 2H), 1.72-1.86 (m, 2H)<br>LCMS (ES. m/z) 603.2, 605.1 [M + H] |
| 3 | 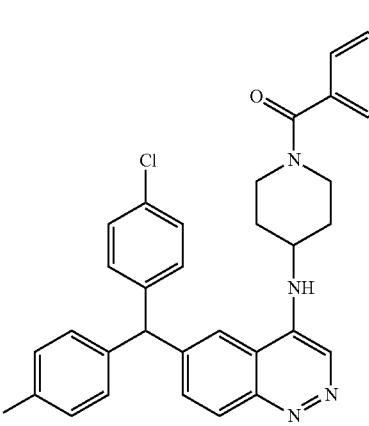<br>(4-((6-(bis(4-chlorophenyl)methyl)cinnolin-4-yl)amino)piperidin-1-yl)(phenyl)methanone | LCMS (ES. m/z) 567.2, 569.3 [M + H] |

TABLE 3-continued

Additional Representative Compounds of Formula (I)

| ID No. | Structure/Name | 1H NMR and/or LCMS |
|---|---|---|
| 2 | 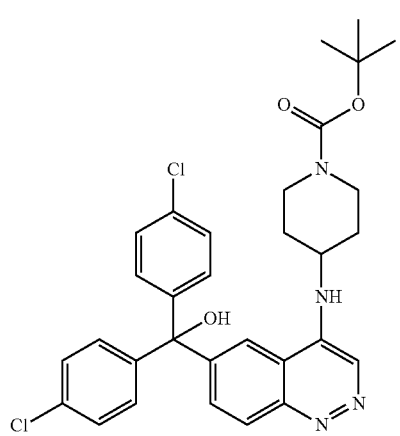 [SMILES: CC(C)(C)OC(=O)N1CCC(Nc2cnnc3ccc(C(O)(c4ccc(Cl)cc4)c4ccc(Cl)cc4)cc23)CC1]<br>tert-butyl 4-((6-(bis(4-chlorophenyl)(hydroxy)methyl)cinnolin-4-yl)amino)piperidine-1-carboxylate | LCMS (ES. m/z) 579.2, 581.3 [M + H] |
| 1 | 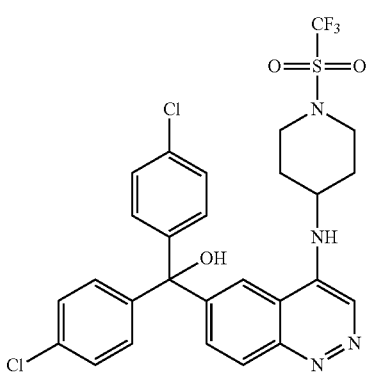 [SMILES: O=S(=O)(N1CCC(Nc2cnnc3ccc(C(O)(c4ccc(Cl)cc4)c4ccc(Cl)cc4)cc23)CC1)C(F)(F)F]<br>bis(4-chlorophenyl)(4-((1-((trifluoromethyl)sulfonyl)piperidin-4-yl)amino)cinnolin-6-yl)methanol | LCMS (ES. m/z) 611.1, 613.0 [M + H] |

BIOLOGICAL EXAMPLES $CB_1$ and $CB_2$ receptors are $G_i$-coupled GPCR. Activation of $CB_1$ and $CB_2$ receptors results in a decrease in cAMP production. An inverse agonist of the $CB_1$ or $CB_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+TBP-NHS Cryptate (supplied as part of the assay kit). The specific signal (i.e. energy transfer) is inversely proportional to the concentration of cAMP in the standard or sample.

Biological Example 1: CB-1 and CB-2 In Vitro Assay

Preparation of Cells

Human $CB_1R$ (Cannabanoid receptor 1) was stably transfected in HEK-293 cells (DiscoveRx, cat: 93-0200C1). Human $CB_2R$ (Cannabanoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/ml Hygromycin B (Invitrogen Cat#10687-010), 600 μg/mL G418 (Invitrogen Cat#10131-035), and 1×Penn/Strep (Invitrogen 15140-122). After cell expansion, aliquots were cryo-stored in media containing 5% DMSO (Pierce Cat#20684).

Plating Cells from Cryostore

One day prior to experiments media was warmed to 37° C. and the cryo-stored cells were thawed in a 37° C. water bath. The cells were then added to media (10× volume) and the mixture was centrifugated at 1000 RPM for 5 min. The supernate was removed and the cells were re-suspended in media. A sample of the cell suspension was evaluated on a Cedex XS automated cell counter (Innovatis Systems) to determine viable cells/ml. Additional media was added to the cells to achieve a final cell density of 4E5 cells/mL. The cells were then plated into 384 well PDL white solid bottom plates (Greiner, Cat#781945) at 20 μL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% $CO_2$, 95% humidity) overnight.

Preparation of Compound Plates

DMSO was added to all wells of 384 well V bottom polystyrene plate (Greiner, Cat#781280) except to columns 1 and 13, rows O and P and wells M13-M23 and N13-N23. Test compounds (60 μL, 10 mM) were added to Column 1 and 13 (A1 through N1 and A13 through L13). Test compounds were serially diluted 1/3 by transferring and mixing 20 μl sample with 40 μL DMSO. This process resulted in a plate of 26 compounds, 11 doses per compound, 10 mM to 0.5 μM.

Preparation of Control Plate

DMSO (40 μL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 μL, 10 mM) was added to O1; and 1-(2,4-dichlorophenyl)-7-[(4-fluorophenyl)methylene]-4,5, 6,7-tetrahydro-N-1-piperidinyl-1H-indazole-3-carboxamide (60 μL, 10 mM) was added to N13. The control was serially diluted 1/3 by transferring and mixing 20 μl sample with 40 μL DMSO. This process resulted 11 doses per control, 10 mM to 0.5 μM.

cAMP Assay Protocol

Cells plated the day prior to the assay in clear bottom plates were viewed on an inverse microscope to ensure confluency in the range of 60-75%.

The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma 15879) in Buffer 1; (c) 1 μM cAMP Standard (50 μM stock, Perkin Elmer Cat#AD0262) diluted in Buffer 2 and serially diluted in Buffer 2, 12 doses @½ dilutions resulting in a dose range of 1 μM to 0.5 nM; (d) d2 labelled cAMP (CisBio HTRF Detection Kit Cat #62AM4PEB reconstituted with 6 ml $dH_2O$) diluted 1/20 with lysis buffer (CisBio HTRF Detection Kit Cat #62AM4PEB); (e) anti-cAMP (CisBio HTRF Detection Kit Cat #62AM4PEB reconstituted with 5 ml $dH_2O$) diluted 1/20 with lysis buffer (CisBio HTRF Detection Kit Cat #62AM4PEB); and (f) Forskolin (Sigma Cat#F6886, 10 mM in DMSO) diluted first in DMSO to 1 mM and then to 1.5 μM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 μl per well). Media as "dumped" from the cell plate and 30 μL Buffer 1 was added to each well using a Multidrop. The content of the cell plate was again "dumped" and 10 μL Buffer 2 was added to each well using a Flexdrop. 12.5 nL test compound dilutions or control compound dilutions (10 mM to 0.5 μM) were added to the cell plate using an ECHO 555 (Labcyte). The cell plate was mixed (Speed 6, Lab-Line Instruments Titer Plate Shaker) and centrifugated (1000 RPMs, 1 min). Using the Flexdrop, 2 μl additions were made into the cell plate: Buffer 2 was added to Column 24; and, 1.5 μM Forskolin was added to columns 1 through 23. Final volume of the cell plate was 12 μl with 250 nM Forskolin in all wells except column 12, and serial dilutions of test compound or control ranging from 10 μM to 0.5 nM. The cell plate was again mixed (speed 6) and centrifugated (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 μL d2 labelled cAMP and 6 μL of Anti-cAMP were added to all wells of the cell plate using a BioMek FX (Beckman Coulter). The cell plate was again mixed (speed 6) and centrifugated (1000 RPMs, 1 min) and was incubated for 60 minutes in the dark at room Temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence x 10,000 (Normalized signal (NS)). Amount of cAMP in nM was calculated for each well (based on NS) from a cAMP standard curve located on each plate (at P1-12 and P13-24). $EC_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of formula (I) of the present invention were tested for activity against the CB-1 and CB-2 receptors, according to assay protocol as outlined in Biological Example 1, with $EC_{50}$ results (in micromolar) as listed in Tables 3, below. Where a compound was tested more than once, the result presented below represents a mean of the individual measurements.

TABLE 3

Biological Activity Against CB-1 and CB-2 Receptors

| ID No | CB-1 $EC_{50}$ (μM) | CB-2 $EC_{50}$ (μM) |
| --- | --- | --- |
| 1 | 0.455 | >10 |
| 2 | 0.200 | >10 |
| 3 | 0.463 | >10 |
| 4 | 0.035 | >10 |
| 5 | 0.013 | 3.347 |
| 6 | 0.254 | >10 |
| 7 | 0.219 | >10 |
| 8 | 0.012 | >10 |
| 9 | 0.040 | >10 |
| 10 | 0.302 | 1.476 |
| 11 | 0.181 | 5.252 |
| 12 | 0.302 | 6.500 |
| 13 | 1.442 | >10 |
| 14 | 1.284 | 5.600 |
| 15 | 0.399 | 3.691 |
| 16 | 0.262 | 2.145 |
| 17 | 10.100 | 8.100 |
| 18 | 9.499 | 9.899 |
| 19 | 5.944 | >10 |
| 20 | 0.196 | 3.579 |
| 21 | 1.155 | 5.929 |
| 22 | 6.545 | >10 |
| 23 | 5.094 | >10 |
| 24 | 0.261 | >10 |
| 25 | 0.035 | 2.465 |
| 26 | 0.095 | 1.929 |
| 27 | 0.272 | 0.849 |
| 28 | 1.688 | >10 |
| 29 | 0.099 | >10 |
| 30 | 0.643 | >10 |
| 31 | 6.640 | >10 |
| 32 | 0.040 | 1.980 |

TABLE 3-continued

Biological Activity Against CB-1 and CB-2 Receptors

| ID No | CB-1 EC$_{50}$ (μM) | CB-2 EC$_{50}$ (μM) |
|---|---|---|
| 33 | 0.079 | 4.698 |
| 34 | 0.030 | >10 |
| 35 | 0.011 | 0.396 |
| 36 | 0.028 | 0.665 |
| 37 | 5.400 | 2.793 |
| 38 | 4.505 | 3.980 |

Biological Example 2

CB-1 & CB-2 Receptor Binding Assay—Prophetic Example

Experimental Procedure CB-1 Membrane Binding:

Into Greiner V bottom polypropylene plates, hCB1-CHO-K1 membranes (2 μg/well final concentration) in assay buffer (50 mM Tris-HCl pH 7.4, 5 mM MgCl$_2$ and 0.5 mg/ml (0.05%) Ultra fatty acid free BSA) are dispensed. Membranes are purchased from Perkin Elmer. Test compounds are then added to each well and then [$^3$H] CP 55, 940 (0.4 nM final well concentration) in assay buffer (50 mM Tris-HCl pH 7.4, 5 mM MgCl$_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed seven times with ice cold rinse buffer. Filter plates are then dried overnight at room temperature. The next day, plate bottoms are sealed with plate tape and 15 μl MicroScint 20 is added to each well. Plates are incubated for 2 h and radioactivity is measured by Topcount.

Experimental Procedure CB-2 Membrane Binding—Prophetic Example:

Into Greiner V bottom polypropylene plates, hCB2-HEK293 membranes (2 μg/well final concentration) in assay buffer (50 mM Tris-HCl pH 7.4, 5 mM MgCl$_2$ and 0.5 mg/ml (0.05%) Ultra fatty acid free BSA) are dispensed. Membranes are prepared as described in FELDER, C. C., et al., *Molecular Pharmacology*, 1992, pp 838-845, Vol. 42. Test compounds are then added to each well and then [$^3$H] CP 55, 940 (0.5 nM final well concentration) in assay buffer (50 mM Tris-HCl pH 7.4, 5 mM MgCl$_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed nine times with ice cold rinse buffer. Filter plates are then dried overnight at room temperature. The next day, plate bottoms are sealed with plate tape and 15 ul MicroScint 20 is added to each well. Plates are incubated for 2 h and radioactivity is measured by Topcount.

Total Binding:

Total Binding levels are achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):

Non-Specific Binding (NSB) levels are achieved by combining membrane, 10 μM final concentration WIN-55,212 (also known as (R)-(+)-[2,3-dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H] CP-55,940 (also known as 5-(1,1-dimethylheptyl)-2-[(1R,2R,5R)-5-hydroxy-2-(3-hydroxypropyl)cyclohexyl]-phenol).

Data Analysis:

Top Count raw data files are used for data analysis as follows:

Non-specific binding (NSB=10 μM WIN-55,212+Membrane+[$^3$H] CP-55,940) was used as the negative control, while the Total Binding (TB=DMSO+Membrane+[$^3$H] CP-55,940) is used as the positive control.

Excel data file reports are generated by the PE TopCount and imported into Excel for calculations or were imported into a macro driven Excel template maintained by Lead Generation—Biology.

IC$_{50}$ data is calculated using raw CPM values. Curves are fitted individually from singlet 11 point dosing curves+1% DMSO Control. IC$_{50}$ values re fit appropriately and calculated using the following equation:

$$v = V_{min} + \frac{V_0 - V_{min}}{1 + ([I]/IC_{50})^h}$$

V$_{min}$, CPM at maximum inhibition; V$_o$, CPM at zero inhibition; IC$_{50}$, inhibitor concentration at 50% inhibition; h, Hill coefficient.

Maximal compound % inhibition of control treated wells is also noted since some compounds may exhibit values suitable for calculating IC$_{50}$'s.

% Inhibition of Total Binding=(1−(CPM Compound Treated Well/CPM Control Treated Well))*100

In Vivo Biological Assays—Prophetic Examples
Animals, Diets and Test Compound:

Male 14-20-week old diet-induced obese mice are ordered from Taconic. Mice were started on a 60% fat diet (D12492, Research Diets, New Brunswick, N.J.) at 6 weeks of age. Mice are single-housed.

Male Sprague Dawley rats are ordered from Charles River (225-250 gm upon arrival). They are fed standard chow diet (Purina 5001) and housed 2 per cage. Male C57bl/6j mice are ordered from Charles River at 22-25 g and housed 3 per cage. They are fed standard chow (Purina 5001). All animals are housed in a temperature-controlled room with 12-hour light/dark cycle. Animals are given food and water ad libitum, except as noted.

Test compounds are formulated in 10% PEG400 and 10% solutol. Test compounds are administered by oral gavage (5 ml kg$^{-1}$).

Biological Example 3: Mouse Fast
PK/BBB—Prophetic Example

Male C57bl/6j mice are dosed with test compounds at 30 mg/kg. Plasma is collected via retro-orbital bleeding at 1 hr and 4 hrs after dosing. Whole brain without cerebellum is collected at 4 hrs after dosing. Wet brain weight is recorded before freezing. Brains are homogenized in saline and sent for analysis for determination of concentration of test compound.

Biological Example 4: Chronic DIO
Mouse—Prophetic Example

The test compound is formulated in 10% PEG400 and 10% solutol. DIO mice receive vehicle, test compound (@1, 3 and 10 mg/kg) daily for 26 days. At the end of the experiment, the mice are euthanized and blood and tissues are collected.

Body weight and food weight (food intake) are monitored daily for days 1-5 and twice weekly thereafter. Fed blood glucose is measured weekly. An insulin tolerance test (0.5 U/kg Humulin, ip) is performed on day 19 after a 4 hour food removal. Blood glucose is measured at 0, 15, 30, 60 and 120 minutes after insulin. After an overnight fast, an oral glucose tolerance test (2 g/kg glucose) is performed on day 23. Blood glucose is measured at 0, 30, 60 and 120 minutes after glucose challenge. Blood glucose is measured from the tail vein with a Lifescan glucometer. Plasma insulin is measured with an ELISA or HTRF kit (Cisbio). Plasma parameters are measured with an Olympus clinical chemistry analyzer.

Biological Example 5: Open Field Locomotor Activity in Rats (CNS Activity)—Prophetic Example Male SD rats are weighed and transferred to the Activity Chambers with access to water. After a 2-hr acclimation period, the rats are dosed with vehicle or test compound (@3 and 10 mg/kg). The Activity Chamber monitoring software program is initiated and automatically records rat activity in each chamber for a period of 4 hours. At the end of the 4 hour monitoring period, the software is stopped and the rats are removed from the activity chambers. The rats are anesthetized and blood samples are obtained via retro-orbital puncture to determine plasma concentration of compounds. The rats are immediately euthanized with $CO_2$ and the brains are removed, washed with PBS, frozen on dry ice and stored at −80° C. for receptor occupancy (RO) analysis.

Satellite groups of 3 rats are dosed with test compound at 3 mg/kg and 10 mg/kg respectively. Four hours later, the rats are anesthetized. Blood is collected from these rats and then perfused with 400 ml heparinized saline through the left ventricle of the heart. The brains are removed and homogenized in PBS (4 ml/gm tissue). The samples are submitted for determination of plasma and brain compound levels.

Formulation Example 1—Prophetic Example

Solid, Oral Dosage Form

As a specific embodiment of an oral composition, 100 mg of the Compound #34, prepared as in Example 26, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

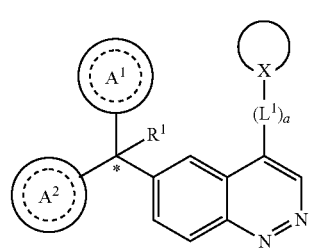

wherein
$R^1$ is selected from the group consisting of hydrogen and hydroxy;

is selected from the group consisting of phenyl, furyl, thienyl, thiazolyl, benzothiazolyl and benzo[d][1,3]dioxolyl;
wherein the phenyl, furyl, thienyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^A R^B$; wherein $R^A$ and $R^B$ are each independently selected from the group consisting of hydrogen and $C_{1-4}$alkyl; provided that each substituent is bound to a carbon atom of the ring;

is selected from the group consisting of phenyl, furyl, thienyl, thiazolyl, benzothiazolyl and benzo[d][1,3]dioxolyl;
wherein the phenyl, furyl, thienyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^C R^D$; wherein $R^C$ and $R^D$ are each independently selected from the group consisting of hydrogen and $C_{1-4}$alkyl; provided that each substituent is bound to a carbon atom of the ring;
a is an integer from 0 to 1;
$L^1$ is selected from the group consisting of $N(R^2)$—, —$N(R^2)$—$CH_2$— and $N(R^2)$—$CH_2CH_2$—; wherein $R^2$ is selected from the group consisting of hydrogen and $C_{1-2}$alkyl; and wherein the $L^1$ is bound to the cinnoline core through a nitrogen atom;

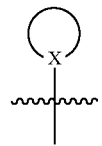

is selected from the group consisting of

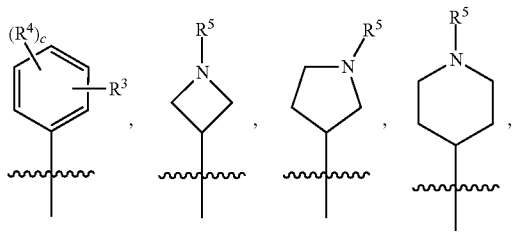

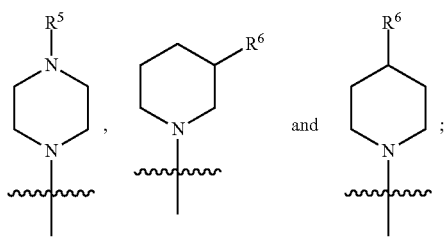

provided that when

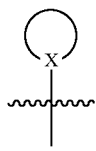

is selected from the group consisting of

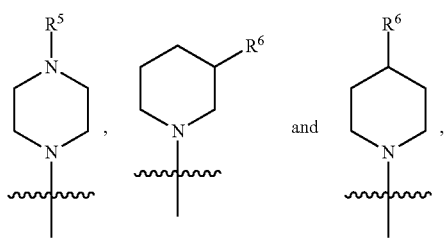

then a is 0 or a is 1 and $L^1$ is other than —N($R^2$) and —N($R^2$)—$CH_2$—;

wherein $R^3$ is selected from the group consisting of hydrogen, halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —$CO_2$H, —C(O)O—($C_{1-4}$alkyl), —($C_{1-4}$alkyl)-$CO_2$H, —($C_{1-4}$alkyl)-C(O)O—($C_{1-4}$alkyl), —$SO_2$—($C_{1-4}$alkyl) and —$SO_2$-(halogenated $C_{1-4}$alkyl);

c is an integer from 0 to 2;

each $R^4$ is independently selected from the group consisting of halogen, $C_{1-4}$alkyl, halogenated $C_{1-2}$alkyl, $C_{1-4}$alkoxy and halogenated $C_{1-2}$alkoxy;

wherein $R^5$ is selected from the group consisting of —C(O)—($C_{1-4}$alkyl), —C(O)O—($C_{1-4}$alkyl), —$SO_2$—($C_{1-4}$ alkyl) and —$SO_2$-(halogenated $C_{1-4}$ alkyl); and

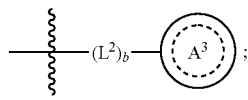

wherein $R^6$ is selected from the group consisting of $C_{1-4}$ alkyl, halogenated $C_{1-4}$alkyl, —C(O)—$NR^{E1}R^F$, —$NR^E$—C(O)—($C_{1-4}$alkyl), —$NR^E$—$SO_2$—($C_{1-4}$ alkyl), and

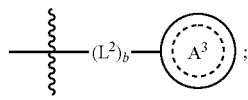

wherein $R^E$ and $R^F$ are each independently selected from the group consisting of hydrogen, methyl and ethyl;

b is an integer from 0 to 1;

$L^2$ is selected from the group consisting of —$CH_2$—, —$CH_2CH_2$—, —NH—, —N($CH_3$)—, —C(O)— and —$SO_2$—;

provided that when

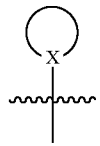

is selected from the group consisting of

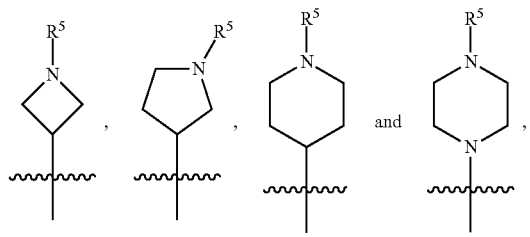

then b is 0 or b is 1 and $L^2$ is other than —NH— or —N($CH_3$)—;

is selected from the group consisting of phenyl, furan-2-yl, thien-2-yl;

wherein the phenyl is optionally substituted with a substituent selected from the group consisting of halogen, hydroxy, cyano, $C_{1-4}$alkyl, halogenated $C_{1-4}$alkyl, hydroxy substituted $C_{1-4}$ alkyl, $C_{1-4}$alkoxy, halogenated $C_{1-4}$alkoxy, —$CO_2$H, —C(O)O—($C_{1-4}$alkyl), —($C_{1-4}$alkyl)-$CO_2$H, —($C_{1-4}$alkyl)-C(O)O—($C_{1-4}$ alkyl), —$SO_2$—($C_{1-4}$alkyl) and —$SO_2$-(halogenated $C_{1-4}$alkyl); and wherein the phenyl is further optionally substituted with one to two additional substituents independently selected from the group consisting of halogen, $C_{1-4}$alkyl, halogenated $C_{1-2}$alkyl, $C_{1-4}$alkoxy and halogenated $C_{1-2}$alkoxy;

and wherein the furan-2-yl or thien-2-yl is optionally substituted with a substituent selected from the group consisting of halogen, $C_{1-4}$alkyl, halogenated $C_{1-4}$alkyl, $C_{1-4}$alkoxy, halogenated $C_{1-4}$alkoxy, —$CO_2H$, —C(O)O—($C_{1-4}$alkyl) and —C(O)—$NR^GR^H$; wherein $R^G$ and $R^H$ are each independently selected from the group consisting of hydrogen, methyl and ethyl;

or a stereoisomer, tautomer or pharmaceutically acceptable salt thereof.

2. A compound as in claim 1, wherein
$R^1$ is selected from the group consisting of hydrogen and hydroxy;

is selected from the group consisting of phenyl, furyl, thienyl and thiazolyl;

wherein the phenyl, furyl, thienyl or thiazolyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, C(O)O—$C_{1-4}$alkyl and $NR^AR^B$; wherein $R^A$ and $R^B$ are each independently selected from the group consisting of hydrogen and $C_{1-2}$alkyl; provided that each substituent is bound to a carbon atom of the ring;

is selected from the group consisting of phenyl, furyl, thienyl and thiazolyl;

wherein the phenyl, furyl, thienyl or thiazolyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, cyano, —C(O)OH, C(O)O—$C_{1-4}$alkyl and $NR^AR^B$; wherein $R^A$ and $R^B$ are each independently selected from the group consisting of hydrogen and $C_{1-2}$alkyl; provided that each substituent is bound to a carbon atom of the ring;

a is an integer from 0 to 1;

$L^1$ is selected from the group consisting of —$N(R^2)$—, —$N(R^2)$—$CH_2$— and —$N(R^2)$—$CH_2CH_2$—; wherein $R^2$ is selected from the group consisting of hydrogen and methyl; and wherein the $L^1$ is bound to the cinnoline core through a nitrogen atom;

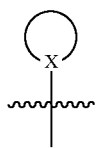

is selected from the group consisting of

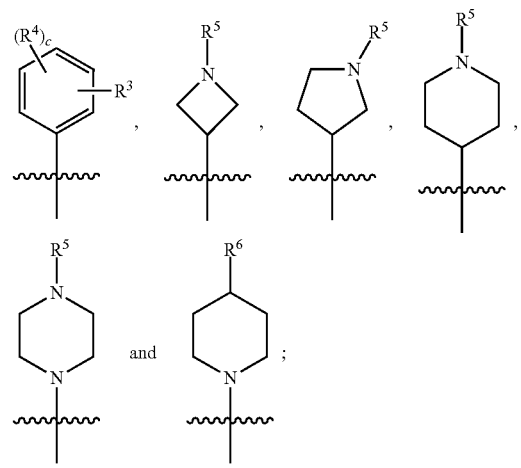

provided that when

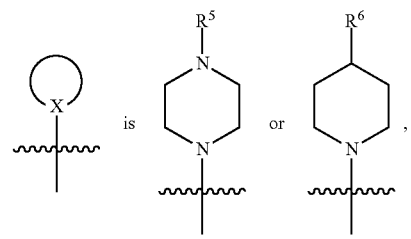

then a is 0 or a is 1 and $L^1$ is other than —NH— and —NH—$CH_2$— wherein $R^3$ is selected from the group consisting of halogen, hydroxy, cyano, $C_{1-4}$alkyl, fluorinated $C_{1-4}$alkyl, hydroxy substituted $C_{1-1}$alkyl, $C_{1-4}$alkoxy, fluorinated $C_{1-2}$alkoxy, —$CO_2H$, —C(O)O—($C_{1-4}$alkyl), —$SO_2$—($C_{1-4}$alkyl) and —$SO_2$-(fluorinated $C_{1-2}$alkyl);

c is an integer from 0 to 1;

$R^4$ is independently selected from the group consisting of halogen, $C_{1-4}$alkyl, fluorinated $C_{1-2}$alkyl, $C_{1-4}$alkoxy and fluorinated $C_{1-2}$alkoxy;

wherein $R^5$ is selected from the group consisting of —C(O)—($C_{1-2}$alkyl), —C(O)O—($C_{1-4}$alkyl), —$SO_2$—($C_{1-2}$alkyl) and —$SO_2$-(fluorinated $C_{1-2}$alkyl); and

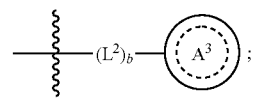

wherein $R^6$ is selected from the group consisting of $C_{1-4}$alkyl, fluorinated $C_{1-2}$alkyl, —C(O)—$NR^ER^F$, —$NR^E$—C(O)—($C_{1-4}$alkyl), —$NR^E$—$SO_2$—($C_{1-4}$alkyl), and

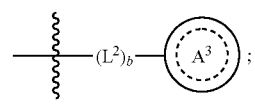

wherein $R^E$ and $R^F$ are each independently selected from the group consisting of hydrogen and methyl;

b is an integer from 0 to 1;

$L^2$ is selected from the group consisting of —CH$_2$—, —CH$_2$CH$_2$—, —NH—, —N(CH$_3$)—, —C(O)— and —SO$_2$—;

provided that when

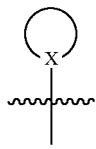

is selected from the group consisting of

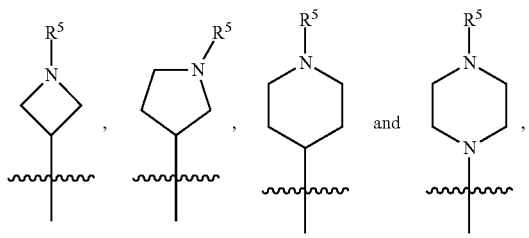

then b is 0 or b is 1 and $L^2$ is other than —NH— or —N(CH$_3$)—;

is selected from the group consisting of phenyl, furan-2-yl, thien-2-yl;

wherein the phenyl is optionally substituted with a substituent selected from the group consisting of halogen, hydroxy, cyano, C$_{1-4}$alkyl, fluorinated C$_{1-2}$alkyl, hydroxy substituted C$_{1-2}$alkyl, C$_{1-4}$alkoxy, fluorinated C$_{1-2}$alkoxy, —CO$_2$H, —C(O)O—(C$_{1-4}$alkyl), —SO$_2$—(C$_{1-4}$alkyl) and —SO$_2$-(fluorinated C$_{1-2}$alkyl); and wherein the phenyl is further optionally substituted with one to two additional substituents independently selected from the group consisting of halogen, C$_{1-4}$alkyl, fluorinated C$_{1-2}$alkyl, C$_{1-4}$alkoxy and fluorinated C$_{1-2}$alkoxy;

and wherein the furan-2-yl or thien-2-yl is optionally substituted with a substituent selected from the group consisting of halogen, C$_{1-4}$alkyl, fluorinated C$_{1-2}$alkyl, C$_{1-4}$alkoxy, fluorinated C$_{1-2}$alkoxy, —CO$_2$H, —C(O)O—(C$_{1-4}$alkyl) and —C(O)—NR$^G$R$^H$; wherein R$^G$ and R$^H$ are each independently selected from the group consisting of hydrogen and methyl;

or a stereoisomer, tautomer or pharmaceutically acceptable salt thereof.

3. A compound as in claim 2, wherein $R^1$ is selected from the group consisting of hydrogen and hydroxy;

is selected from the group consisting of phenyl and thiazol-2-yl; wherein the phenyl is optionally substituted with a substituent selected from the group consisting of halogen and C$_{1-2}$alkoxy;

is phenyl; wherein the phenyl is optionally substituted with a substituent selected from the group consisting of halogen;

a is an integer from 0 to 1;

$L^1$ is selected from the group consisting of —NH—, —NH—CH$_2$— and —NH—CH$_2$CH$_2$—; wherein the $L^1$ is bound to the cinnoline core through a nitrogen atom;

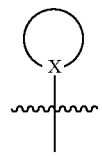

is selected from the group consisting of

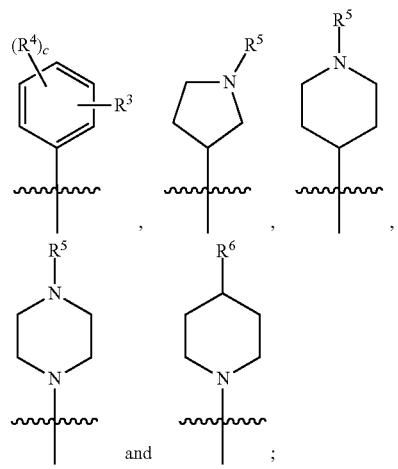

provided that when

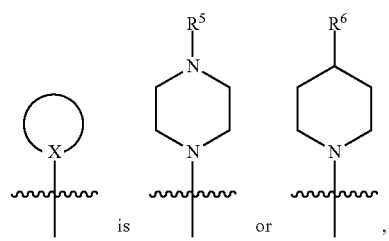

then a is 0 or a is 1 and $L^1$ is other than —NH— and —NH—CH$_2$—

$R^3$ is selected from the group consisting of hydroxy, fluorinated C$_{1-2}$alkyl, C$_{1-2}$alkoxy and carboxy;

c is 0;

$R^5$ is selected from the group consisting of —C(O)O—(C$_{1-4}$alkyl), —SO$_2$-(fluorinated C$_{1-2}$alkyl) and

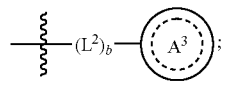

$R^6$ is

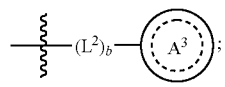

b is an integer from 0 to 1;

$L^2$ is selected from the group consisting of —CH$_2$—, —CH$_2$CH$_2$—, —NH—, —C(O)— and —SO$_2$—;

provided that when

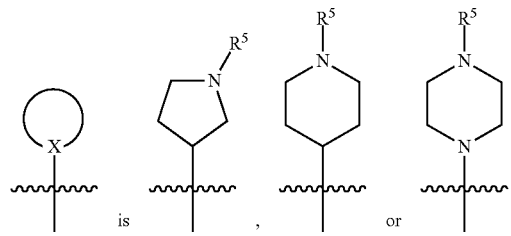

then b is 0 or b is 1 and $L^2$ is other than —NH—;

is selected from the group consisting of phenyl, furan-2-yl and thien-2-yl; wherein the phenyl, furan-2-yl or thien-2-yl is optionally substituted with carboxy;

or a stereoisomer, tautomer or pharmaceutically acceptable salt thereof.

4. A compound as in claim 3, wherein $R^1$ is selected from the group consisting of hydrogen and hydroxy;

is selected from the group consisting of 4-chlorophenyl, 4-fluorophenyl, 4-methoxyphenyl and thiazol-2-yl;

is selected from the group consisting of 4-chlorophenyl and 4-fluorophenyl;

a is an integer from 0 to 1;

$L^1$ is selected from the group consisting of —NH—, —NH—CH$_2$— and —NH—CH$_2$CH$_2$—; wherein the $L^1$ is bound to the cinnoline core through a nitrogen atom;

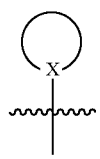

is selected from the group consisting of

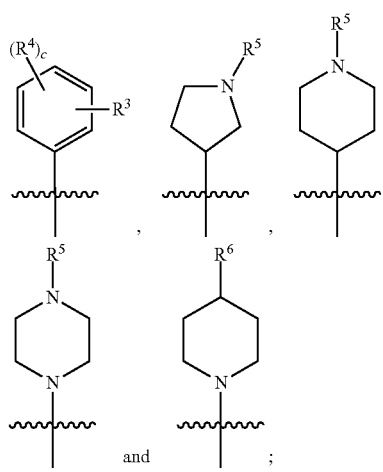

provided that when

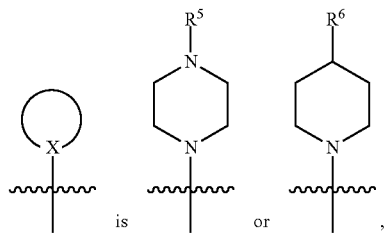

then a is 0 or a is 1 and $L^1$ is other than —NH— and —NH—CH$_2$—

$R^3$ is selected from the group consisting of hydroxy, trifluoromethyl, methoxy and carboxy;

c is 0;

$R^5$ is selected from the group consisting of t-butoxycarbonyl-, trifluoromethyl-sulfonyl- and

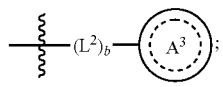

$R^6$ is

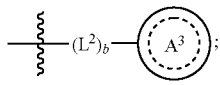

b is an integer from 0 to 1;
$L^2$ is selected from the group consisting of —CH$_2$—, —CH$_2$CH$_2$—, —NH—, —C(O)— and —SO$_2$—;
provided that when

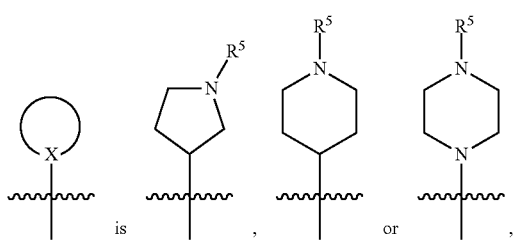

then b is 0 or b is 1 and $L^2$ is other than —NH—;

is selected from the group consisting of phenyl, furan-2-yl and thien-2-yl; wherein the phenyl, furan-2-yl or thien-2-yl is optionally substituted with carboxy;

or a stereoisomer, tautomer or pharmaceutically acceptable salt thereof.

5. A compound as in claim 1, wherein
$R^1$ is selected from the group consisting of hydrogen and hydroxy;

is selected from the group consisting of 4-chlorophenyl, 4-fluorophenyl, 4-methoxyphenyl and thiazol-2-yl;

is selected from the group consisting of 4-chlorophenyl and 4-fluorophenyl;
a is an integer from 0 to 1;
$L^1$ is selected from the group consisting of —NH—, —NH—CH$_2$— and —NH—CH$_2$CH$_2$—; wherein the $L^1$ is bound to the cinnoline core through a nitrogen atom;

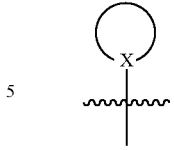

is selected from the group consisting of phenyl, 3-(trifluoromethyl)-phenyl, 4-(trifluoromethyl)-phenyl, 4-methoxyphenyl, 4-hydroxy-phenyl, 3-carboxy-phenyl, 4-carboxy-phenyl, 1-(t-butoxycarbonyl)-piperidin-4-yl, 1-(trifluoromethyl-sulfonyl)-piperidin-4-yl, 4-(trifluoromethyl-sulfonyl)-piperazin-1-yl, 1-(trifluoromethyl-sulfonyl)-pyrrolidin-3-yl, 1-(phenyl-sulfonyl)-pyrrolidin-3-yl, 1-(phenyl-methyl)-pyrrolidin-3-yl, 1-(4-carboxy-phenyl)-piperidin-4-yl, 1-(phenyl-carbonyl)-piperidin-4-yl, 1-(phenyl-sulfonyl)-piperidin-4-yl, 1-((2-carboxy-phenyl)-sulfonyl)-piperidin-4-yl, 1-((3-carboxy-phenyl)-sulfonyl)-piperidin-4-yl, 1-((4-carboxy-phenyl-sulfonyl)-piperidin-4-yl, 1-((2-carboxy-phenyl)-methyl)-piperidin-4-yl, 1-((3-carboxy-phenyl)-methyl)-piperidin-4-yl, 1-((4-carboxy-phenyl)-methyl)-piperidin-4-yl, 1-(phenyl-ethyl)-piperidin-4-yl, 1-((3-carboxy-phenyl)-ethyl)-piperidin-4-yl, 1-((4-carboxy-phenyl)-ethyl)-piperidin-4-yl, 1-((5-carboxy-furan-2-yl)-sulfonyl)-piperidin-4-yl, 1-((5-carboxy-thien-2-yl)-sulfonyl)-piperidin-4-yl, 1-((5-carboxy-thien-2-yl)-methyl)-piperidin-4-yl, 1-((4-carboxy-thien-2-yl)-sulfonyl)-piperidin-4-yl, 1-(phenyl-methyl)-piperazin-1-yl and 1-(phenyl-amino)-piperidin-1-yl;
provided that when

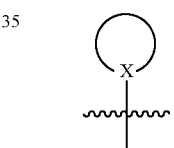

is selected from the group consisting of 4-(trifluoromethyl-sulfonyl)-piperazin-1-yl, 1-(phenyl-methyl)-piperazin-1-yl and 1-(phenyl-amino)-piperidin-1-yl, then a is 0;

or a stereoisomer, tautomer or pharmaceutically acceptable salt thereof.

6. A compound as in claim 5, wherein
$R^1$ is selected from the group consisting of hydrogen and hydroxy;

is selected from the group consisting of 4-chlorophenyl, 4-fluorophenyl, 4-methoxyphenyl and thiazol-2-yl;

is selected from the group consisting of 4-chlorophenyl and 4-fluorophenyl;
a is an integer from 0 to 1;

$L^1$ is selected from the group consisting of —NH—, —NH—CH$_2$— and —NH—CH$_2$CH$_2$—; wherein the $L^1$ is bound to the cinnoline core through a nitrogen atom;

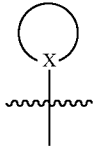

is selected from the group consisting of phenyl, 3-(trifluoromethyl)-phenyl, 4-(trifluoromethyl)-phenyl, 4-methoxyphenyl, 1-(t-butoxycarbonyl)-piperidin-4-yl, 1-(trifluoromethyl-sulfonyl)-piperidin-4-yl, 4-(trifluoromethyl-sulfonyl)-piperazin-1-yl, 1-(trifluoromethyl-sulfonyl)-pyrrolidin-3-yl, 1-(phenyl-sulfonyl)-pyrrolidin-3-yl, 1-(phenyl-carbonyl)-piperidin-4-yl, 1-(phenyl-sulfonyl)-piperidin-4-yl, 1-((3-carboxy-phenyl)-sulfonyl)-piperidin-4-yl, 1-((4-carboxy-phenyl-sulfonyl)-piperidin-4-yl, 1-((3-carboxy-phenyl)-methyl)-piperidin-4-yl, 1-((5-carboxy-thien-2-yl)-sulfonyl)-piperidin-4-yl, 1-((5-carboxy-thien-2-yl)-methyl)-piperidin-4-yl, 1-((4-carboxy-thien-2-yl)-sulfonyl)-piperidin-4-yl and 1-(phenyl-amino)-piperidin-1-yl;
provided that when

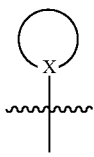

is selected from the group consisting of 4-(trifluoromethyl-sulfonyl)-piperazin-1-yl and 1-(phenyl-amino)-piperidin-1-yl, then a is 0;
or a stereoisomer, tautomer or pharmaceutically acceptable salt thereof.

7. A compound as in claim 5, wherein
$R^1$ is selected from the group consisting of hydrogen and hydroxy;

is selected from the group consisting of 4-chlorophenyl, 4-fluorophenyl, 4-methoxyphenyl and thiazol-2-yl;

is selected from the group consisting of 4-chlorophenyl and 4-fluorophenyl;
a is an integer from 0 to 1;
$L^1$ is selected from the group consisting of —NH—, —NH—CH$_2$— and —NH—CH$_2$CH$_2$—; wherein the $L^1$ is bound to the cinnoline core through a nitrogen atom;

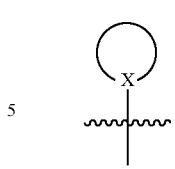

is selected from the group consisting of phenyl, 3-(trifluoromethyl)-phenyl, 4-(trifluoromethyl)-phenyl, 4-methoxyphenyl, 1-(t-butoxycarbonyl)-piperidin-4-yl, 1-(trifluoromethyl-sulfonyl)-piperidin-4-yl, 1-(trifluoromethyl-sulfonyl)-pyrrolidin-3-yl, 1-(phenyl-sulfonyl)-piperidin-4-yl, 1-((3-carboxy-phenyl)-sulfonyl)-piperidin-4-yl, 1-((4-carboxy-thien-2-yl)-sulfonyl)-piperidin-4-yl, and 1-(phenyl-amino)-piperidin-1-yl; provided that when

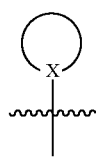

is 1-(phenyl-amino)-piperidin-1-yl, then a is 0;
or a stereoisomer, tautomer or pharmaceutically acceptable salt thereof.

8. A compound as in claim 5, wherein
$R^1$ is hydrogen;

is selected from the group consisting of 4-chlorophenyl, 4-fluorophenyl, 4-methoxyphenyl and thiazol-2-yl;

is selected from the group consisting of 4-chlorophenyl and 4-fluorophenyl;
a is an integer from 0 to 1;
$L^1$ is selected from the group consisting of —NH—, —NH—CH$_2$— and —NH—CH$_2$CH$_2$—; wherein the $L^1$ is bound to the cinnoline core through a nitrogen atom;

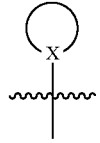

is selected from the group consisting of phenyl, 3-(trifluoromethyl)-phenyl, 4-(trifluoro-methyl)-phenyl, 1-(trifluoromethyl-sulfonyl)-piperidin-4-yl, 1-(trifluoro-methyl-sulfonyl)-pyrrolidin-3-yl, 1-(phenyl-sulfonyl)-piperidin-4-yl, 1-(4-carboxy-thien-2-yl)-sulfonyl)-piperidin-4-yl and 4-(phenyl-amino)-piperidin-1-yl;
or a stereoisomer, tautomer or pharmaceutically acceptable salt thereof.

9. A compound as in claim 5, wherein
R¹ is hydrogen;

is selected from the group consisting of 4-chlorophenyl, 4-fluorophenyl, and thiazol-2-yl;

is 4-chlorophenyl; a is 1; L¹ is selected from the group consisting of —NH— and —NH—CH₂—; wherein the L¹ is bound to the cinnoline core through a nitrogen atom;

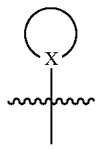

is selected from the group consisting of 3-(trifluoromethyl)-phenyl; 1-(trifluoromethyl-sulfonyl)-piperidin-4-yl and 1-((4-carboxy-thien-2-yl)-sulfonyl)-piperidin-4-yl;

or a stereoisomer, tautomer or pharmaceutically acceptable salt thereof.

10. A compound as in claim 1, wherein

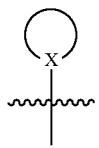

is selected from the group consisting of

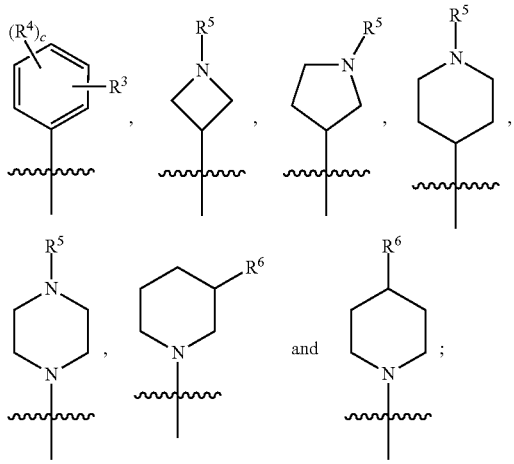

wherein R³ is selected from the group consisting of halogen, hydroxy, cyano, $C_{1-4}$alkyl, halogenated $C_{1-4}$alkyl, hydroxy substituted $C_{1-4}$alkyl, $C_{1-4}$alkoxy, halogenated $C_{1-4}$alkoxy, —CO₂H, —C(O)O—($C_{1-4}$alkyl), —($C_{1-4}$alkyl)-CO₂H, —($C_{1-4}$alkyl)-C(O)O—($C_{1-4}$alkyl), —SO₂—($C_{1-4}$alkyl) and —SO₂-(halogenated $C_{1-4}$alkyl); c is an integer from 0 to 2; and wherein each R⁴ is independently selected from the group consisting of halogen, $C_{1-4}$alkyl, halogenated $C_{1-2}$alkyl, $C_{1-4}$alkoxy and halogenated $C_{1-2}$alkoxy;

wherein R⁵ is selected from the group consisting of —C(O)—($C_{1-4}$alkyl), —C(O)O—($C_{1-4}$alkyl), —SO₂—($C_{1-4}$alkyl) and —SO₂-(halogenated $C_{1-4}$alkyl);

wherein R⁶ is selected from the group consisting of $C_{1-4}$alkyl, halogenated $C_{1-4}$alkyl, —C(O)—NR^E¹R^F, —NR^E—C(O)—($C_{1-4}$alkyl) and —NR^E—SO₂—($C_{1-4}$alkyl); and wherein R^E and R^F are each independently selected from the group consisting of hydrogen, methyl and ethyl;

or a stereoisomer, tautomer or pharmaceutically acceptable salt thereof.

11. A compound as in claim 1 wherein

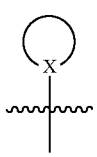

is selected from the group consisting of

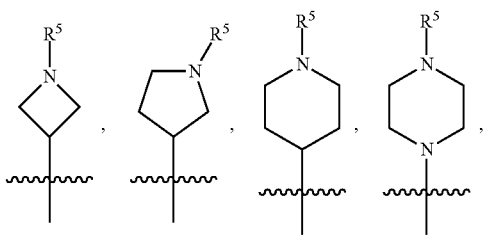

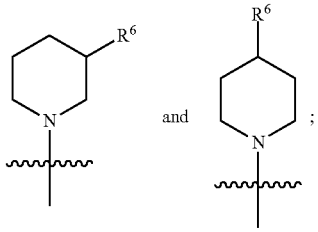

R⁵ is

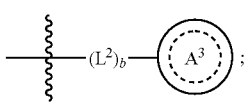

R⁶ is

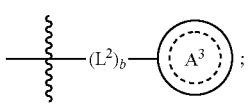

b is an integer from 0 to 1;

L² is selected from the group consisting of —CH₂—, —CH₂CH₂—, —NH—, —N(CH₃)—, —C(O)— and —SO₂—;

provided that when

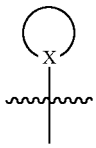

is selected from the group consisting of

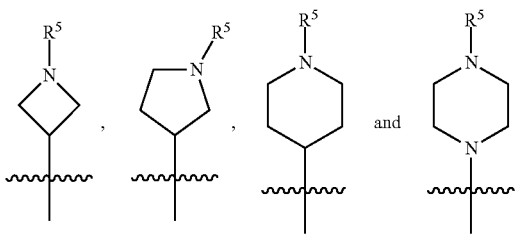

then b is 0 or b is 1 and L² is other than —NH— or —N(CH₃)—;

is selected from the group consisting of phenyl, furan-2-yl, thien-2-yl;

wherein the phenyl is optionally substituted with a substituent selected from the group consisting of halogen, hydroxy, cyano, C₁₋₄alkyl, halogenated C₁₋₄alkyl, hydroxy substituted C₁₋₄ alkyl, C₁₋₄alkoxy, halogenated C₁₋₄alkoxy, —CO₂H, —C(O)O—(C₁₋₄alkyl), —(C₁₋₄alkyl)-CO₂H, —(C₁₋₄alkyl)-C(O)O—(C₁₋₄ alkyl), —SO₂—(C₁₋₄alkyl) and —SO₂-(halogenated C₁₋₄alkyl);

and wherein the phenyl is further optionally substituted with one to two additional substituents independently selected from the group consisting of halogen, C₁₋₄ alkyl, halogenated C₁₋₂alkyl, C₁₋₄ alkoxy and halogenated C₁₋₂alkoxy;

and wherein the furan-2-yl or thien-2-yl is optionally substituted with a substituent selected from the group consisting of halogen, C₁₋₄ alkyl, halogenated C₁₋₄alkyl, C₁₋₄alkoxy, halogenated C₁₋₄ alkoxy, —CO₂H, —C(O)O—(C₁₋₄ alkyl) and —C(O)—NR^G R^H; wherein R^G and R^H are each independently selected from the group consisting of hydrogen, methyl and ethyl;

or a stereoisomer, tautomer or pharmaceutically acceptable salt thereof.

12. A pharmaceutical composition comprising a pharmaceutically acceptable carrier and a compound of claim 1.

13. A process for making a pharmaceutical composition comprising mixing a compound of claim 1 and a pharmaceutically acceptable carrier.

\* \* \* \* \*